United States Patent [19]

Gerald et al.

[11] Patent Number: 5,766,879
[45] Date of Patent: Jun. 16, 1998

[54] DNA ENCODING 5-HT$_4$ SEROTONIN RECEPTORS AND USES THEREOF

[75] Inventors: Christophe Gerald, Ridgewood; Paul R. Hartig, Pennington; Theresa Branchek, Teaneck, all of N.J.; Richard L. Weinshank, New York, N.Y.

[73] Assignee: Synaptic Pharmaceutical Corporation, Paramus, N.J.

[21] Appl. No.: 446,822

[22] PCT Filed: Dec. 22, 1993

[86] PCT No.: PCT/US93/12586

§ 371 Date: Jul. 31, 1995

§ 102(e) Date: Jul. 31, 1995

[87] PCT Pub. No.: WO94/14957

PCT Pub. Date: Jul. 7, 1994

Related U.S. Application Data

[63] Continuation-in-part of Ser. No. 996,772, Dec. 24, 1992, Pat. No. 5,472,866.

[51] Int. Cl.$^6$ .................................................. C12N 15/12
[52] U.S. Cl. .................. 435/69.1; 536/23.1; 536/23.5; 435/252.3; 435/325; 435/320.1; 435/254.11
[58] Field of Search ............................. 536/23.1, 24.31, 536/24.5, 23.5; 435/240.2, 252.3, 254.11, 254.2, 69.1, 325, 320.1

[56] References Cited

U.S. PATENT DOCUMENTS

| | | | |
|---|---|---|---|
| 4,985,352 | 1/1991 | Julius et al. | 435/6 |
| 5,155,218 | 10/1992 | Weinshank et al. | 536/23.5 |
| 5,242,822 | 9/1993 | Marullo et al. | 435/252.3 |
| 5,360,735 | 11/1994 | Weinshank et al. | 435/240.2 |
| 5,472,866 | 12/1995 | Gerald et al. | |
| 5,476,782 | 12/1995 | Weinshank et al. | |

FOREIGN PATENT DOCUMENTS

| | | |
|---|---|---|
| 9227174 | 11/1991 | WIPO. |
| 9311147 | 6/1993 | WIPO. |
| 9314201 | 7/1993 | WIPO. |
| 9410311 | 5/1994 | WIPO. |

OTHER PUBLICATIONS

Clarke, D.E. et al., TiPS 10:385–386, (1989).
Blockaert, J. et al., Mol. Pharm. 37(3):408–411, (1990).
Grandy, D.K. et al., PNAS USA. 88:9175–9179, (1991).
Flynn, D.L. et al., J. Med. Chem. 35:1486–1489, (1992).
Gura, T. 1995 (Oct. 27), Science, vol. 270 pp. 575–577.
NTIS Publication No. PB93–139335, Oct. 26, 1992.
Weinshank, R.L. et al., Molecular Analysis of Serotonin Receptor Subtypes.
Langer, S. Z., et al. (eds.) Int. Acad. Biomed. Drug Reg., Basel, Karger, 1992 1:1–12.
Loric, S., et al., FEBS. 1992 312:(2, 3):203–207.

*Primary Examiner*—Marianne P. Allen
*Attorney, Agent, or Firm*—John P. White; Cooper & Dunham LLP

[57] ABSTRACT

This invention provides an isolated nucleic acid molecule encoding a mammalian 5-HT$_4$ receptor and an isolated nucleic acid molecule encoding a human 5-HT$_4$ receptor, an isolated protein which is a mammalian 5-HT$_4$ receptor, an isolated protein which is a human 5-HT$_4$ receptor, vectors comprising an isolated nucleic acid molecule encoding a mammalian 5-HT$_4$ receptor, vectors comprising an isolated nucleic acid molecule encoding a human 5-HT$_4$ receptor, mammalian cells comprising such vectors, antibodies directed to the 5-HT$_4$ receptor, nucleic acid probes useful for detecting nucleic acid encoding a mammalian or human 5-HT$_4$ receptor, antisense oligonucleotides complementary to any sequences of a nucleic acid molecule which encodes a mammalian or human 5-HT$_4$ receptor, pharmaceutical compounds related to the human 5-HT$_4$ receptor, and non-human transgenic animals which express DNA encoding a normal or a mutant mammalian or human 5-HT$_4$ receptor. This invention further provides methods for determining ligand binding, detecting expression, drug screening, and treatments for alleviating abnormalities associated with a human 5-HT$_4$ receptor.

16 Claims, 32 Drawing Sheets

FIG. 1A

```
1    AGCCTTGCCGAGCCTGGCTTGGTTGGAAGGAGGATGCTCTGCCGTGCCAGGGTCCTG         60
61   TGGGCACTGACATCCAACGTACTCATGCCCATTTCCTGTAATGGACAGACTTGATGCTAA    120
                                          M  D  R  L  D  A  N          7
121  TGTGAGTTCCAACGAGGGTTTCGGTGTCTGTGGAGAAGGTCGTGCTCACGTTCTTCCGC    180
8     V  S  S  N  E  G  F  G  S  V  E  K  V  V  L  T  F  F  A        27
181  AATGGTTATCCTGATGGCCAACCTGCTGGTTGCTGATGGTTGCTGTGTGCAGGGA          240
28    M  V  I  L  M  A  I  L  G  N  L  L  V  M  H  V  A  V  C  R  D   47
241  CAGGCAGCTCAGGAGAAATAAAACCAATTATTCATTGTGTCTCTTGCCTTTGCTGATCT    300
48    R  Q  L  R  K  I  K  T  N  Y  F  I  V  S  L  A  F  A  D  L     67
301  GCTGGTTTCGGTGCTGGTGAATGCCTTCGGTGCCATTGAGTTGGTCCAAGACATCTGGTT    360
68    L  V  S  V  L  V  N  A  F  G  A  I  E  L  V  Q  D  I  W  F     87
361  TTATGGGagatgttttgcctggtccggacctctctggatgtcctactaccacagcatc    420
88    Y  G  E  M  F  C  L  V  R  T  S  L  D  V  L  L  T  A  S       107
421  aattttcacctctgctgcattccctGGATAGTATTATGCCATCTGCTGTCAACCTTT      480
108   I  F  H  L  C  C  I  S  L  D  R  Y  Y  A  I  C  C  Q  P  L    127
481  GGTTATAGAAACAAGATGACCCCTCTACGCCATTAATGCAAGGCTGGAACATCGGACATAGT 540
128   V  Y  R  N  K  M  T  P  L  R  I  A  L  N  L  G  G  W  V       147
541  CATTCCCATGTTTATATCTTTTCTCCCATAATGCAAGGCTGGAACATCGGACATAGT     600
148   I  P  M  F  I  S  F  L  P  I  M  Q  G  W  N  N  I  G  I  V    167
601  TGATGTGATAGAGAAGAAGGAAATTCAACCACAACTCTACATTCTGTCTTCAT           660
168   D  V  I  E  K  R  K  F  N  H  N  S  N  T  F  C  V  F  M       187
661  GGTCAACAAGCCTATGCCATCACCTGCTCTGTGGCCTTCTACATCCCGTTTCTCCT        720
188   V  N  K  P  Y  A  I  T  C  S  V  V  A  F  Y  I  P  F  L  L    207
```

FIG. 1B

```
721  CATGGTGCTGGCCTATTACCGTATCTATGTCACTGCTAAGGAGCATGCCCAGCAGATCCA   780
208    M  V  L  A  Y  Y  R  I  Y  V  T  A  K  E  H  A  Q  Q  I  Q   227
781  GATGTTACAACGGGCAGGAGCCACCTCTGAAAGCAGGCCCCAGACAGCTGACCAGCACAG   840
228    M  L  Q  R  A  G  A  T  S  E  S  R  P  Q  T  A  D  Q  H  S   247
841  CACACATCGGCATGCGGACACAGAGACCAAAGCAGCCAAGACTTTATGTGTCATCATGGGCTG   900
248    T  H  R  M  R  T  E  T  K  A  K  T  L  C  V  I  M  G  C   267
901  CTTCTGTTTCTGCTGGGCCCCCCTTCTTTGTCACCAATATTGTGGACCCTTTCATAGACTA   960
268    F  C  F  C  W  A  P  F  F  V  T  N  I  V  D  P  F  I  D  Y   287
961  CACTGTGCCCGAGAAGGTGTGGACTGCTTTCCTCTGGCTATATCAATTCAGGGTT      1020
288    T  V  P  E  K  V  W  T  A  F  L  W  L  G  Y  I  N  S  G  L   307
1021 GAACCCTTTCTCTATGCCTTCTTGAATAAGTCTTTCAGACGTGCCTTCCTTATCATCCT   1080
308    N  P  F  L  Y  A  F  L  N  K  S  F  R  R  A  F  L  I  I  L   327
1081 CTGCTGTGATGATGAGCGATACAAAAGACCCCCATTCTGGGCCAGACTGTCCCCTGTTC   1140
328    C  C  D  D  E  R  Y  K  R  P  P  I  L  G  Q  T  V  P  C  S   347
1141 AACCACAACCATTAATGGATCCACTCATGTGCTAAGGTATACAGTTTGCATAGTGGTCA   1200
348    T  T  I  N  G  S  T  H  V  L  R  Y  T  V  L  H  S  G  Q   367
1201 ACACCAGGAACTGGAGAAGTTGCCCATACACAATGACCCAGAGTCCCTGAATCATGCTT   1260
368    H  Q  E  L  E  K  L  P  I  H  N  D  P  E  S  L  E  S  C  F   387
1261 TTGATTGAAGACGTGGCTTGCCTTTAGGGGTTCATCCCATCTGTGTCTGCATGAACAGGT   1320
        *
1321 TACTATGGAATCACTCCTGACTCTGGGCATCACCAGTGAAGCATGAGCATGGTGAGGCAG   1380
1381 GGTCCGGTGAAGGTGCACAGAGGACACATTGAGTGGGACCTGAACCCAGCACATTAAGG   1440
1441 ATTTCAGAAACCGTGTGGGGATTTGAGATGTCATCAGAGACCCAGTGTCTTACCAGAGCCCA   1500
1501 ACTGGCACCTCCCATTCCACGCTGACATGGTCAGTGGTCAGCACCTCTCCAGGGG       1560
1561 CAGGAGCTGACTACCTCCTAATGTGGGGGAGCTCTTAATTGTGTGGAAGTTCAGTCAT     1620
1621 TCATTGGTGGACAGTCTCGCTG    1642
```

FIG. 2A

```
1    CAGCGGCACGAGCAGGGCAGAAGCAGGGCTCTGCGCTAAAGGTGGCCGCAGGATCTGCC    60
61   AGGGTGCCGCTCTCCAGGAGCCCACGTGTGAAGGGTCCTGTGGGCACTGACATCCAACGTACTCA   120
121  TCAGAACCCCAGGAGCCCACGTGTGAAGGGTCCTGTGGGCACTGACATCCAACGTACTCA   180
181  TGCCCATTTCCTGTAATGGACACAGGTGATGCTAATGTGAGTTCCAAGAGGGTTTCGGG   240
                M  D  R  L  D  A  N  V  S  S  N  E  G  F  G       15
241  TCTGTGGAGAAGGTCGTACTGCTCACGTTCTTCGCAATGGTTATCCTGATGGCCATCCTG   300
      S  V  E  K  V  V  L  T  F  F  A  M  V  I  L  M  A  I  L     35
301  GGCAACCCTGCTGGTGATGGTTGCTGTGTGCAGGACAGGCAGCTCAGGAAATAAAACC    360
      G  N  L  L  V  M  V  A  V  C  R  D  R  Q  L  R  K  I  K  T  55
361  AATTATTTCATTGTGTCTCTTGCTTTTGCTGATCTGCTGGTTTCGGTGGTGCTGGTGAATGCC   420
      N  Y  F  I  V  S  L  A  F  A  D  L  L  V  S  V  L  V  N  A  75
421  TTCGGTGCCATTGAGTTGGTCCAAGACATCTGGTTTTATGGGGAGATGTTTTGCCTGGTC   480
      F  G  A  I  E  L  V  Q  D  I  W  F  Y  G  E  M  F  C  L  V  95
481  CGGACCCTCTCTGGATGTCCTACTCCACCACAGCATCAATTTTCACCTCTGCCTTTCC    540
      R  T  S  L  D  V  L  L  T  A  S  I  F  H  L  C  C  I  S    115
541  CTGGATAGGTATTATGCCATCTGCTGTCAACCTTTGGTTTATAGAAACAAGATGACCCCT   600
      L  D  R  Y  Y  A  I  C  C  Q  P  L  V  Y  R  N  K  M  T  P  135
601  CTACGCATCGCATTAATGCTGGGAGGCTGCTGGGTCATTCCCATGTTTATCTTTTCTC   660
      L  R  I  A  L  M  L  G  G  C  W  V  I  P  M  F  I  S  F  L  155
661  CCCATAATGCAAGGCTGGAACAACATCGGGAACATAGTTGATGTGATAGAGAAAGGAAATTC   720
      P  I  M  Q  G  W  N  N  I  G  I  V  D  V  I  E  K  R  K  F  175
721  AACCACAACTCTAACTCTGTCTTCATGGTCAACAAGCCCTATGCCATCACC    780
      N  H  N  S  T  F  C  V  F  M  V  N  K  P  Y  A  I  T       195
781  TGCTCTGTGGTGGCCTTCTACATCCCGTTTCTCTCATGGTGGCCTATTACCGTATC   840
      C  S  V  V  A  F  Y  I  P  F  L  M  V  L  A  Y  Y  R  I    215
```

FIG. 2B

```
841   TATGTCACTGCTAAGGAGCATGCCCAGCAGATCCAGATGTTACAACGGGCAGGAGCCACC   900
216    Y  V  T  A  K  E  H  A  Q  Q  I  Q  M  L  Q  R  A  G  A  T    235
901   TCTGAAAGCAGGCCCCAGACAGCTGACCAGCACAGCACACATCGGACACAGAGACC       960
236    S  E  S  R  P  Q  T  A  D  Q  H  S  T  H  R  M  R  T  E  T    255
961   AAGCAGCCAAGACTTTATGTGTCATGGGCTGCTTCTGTTTCTGCTGGCCCCCTTC        1020
256    K  A  K  T  L  C  V  M  G  C  F  C  V  A  P  F                275
1021  TTTGTCACCAATATTGTGGACCCTTTCATAGACTACACTGTGCCCGAGAAGGTGTGGACT   1080
276    F  V  T  N  I  V  D  P  F  I  D  Y  T  V  P  E  K  V  W  T    295
1081  TTCCTCTGGCTTGGCTATATCAATTCAGGGTTGAACCCTTTTCTCTATGCCTTCTTG      1140
296    A  F  L  W  L  G  Y  I  N  S  G  L  N  P  F  L  Y  A  F  L    315
1141  AATAAGTCTTTCAGACGTGCCTTCCTTATCATCCTCTGCTGTGATGAGGCTACAAA       1200
316    N  K  S  F  R  R  A  F  L  I  L  C  C  D  D  E  R  Y  K       335
1201  AGACCCCCATTCTGGGCCAGACTGTCCCCTGTTCAACCACACCATTAATGGATCCACT    1260
336    R  P  I  L  G  Q  T  V  P  C  S  T  T  I  N  G  S  T          355
1261  CATGTGCTAAGGGATACAGTGGAATGGTGGCCAATGGTGGCCAGTGATGATACGTCACTTCACA 1320
356    H  V  L  R  D  T  V  E  C  G  G  Q  W  E  S  R  C  H  L  T    375
1321  GCAACTTCCCTTTGGTGGCTGTCAGCAGTGATGATACGTAGGCCCCAGGACAATGACCTA  1380
376    A  T  S  P  L  V  A  A  Q  P  V  I  R  R  P  Q  D  N  D  L    395
1381  GAAGACAGCTGTAGCTTGAAAAGAAGCCAGTCCTAAGCTGCTACTTCGGTGTATGTGGCT  1440
396    E  D  S  C  S  L  K  R  S  Q  S  *                            406
1441  GCCCCTGGCACTTTGTCTCCAAGGCTTTCCAAGAGAAGCATGAGGCAATCCACCCTGGACTT 1500
1501  CCCGCCACGATTCTAGCAGGGGTATTAGAGAAGAAGTCAGGGAGAGAAGGGCTTCCTCCT  1560
1561  TAGCTTTCTTCTCAACATTTCTTCTTCCTGGAGTCTCCACTCTTGCTCTTGGTGGTCTC   1620
1621  TGAAGTCCACGACCAGTTCCAGTCCTCTGCTCTGTCTCCAGTGTCTCTTGTAAATGTTACCGT 1680
1681  GTCGATTTTCAGTTTCCAAACATGCCTTCTTGAAGTGTCATCTTACGATACTGTCAAA    1740
1741  ACATGTGCCTGTCTGTGATCACACTTCTT   1768
```

FIG. 3

```
  1 MDRLDANVSSNEGFGSVEKVVLLTFFAMVILMAILGNLLVMVAVCRDRQL  50
    ||||||||||||||||||||||||||||||||||||||||||||||||||
  1 MDRLDANVSSNEGFGSVEKVVLLTFFAMVILMAILGNLLVMVAVCRDRQL  50

51 RKIKTNYFIVSLAFADLLVSVLVNAFGAIELVQDIWFYGEMFCLVRTSLD 100
    ||||||||||||||||||||||||||||||||||||||||||||||||||
 51 RKIKTNYFIVSLAFADLLVSVLVNAFGAIELVQDIWFYGEMFCLVRTSLD 100

101 VLLTTASIFHLCCISLDRYYAICCQPLVYRNKMTPLRIALMLGGCWVIPM 150
    ||||||||||||||||||||||||||||||||||||||||||||||||||
101 VLLTTASIFHLCCISLDRYYAICCQPLVYRNKMTPLRIALMLGGCWVIPM 150

151 FISFLPIMQGWNNIGIVDVIEKRKFNHNSNSTFCVFMVNKPYAITCSVVA 200
    ||||||||||||||||||||||||||||||||||||||||||||||||||
151 FISFLPIMQGWNNIGIVDVIEKRKFNHNSNSTFCVFMVNKPYAITCSVVA 200

201 FYIPFLLMVLAYYRIYVTAKEHAQQIQMLQRAGATSESRPQTADQHSTHR 250
    ||||||||||||||||||||||||||||||||||||||||||||||||||
201 FYIPFLLMVLAYYRIYVTAKEHAQQIQMLQRAGATSESRPQTADQHSTHR 250

251 MRTETKAAKTLCVIMGCFCFCWAPFFVTNIVDPFIDYTVPEKVWTAFLWL 300
    ||||||||||||||||||||||||||||||||||||||||||||||||||
251 MRTETKAAKTLCVIMGCFCFCWAPFFVTNIVDPFIDYTVPEKVWTAFLWL 300

301 GYINSGLNPFLYAFLNKSFRRAFLIILCCDDERYKRPPILGQTVPCSTTT 350
    ||||||||||||||||||||||||||||||||||||||||||||||||||
301 GYINSGLNPFLYAFLNKSFRRAFLIILCCDDERYKRPPILGQTVPCSTTT 350

351 INGSTHVLRYTVLHSGQ...............HQELEKLPIHNDPESLES 385
    ||||||||| ||  :||              |.: : | .|| |   :|
351 INGSTHVLRDTVECGGQWESRCHLTATSPLVAAQPVIRRPQDNDLE..DS 398

386 CF 387
     |
399 CSLKRSQS 406
```

```
         HSTHRMRTETKAAKTLCVIMGCFCFCWAPFFVTNIVDPFIDYTVPEKV·     293
S10-95   HSTHRMRTETKAAKTLCVIMGCFCFCWAPFFVTNIVDPFIDYTVPEKV·     293
S10-87   KNISIFKREQKAATTLGIIVGAFTVCHLPFFLLSTARPFICGTSCSCIPL     363
Hp78     ·THQSISNEQKACKVLGIVFFLFVVMCPFFITNIMAVICKESCNENVIG     359
5-HT2 Rat GTMQAINEKKASKVLGIVFFVFLIMCPFFITNILSVLCGKACNQKLME·    349
5-HT1C Rat ········KATVTTLAAVNGAFIICWFPYFTVFVFVYRGLKGDDAINEA·   268
Hist2 Dog                                   VII S10-95   ·WTA·FLWLGYINSGLNPFLYAFLNKSFRRAFLIILCCDDERYKRPPILG     341
S10-87   ·WTA·FLWLGYINSGLNPFLYAFLNKSFRRAFLIILCCDDERYKRPPILG     341
Hp78     WVERTFLWLGYANSLINPFIYAFFNRDLRTTYRSLLQCQ·········     402
5-HT2 Rat ALLNVFVWIGYLSSAVNPLVYTLFNKTYRSAFSRYIQCQYKENRKPLQLI   409
5-HT1C Rat KLLNVFVWIGFVCSGINPLVYTLFNKIYRRAFSKYLRCDYKPDKKP·PVR   398
Hist2 Dog FEAVVLWLGYANSALNPILYATLNRDFRTAYQQLF·····RCRPASHNA·   312

S10-95   QIVPESTTINGSTNVL··RDTVECGGQWESRCHLTATSPLVAAQPVIR     388
S10-87   QIVPCBITTINGSTHVL··RYTVYLHSGQH······ELEK           376
Hp78     ·······YRNINRKL·SAAGHHEALKLAERPEFVLQNADYCRK        440
5-HT2 Rat ·LVNTIPALAYKSSQLQVGQKKNSQEDAERTVDDCSMVTLGKQQSEENCTD 459
5-HT1C Rat QIPRVAAALSQRELNVNIYRHENERVARKANDPEPGIEMQVENLELPVN   448
Hist2 Dog Q····ETSLRSNSSQL·ARNQSREPHRQEEKPLXLQVWSGTEVTAPR    354

S10-95   RPQQNDLEDDCSLKRSQS·                    406
S10-87   LPIHNDPBSLESCF·····                    387
Hp78     KGHDS·NIETVNEKVSEV·                    445
5-HT2 Rat NIETVNEKVSEV······                    471
5-HT1C Rat PSNVVSERISSV······                    460
Hist2 Dog GATDR············                    359
```

FIG. 5

```
574  TTGGTCTATAGGAACAAGATGACCCCTCTGCGCCATTAATGCTGGGAGGCTGCTGG         633
127   L  V  Y  R  N  K  M  T  P  L  R  I  A  L  M  L  G  G  C  W    146
634  GTCATCCCCACGTTTATTTCTTTTCTCCCTATAAATGCAAGGCTGGAATAACATTGGCATA    693
147   V  I  P  T  F  I  S  F  L  P  I  M  Q  G  W  N  N  I  G  I    166
694  ATTGATTGATAGAAAAGAGGAAGTTCAACCAGAACTCTAACTCTACGTGTCTTC            753
167   I  D  L  I  E  K  R  K  F  N  Q  N  S  N  T  Y  C  V  F        186
754  ATGGTCAACAAGCCCTACGCCATCACCTGCTCTGTGGCCTTCTACATCCCATTTCTC         813
187   M  V  N  K  P  Y  A  I  T  C  S  V  A  F  Y  I  P  F  L        206
814  CTCATGGTGCTGGCCTATTACCGCATCTATGTCACAGCTAAGGAGCATGCCCATCAGATC     873
207   L  M  V  L  A  Y  Y  R  I  Y  V  T  A  K  E  H  A  H  Q  I    226
874  CAGATGTTACAACGGGCAGGAGCAGGCCTCAGTCCGAGAGCAGCCCTCAGTGCAGACCAGCAT  933
227   Q  M  L  Q  R  A  G  A  S  E  S  R  P  Q  S  A  D  Q  H        246
934  AGCACTCATCCGATGAGGACAGAGACCAAAGCAGCCAAGACCCTGTGCATCATCATGGGT     993
247   S  T  H  P  M  R  T  E  T  K  A  K  T  L  C  I  I  M  G        266
994  TGCTTCTGCCTCTGCTGGGCACCATTCTTTGTCACCAATATTGTGGATCCTTTCATAGAC    1053
267   C  F  C  L  C  W  A  P  F  F  V  T  N  I  V  D  P  F  I  D    286
1054 TACACTGTCCCTGGGCAGGTGTGGACTGCTTTCCTCTGGCTATATCAATTC             1109
287   Y  T  V  P  G  Q  V  W  T  A  F  L  W  L  G  Y  I  N           304
```

FIG. 6

```
574   TTGGTCTCTATAGGAACAAGATGACCCCCTCTGCGCATTAATGCTGGGAGGCTGCTGG   633
              T                 A                    A
634   GTCATCCCCACGTTTATTTCTTTCTCCCTATAATGCAAGGCTGGAATAACATTGGCATA   693
         T       T  A                    C                C
694   ATTGATTTGATAGAAAAGAGGAAGTTCAACCAGAACTCTAACTCTACGTACTGTGTCTTC   753
      G       G     G G  A    C                           A T
754   ATGGTCAACAAGCCCCTACGCCCATCACCTGCTCTGTGGTGGCCTTCTACATCCCATTCTC   813
              T                                                G
814   CTCATGGTGTGCTGGCCTATTACCGCATCTATGTCACAGCTAAGGAGCATGCCCATCAGATC   873
                             T      T                          G
874   CAGATGTTACAACGGGCAGGAGCCCTCCTCCGAGAGCAGGCCCTCAGTCGGCAGACCAGCAT   933
                     A    T  A      C   AA T                 C
934   AGCACTCATCCGATGAGGACAGAGGACCAAAGCAGCCAAGACCCTGTGCATCATCATGGGT   993
      A    GC  C                                     TT A  TG    C
994   TGCTTCTGCCCTCTGCTGGGCACCATTCTTTGTCACCAATATTGTGGATCCTTTCATAGAC   1053
              TT            C C                                C
1054  TACACTGTCCCTGGGCAGGTGTGGACTGCTTTCCCTCTGGCTCGGCTATATCAATTC   1109
      G C A A                                  T
```

FIG. 7

```
127  LVYRNKMTPLRIALMLGGCWVIPTFISFLPIMQGWNNIGIIDLIEKRKFNQNSNSTYCVF  186
                              M                   V V       H  F

187  MVNKPYAITCSVVAFYIPFLLMVLAYYRIYVTAKEHAHQIQMLQRAGASSESRPQSADQH  246
                                          Q       T   T

247  STHPMRTETKAAKTLCIIMGCFCLCWAPFFVTNIVDPFIDYTVPGQVWTAFLWLGYIN  304
        R                  V        F              EK
```

FIG. 11A

```
   1 TTGGTCTATAGGAACAAGATGACCCCTCTGCGCATCGCATTAATGCTGGAGGCTGCTGG    60
  61 GTCATCCCCACGTTTATTTCTTTCTCCCTATAAATGCAAGCTGGAATAACATTGGCATA   120
 121 ATTGATTTGATAGAAAAGAGGAAGTTCAACTGCTCTGTGTGCCTTCTACATCCATTCTC   180
 181 ATGGTCAACAAGCCCTACGCCATCTATTACCGCGCCTTCTGTGTGGCACAGTCACAGATC   240
 241 CTCATGGTGCTGGCCATCTATTACCGCGAGAGCCCTCCGAGACCCTCAGTGGCATGCAT   300
 301 CAGATGTTACAACGGGCAGGAGCAGAGACAAAGCAGCCAAGACCCTGTGCATCATCGGGT   360
 361 AGCACTCATCGCATGAGGACAGAGGCCAAAGCAGCCAAGACCCTGTCATCATCATGGGT   420
 421 TGCTTCTCCCTCTGGGCAGGTGTGACCATTCTTGTCACCAATATTGTGGATCCTTTCATAGAC   480
 481 TACACTGTCCCTGGGCAGGTGTGACCATTCTTGTCACCAATATTGTGGATCCTTTCATAGAC   540
 541 TTGAACCCTTTTCTACGCCTTCTTGAATAAGTCTTTTAGACGTGCCTTCTCATCATC   600
 601 CTCTGCTGTGATGAGCGCTACCGAAGACCTTCCATTCTGGGCCAGACTGTCCCTTGT   660
 661 TCAACCACACATTAATGGATCCACACATGTACTAAGGTACACCGTTCTGCACAGGGA   720
 721 CATCATCATCAGGAACTCGAGAAACTGCCATACACAATGACCCAGAATCCCTGAATCATGC   780
 781 TTCTGATTGAGG   792
```

```
1                                              ....TTGGTCTATAGGAACAAGATGA    22
451  TAGGTATTATGCCATCTGCTGTCAACCCTTTGGTTTATAGAAACAAGATGA   500
                                                        .
23   CCCCTCTGCGCATCGCATTAATGCTGGGAGGCTGCTGGGTCATCCCCACG    72
          ||||||||||||||||| ||||||||||||||||||||||| |||
501  CCCCTCTACGCATCGCATTAATGCTGGGAGGCTGCTGGGTCATTCCCATG   550
                                                        .
73   TTTATTTCTTTTCTCCCTATAATGCAAGGCTGGAATAACATTGGCATAAT   122
       ||| ||| ||||||||  ||||||||||||||||| ||||| |||| |
551  TTTATATCTTTTCTCCCCATAATGCAAGGCTGGAACAACATCGGCATAGT   600
                                                        .
123  TGATTTGATAGAAAAAGAGGAAGTTCAACCAGAACTCTAACTCTACGTACT   172
      ||| ||||||| ||||||||||||||| |||||||||||||||||| |||
601  TGATGTGATAGAGAAAAGGAAATTCAACAAGAACTCTAACTCTACATTCT   650
                                                        .
173  GTGTCTTCATGGTCAACAAGCCCTACGCCATCACCTGCTCTGTGGTGGCC   222
     |||||||||||||||||||||||||  |||||||||||||||||||||||
651  GTGTCTTCATGGTCAACAAGCCCTATGCCATCACCTGCTCTGTGGTGGCC   700
                                                        .
223  TTCTACATCCCATTTCTCCCTCATGGTGCTGGCCTATTACCGCATCTATGT   272
     |||||||||| ||||| ||||||||||||||||||||||||||  ||||||
701  TTCTACATCCCGTTTCTCCTCATGGTGCTGGCCTATTACCGTATCTATGT   750
```

FIG. 12B

```
 273 CACAGCTAAGGAGCATGCCCATCAGATCCAGATGTTACAACGGGCAGGAG  322
     ||||| ||||||||||||||| |||||||||||||||||||| ||||||||
 751 CACTGCTAAGGAGCATGCCCAGCAGATCCAGATGTTACAACGGGCAGGAG  800

323 CCTCCCTCCGAGAGCAGGCCTCAGTCGGCAGACCAGCATAGCACTCATCGC  372
     | ||| ||||||||||||||||  |||| |||||||||||||| ||||||
 801 CCACCCTCTGAAAGCAGGCCCCAGACAGCTGACCAGCACACAGCACATCGC  850

373 ATGAGGACAGAGACCAAAGCAGCCAAGACCCCTGTGCATCATCATGGGTTG  422
     ||| ||| |||||||||||||||||||||    ||||||| |||||| ||
 851 ATGCGGAGAGAGACCAAAGCAGCCAAGACTTTATGTGTCATCATGGGCTG   900

423 CTTCTGCCCTCTGCTGGGCACCATTCTTTGTCACCAATATTGTGGATCCTT  472
     ||| || ||||| |||||||||   |||||||||||||||||||| ||||
 901 CTTCTGTTTCTGCTGGGCACCCCCCTTTCTTTGTCACCAATATTGTGGACCCTT  950

473 TCATAGACTACACACTGTCCCTGGGCAGGTGTGGACTGCTTTCCTCTGGCTC  522
     ||||||||||||||||||||| ||||| |||||||||||| |||||||||
 951 TCATAGACTACACACTGTGCCCGAGAAGGTGTGGACTGCTGTTCCTCTGGCTT  1000

523 GGCTATATCAATTCCGGGGTTGAACCCTTTTTCTCCTACGCCTTTCTTGAATAA  572
     |||||||||||||||| ||||||||||||||||||||| ||||||||||||||
1001 GGCTATATCAATTCAGGGGTTGAACCCTTTTTCTCTATGCCTTTCTTGAATAA  1050
```

FIG. 12C

```
 573 GTCTTTTAGACGTGCCTTCCTCATCATCCTCTGCTGTGATGATGAGCGCT  622
     |||||||| ||||||||||||||  ||| |||||||||||||||||||||
1051 GTCTTTTCAGACGTGCCTTCCTTATCATCCTCTGCTGTGATGATGAGCGCT 1100

623 ACCGAAGAGACCTTCCATTCTGGGCCAGACTGTCCCTGTTCAACCACAACC  672
     ||  ||| |||||||||||||||||||||||||||||| |||||||||||
1101 ACAAAAGAGACCCCCATTCTGGGCCAGACTGTCCCCTGTTCAACCACAACC 1150

673 ATTAATGGATCCACACAGTACTAAGGTACACCGTTCTGCACAGGGGACA   722
     ||||||||||||||||| ||||||||||||| || |||||||   || ||
1151 ATTAATGGATCCACTCATGTGCTAAGGTATACAGTTTTGCATAGTGGTCA  1200

723 TCATCAGGAACTCGAGAAACTGCCCATACACAATGACCCAGAATCCCTGG  772
     || ||||||||| ||||| |||||||||||||||||||||||| ||||||
1201 ACACCAGGAACTCGGAGAAGTTGCCCATACACAATGACCCAGAGTCCCTGG 1250

773 AATCATGCTTCTGATTGAGG........                        792
     |||||||||||| |||||||
1251 AATCATGCTTTTGATTGAAGACGTGGCTTGCCTTTAGCGGTTCATCCCAT  1300
```

FIG. 13

```
1   ........................LVYRNKMTPLRIALMLGGCWVIPT   24
    |||||||||||||||||||||||||
101 VLLTTASIFHLCCISLDRYYAICCQPLVYRNKMTPLRIALMLGGCWVIPM  150

25  FISFLPIMQGWNNIGIIDLIEKRKFNQNSNSTYCVFMVNKPYAITCSVVA   74
    |||||||||||| |||||||||||| |||||||||||||||||||||||
151 FISFLPIMQGWNNIGIVDVIEKRKFNHNSNSTFCVFMVNKPYAITCSVVA  200

75  FYIPFLLMVLAYYRIYVTAKEHAHQIQMLQRAGASSESRPQSADQHSTHR  124
    ||||||||||||||||||||||||| ||||||||||| |||||| ||||
201 FYIPFLLMVLAYYRIYVTAKEHAQQIQMLQRAGATSESRPQTADQHSTHR  250

125 MRTETKAAKTLCIIMGCFCLCWAPFFVTNIVDPFIDYTVPGQVWTAFLWL  174
    |||||||||||| ||||| |||||||||||||||||||| ||||||||
251 MRTETKAAKTLCVIMGCFCFCWAPFFVTNIVDPFIDYTVPEKVWTAFLWL  300

175 GYINSGLNPFLYAFLNKSFRRAFLIILCCDDERYRRPSILGQTVPCSTTT  224
    |||||||||||||||||||||||||||||||||| ||| |||||||||
301 GYINSGLNPFLYAFLNKSFRRAFLIILCCDDERYKRPPILGQTVPCSTTT  350

225 INGSTHVLRYTVLHRGHHQELEKLPIHNDPESLESCF*  262
    ||||||||||||||| ||||||||||||||||||||||
351 INGSTHVLRYTVLHSGQHQELEKLPIHNDPESLESCF*  387
```

FIG. 14A

```
   1  CCTGTAATGGACAAACTTGATGCTAATGTGAGTTCTGAGGAGGGTTTCGGTCAGTGGAG    60
  61  AAGGTGGTGCTGCTCACGTTCTCTCGACGTTTATCCTGATGCCATCTGGGAACCTG     120
 121  CTGGTGATGGTGTGGCTGTGTGTGCTGGGACAGGCAGCTCAGGACTCAGGACTTGGGACTTCGGTGCTGGTGATGCCCTTTGGTGCC   180
 181  ATTGTATCTCTTGCTTTTGCGAAGACATCTGGGATTTATGGGGAGGTGTTTTGTCTGTTCGGACATCT   240
 241  ATTGAGCTGGTTCAAGACATCTGCTCACAACGGCATCGATTTTCACCTGTGCATTTCTCTGATAGG   300
 301  CTGGACGTCCTGCTCACAACGGCATCGATTTTCACCTGTGCATTTCTCTGATAGG       360
 361  TATTACGCCATCTGCTGCCAGCCTTTGGTCTGTGCATCCCCAGCAAGATGACCCCTGCATC   420
 421  GCATTAATGCTGGAATAACATTGGCATAATTGATTTGATAGAAAAGAGGAAGTTCAACTGAAATG   480
 481  CAAGGCTGGAATAACATTGGCATAATTGATTGATAGAAAAGAGGAAGTTCAACCAGAAC     540
 541  TCTAACTCTACGTACTGTGTTCTCCTCATTTCATGGTCTCAATGGTGTGCAACGTGCTATGTCACA   600
 601  GTGGCCTTCTACATCCCCATTTCTCCTCATGGTGCTTGCCTCTCCTACCGCATCTATGTCACA   660
 661  GCTAAGGAGCATGCCGCAGACATCAGATCCATAGCCCCAGATATCAGATCACCAGCAGAGCCAAAGCAGCC   720
 721  AGGCCTCAGTGTGCATCATCATGGTTGCTTCTGCCTCTGCCCTGGGCAGGTGTGACTGCTTCACC   780
 781  AAGACCCTGTGCATCATCATGGTTGCTTCTGCCTCTGCCCTGGGCAGGTGTGACTGCTTCACC   840
 841  AATATTGTGGATCCTTTCATAGACTACACACTGTCCCCTGGGCAGGTGTGACTGCTTCACC   900
 901  TGGCTCGGCTATATCGCCTTCCATCATCCTGTGAACCCTTTCTCTACGCCTTTGAATAAGTCT   960
 961  TTTAGACGTGCCTGCTTCCATCATCCTGTGTTCAACCACAACCATTAATGATGAGCGCTACCGAAGACCTTCC  1020
1021  ATTCTGGGCCAGACTGTGGTGCCAGTGTGGCCAGTGTGGTGGGAGAGTCAGTGTCACCCGCCAGCAACTTCT  1080
1081  AGGGATGCAGTGGAGTGCTCAGCAGTGACACTTAGGCCCCTGGACAATGACCCAGAAGACA  1140
1141  CCTTTGGTGCCTCCGAAAGAGGGCCAGGTCCTAAGCTCCTGTGCGCGACTGCACCCGGC  1200
1201  GCCATGCCCTCCGAAAGAGGGCCAGGTCCTAAGCTCCTGTGCGCGACTGCACCCGGC      1260
1261  ATTCTCTTCACCTGAGGCTTTCCGTCCGCCAGTGCAGGTGCAGGAACCCGGTGCTCGCTGGG 1316
```

```
7   ATGGACAAACTTGATGCTAATGTGAGTTCTGAGGAGGGTTTCGGGTCAGT   56
    ||||||| ||||||||| ||||||||||||||||| ||||||||||||||
152 ATGGACAGACTTGATGCTAATGTGAGTTCCAACGAGGGTTTCGGGTCTGT  201

57  GGAGAAGGTGGTGCTGCTCACGTTCTCTCGACGGTTATCCTGATGGCCA   106
    ||||||||||||||||||||||||||| || |  ||||||||||||||||
202 GGAGAAGGTCGTACTGCTCACGTTCTTCGCAATGGTTATCCTGATGGCCA  251

107 TCTTGGGGAACCTGCTGTGGTGGCTGTGTGCTGGGACAGGCAGCTC      156
    || |||| ||||||||||||| |||| |||||||| ||||||||||||
252 TCCTGGGCAACCTGCTGTGGTTGATGGTGCAGGGACAGGCAGCTC       301

157 AGGAAAATAAAACAAATTATTTCATTGTATCTCTTGCTTTTGCGGATCT   206
    ||||||||||| |||||||||||||||| ||||||||||| |||||||
302 AGGAAAATAAAACCAATTATTTCATTGTCTCTTGCCTTTGCTGATCT     351

207 GCTGGTTTCGGTGCTGATGCCCTTTGGTGCCATTGAGCTGGTTCAAG    256
    ||||||||||||||||| |||||||||||||||||||||||| ||||||
352 GCTGGTTTCGGTGCTGAATGCCTTGGTGCCATTGAGTTGGTTCCAAG    401

257 ACATCTGATTTATGGGAGGTGTTTTGTCTTGTTCGGACATCTCTGAC    306
    |||||||| |||||||||| |||||||||||| |  |||| | |||||
402 ACATCTGGTTTTATGGGgagatgtttgcctggtccggacctctctggat  451

307 GTCCTGCTCACAACGGCATCGATTTTCACCTGTGCTGCATTTCTCTGGA  356
    |||||||||| || || ||| ||||| ||||| || || |||  |||||
452 gtcctactcaccacagcatcaattttcacctctgctgcattcccTGGA   501
```

FIG. 15B

```
357  TAGGTATTACGCCATCTGCTGCCAGCCTTTGGTCTCTATAGGAACAAGATGA  406
     ||||||||| ||||||||||||||||||||| |||||||  |||||||||||
502  TAGGTATTATGCCATCTGCTGTCAACCTTTGGTTTATAGAAACAAGATGA  551

407  CCCCTCTGCGCATTAAATGCTGGGAGGCTGCTGGTCATCCCCACG  456
     |||||||| ||||||||||||||||||||||||||||||  ||||
552  CCCCTCTACGCATTAAATGCTGGGAGGCTGCTGGGTCATTCCCATG  601

457  TTTATTTCTTTTTCTCCCTATAATGCAAGGCTGGAATAACATTGGCATAAT  506
     ||||| || ||| |||||| |||||||||||||||||| |||||||||
602  TTTATATCTTTTCTCCCCATAATGCAAGGCTGGAACAACATCGGCATAGT  651

507  TGATTTGATAGAAAAGAGGAAGTTCAACCAGAACTCTAACTCTACGTACT  556
     ||| ||||||||| ||||||||||||||||||| ||||||||||| |||
652  TGATGTGATAGAGAAAAGGAAATTCAACAACACTCTAACTCTACATTCT  701

557  GTGTCTTCATGGTCAACAAGCCCTACGCCATCACCTGCTCTGTGGTGGCC  606
     |||||||||||||||||||||||| |||||||||||||||||||||||||
702  GTGTCTTCATGGTCAACAAGCCCTATGCCATCACCTGCTCTGTGGTGGCC  751

607  TTCTACATCCCCATTTCTCCCTCATGGTGCTATTACCGCATCTATGT  656
     ||||||||||| |||| |||||||||||||||||||||| ||| ||||
752  TTCTACATCCCGTTTCTCCTCATGGTGCTGGCCTATTACCGTATCTATGT  801
```

FIG. 15C

```
657  CACAGCTAAGGAGCATGCCCATCAGATCCAGATGTTACAACGGGCAGGAG  706
     |||  ||||||||||||||||||||||||||||||||| ||||||||||||
802  CACTGCTAAGGAGCATGCCCAGCAGATCCAGATGTTACAACGGGCAGGAG  851

707  CCTCCTCCGAGAGCAGGCCTCAGTCGGCAGAGACCAGCATAGCACTCATCGC  756
     ||  ||| |||||  |||| |||||||  ||||||||||||||| ||||||
852  CCACCTCTGAAAGCAGCCCCAGACAGCTGACCAGCAGCACACATCGC  901

757  ATGAGGACAGAGACCAGCCAAGCAGCCAAGACCCCTGTGCATCATCATGGGTTG  806
     ||| |||||||||||||| ||||||||||||||  ||||||||||||||||||
902  ATGCGGACAGAGACCAGCCAAGCAGCCAAGACTTTATGTGTCATCATGGGCTG  951

807  CTTCTGCCTCTGCTGGGCACCATTCTTTGTCACCAATATTGTGGATCCTT  856
     |||||| ||| |||||||  ||| ||| ||||||||||||||||| ||||
952  CTTCTGTTTCTGCTGGGCCCCCTTCTTTGTCACCAATATTGTGGACCCTT  1001

857  TCATAGACTACACTGTCCCTGGGCAGGTGTGGACTGCTTTCCTCTGGCTC  906
     |||||||||||||||||||||||||||||||||||||||||||||||| |
1002 TCATAGACTACACTGTGCCCGAGAAGGTGTGGACTGCTTTCCTCTGGCTT  1051

907  GGCTATATCAATTCCGGGTTGAACCCTTTTCTACGCCTTCTTGAATAA  956
     ||||||||||||||| ||||||||||||| ||| |||||||||||||
1052 GGCTATATCAATTCAGGGTTGAACCCTTTTCTATGCCTTCTTGAATAA  1101
```

FIG. 15D

```
 957 GTCTTTTAGACGTGCCTTCCTCATCATCCTCTGCTGTGATGATGAGCGCT 1006
     ||||||||||||||||||||||||||||||||||||||||||||||||||
1102 GTCTTTCAGACGTGCCTTCCTTATCATCCTCTGCTGTGATGATGAGCGCT 1151

1007 ACCGAAGACCTTCCATTCTGGGCCAGACTGTCCCTGTTCAACCACAACC  1056
     ||||| |||||||||||||||||||||||||||||||||||||||||||
1152 ACAAAAGACCCCCCATTCTGGGCCAGACTGTCCCCTGTTCAACCACAACC 1201

1057 ATTAATGGATCCACACATGTACTAAGGGATGCAGTGGAGTGTGGTGGCCA 1106
     ||||||||||||| |||||||||||||||||||||||||||||||||||
1202 ATTAATGGATCCACTCATGTGCTAAGGGATACAGTGGAATGTGGTGGCCA 1251

1107 GTGGGAGAGTCAGTGTCACCCGCCAGCAACTTCTCCTTTGGTGTGGCTC  1156
     ||||||||||||||||||||||||||||||||||||||||||||||||
1252 ATGGGAGAGTCGGGTGTCACTCACAGCAACTTCTCCTTTGGGCTGCTC   1301

1157 AGCCCAGTGACACTTAG................................ 1173
     || ||||||||||  |||
1302 AG.CCAGTGATACGTAGGCCCCAGGACAATGACCTAGAAGACAGCTGTAG 1350
```

FIG. 16A

```
1    MDKLDANVSSEEGFGSVEKVVLLTFLSTVILMAILGNLLVMVAVCWDRQL  50
     ||| |||||||| |||||||||||||| ||||||||||||||||| ||||
1    MDRLDANVSSNEGFGSVEKVVLLTFFAMVILMAILGNLLVMVAVCRDRQL  50

51   RKIKTNYFIVSLAFADLLVSVLVMPFGAIELVQDIWIYGEVFCLVRTSLD  100
     ||||||||||||||||||||||||| |||||||||||| ||||||||||
51   RKIKTNYFIVSLAFADLLVSVLVNAFGAIELVQDIWFYGEMFCLVRTSLD  100

101  VLLTTASIFHLCCISLDRYYAICCQPLVYRNKMTPLRIALMLGGCWVIPT  150
     |||||||||||||||||||||||||||||||||||||||||||||||| 
101  VLLTTASIFHLCCISLDRYYAICCQPLVYRNKMTPLRIALMLGGCWVIPM  150

151  FISFLPIMQGWNNIGIIDLIEKRKFNQNSNSTYCVFMVNKPYAITCSVVA  200
     |||||||||||||||| ||||||||| ||||| |||||||||||||||
151  FISFLPIMQGWNNIGIVDVIEKRKFNHNSNSTFCVFMVNKPYAITCSVVA  200

201  FYIPFLLMVLAYYRIYVTAKEHAHQIQMLQRAGASSESRPQSADQHSTHR  250
     ||||||||||||||||||||||||| |||||||||| |||||| |||||
201  FYIPFLLMVLAYYRIYVTAKEHAQQIQMLQRAGATSESRPQTADQHSTHR  250
```

FIG. 16B

```
251 MRTETKAAKTLCIIMGCFCLCWAPFFVTNIVDPFIDYTVPGQVWTAFLWL 300
    ----------------------------------------------
251 MRTETKAAKTLCVIMGCFCFCWAPFFVTNIVDPFIDYTVPEKVWTAFLWL 300
    ----------------------------------------------
301 GYINSGLNPFLYAFLNKSFRRAFLIILCCDDERYRRPSILGQTVPCSTTT 350
    ----------------------------------------------
301 GYINSGLNPFLYAFLNKSFRRAFLIILCCDDERYKRPPILGQTVPCSTTT 350
    ----------------------------------------------
351 INGSTHVLRDAVECGGQWESQCHPPATSPLVAAQPSDT*.......... 389
    ----------------------------------------------
351 INGSTHVLRDTVECGGQWESRCHLTATSPLVAAQPVIRRPQDNDLEDSCS 400
    ----------------------------------------------
401 LKRSQS*.......................................... 406
```

FIG. 17A

```
357 TAGGTATTACGCCATCTGCTGCCAGCCTTTGGTCTATAGGAACAAGATGA 406
              ...............||||||||||||||||||||
  1           ........................TTGGTCTATAGGAACAAGATGA  22

407 CCCCTCTGCGCATCGCATTAATGCTGGGAGGCTGCTGGGTCATCCCCACG 456
    |||||||||||||||||||||||||||||||||||||||||||||||||
 23 CCCCTCTGCGCATCGCATTAATGCTGGGAGGCTGCTGGGTCATCCCCACG  72

457 TTTATTTCTTTTCTCCCTATAAATGCAAGGCTGGAATAACATTGGCATAAT 506
    |||||||||||||||||||||||||||||||||||||||||||||||||
 73 TTTATTTCTTTTCTCCCTATAAATGCAAGGCTGGAATAACATTGGCATAAT 122

507 TGATTTGATAGAAAAGAGGAAGTTCAACCAGAACTCTAACTCTACGTACT 556
    |||||||||||||||||||||||||||||||||||||||||||||||||
123 TGATTTGATAGAAAAGAGGAAGTTCAACCAGAACTCTAACTCTACGTACT 172

557 GTGTCTTCATGGTCAACAAGCCCTACGCCATCACCTGCTCTGTGGTGGCC 606
    |||||||||||||||||||||||||||||||||||||||||||||||||
173 GTGTCTTCATGGTCAACAAGCCCTACGCCATCACCTGCTCTGTGGTGGCC 222

607 TTCTACATCCCCATTTCTCCTCATGGTGCTGGCCTATTACCGCATCTATGT 656
    |||||||||||||||||||||||||||||||||||||||||||||||||
223 TTCTACATCCCCATTTCTCCTCATGGTGCTGGCCTATTACCGCATCTATGT 272

657 CACAGCTAAGGAGCATGCCCATCAGATCCAGATGTTACAACGGGCAGGAG 706
    |||||||||||||||||||||||||||||||||||||||||||||||||
273 CACAGCTAAGGAGCATGCCCATCAGATCCAGATGTTACAACGGGCAGGAG 322
```

FIG. 17B

```
707  CCTCCTCCGAGAGCAGGCCTCAGTGGGCAGACCAGCATAGCACTCATCGC  756
     ||||||||||||||||||||||||||||||||||||||||||||||||||
323  CCTCCTCCGAGAGCAGGCCTCAGTGGGCAGACCAGCATAGCACTCATCGC  372

757  ATGAGGACAGAGACCAAAGCAGCCAAGACCCTGTGCATCATCATGGGTTG  806
     ||||||||||||||||||||||||||||||||||||||||||||||||||
373  ATGAGGACAGAGACCAAAGCAGCCAAGACCCTGTGCATCATCATGGGTTG  422

807  CTTCTGCCTCTGCTGGGCACCATTCTTTGTCACCAATATTGTGGATCCTT  856
     ||||||||||||||||||||||||||||||||||||||||||||||||||
423  CTTCTGCCTCTGCTGGGCACCATTCTTTGTCACCAATATTGTGGATCCTT  472

857  TCATAGACTACACTGTCCCTGGGCAGTGTGGACTGCTTTCCTCTGGCTC   906
     ||||||||||||||||||||||||||||||||||||||||||||||||||
473  TCATAGACTACACTGTCCCTGGGCAGTGTGGACTGCTTTCCTCTGGCTC   522

907  GGCTATATCAATTCCGGGTTGAACCCTTTCTCTACGCCTTCTTGAATAA   956
     ||||||||||||||||||||||||||||||||||||||||||||||||||
523  GGCTATATCAATTCCGGGTTGAACCCTTTCTCTACGCCTTCTTGAATAA   572

957  GTCTTTTAGACGTGCCTTCCCTCATCATCCCTGCTGTGATGATGAGCGCT 1006
     ||||||||||||||||||||||||||||||||||||||||||||||||||
573  GTCTTTTAGACGTGCCTTCCCTCATCATCCCTGCTGTGATGATGAGCGCT  622
```

FIG. 17C

```
1007 ACCGAAGACCTTCCATTCTGGGCCAGACTGTCCCTTGTTCAACCACAACC 1056
     ||||||||||||||||||||||||||||||||||||||||||||||||||
 623 ACCGAAGACCTTCCATTCTGGGCCAGACTGTCCCTTGTTCAACCACAACC  672

1057 ATTAATGGATCCACACATGTACTAAGGATGCAGTGGAGTGTGGTGGCCA  1106
     ||||||||||||||||||||||||||||||||  ||  ||
 673 ATTAATGGATCCACACATGTACTAAGGTACACCGTTCTGCACAGGGGACA  722

1107 GTGGGAGAGTCAGTGTCACCCGCCAGCAACTTCTCCTTTGGTGGCTGCTC 1156
     ||  ||
 723 TCATCAGGAACTCGAGAAACTGCCCATACACAATGACCCAGAATCCCTGG  772

1157 AGCCCAGTGACACTTAG 1173
     ||  ||
 773 AATCATGCTTCTGA... 786
```

FIG. 18

```
101 VLLTTASIFHLCCISLDRYYAICCQPLVYRNKMTPLRIALMLGGCWVIPT 150
    |||||||||||||||||||||
  1 .........................LVYRNKMTPLRIALMLGGCWVIPT 24

151 FISFLPIMQGWNNIGIIDLIEKRKFNQNSNSTYCVFMVNKPYAITCSVVA 200
    |||||||||||||||||||||||||||||||||||||||||||||||||
 25 FISFLPIMQGWNNIGIIDLIEKRKFNQNSNSTYCVFMVNKPYAITCSVVA 74

201 FYIPFLLMVLAYYRIYVTAKEHAHQIQMLQRAGASSESRPQSADQHSTHR 250
    |||||||||||||||||||||||||||||||||||||||||||||||||
 75 FYIPFLLMVLAYYRIYVTAKEHAHQIQMLQRAGASSESRPQSADQHSTHR 124

251 MRTETKAAKTLCIIMGCFCLCWAPFFVTNIVDPFIDYTVPGQVWTAFLWL 300
    |||||||||||||||||||||||||||||||||||||||||||||||||
125 MRTETKAAKTLCIIMGCFCLCWAPFFVTNIVDPFIDYTVPGQVWTAFLWL 174

301 GYINSGLNPFLYAFLNKSFRRAFLIILCCDDERYRRPSILGQTVPCSTTT 350
    |||||||||||||||||||||||||||||||||||||||||||||||||
175 GYINSGLNPFLYAFLNKSFRRAFLIILCCDDERYRRPSILGQTVPCSTTT 224

351 INGSTHVLRDAVECGGQWESQCHPPATSPLVAAQPSDT* 389
    ||||||||| ||  ||  |  |   ::
225 INGSTHVLRYTVLHRGHHQELEKLPIHNDPESLESCF*. 262
```

5,766,879

DNA ENCODING 5-HT₄ SEROTONIN RECEPTORS AND USES THEREOF

The subject application is continuation-in-part of U.S. Ser. No. 07/996,772, filed Dec. 24, 1992, now U.S. Pat. No. 5,472,866, issued Dec. 5, 1995.

BACKGROUND OF THE INVENTION

Throughout this application various publications are referred to by partial citations within parenthesis. Full citations for these publications may be found at the end of the specification immediately preceding the claims. The disclosures of these publications, in their entireties, are hereby incorporated by reference into this application in order to more fully describe the state of the art to which this invention pertains.

Molecular cloning efforts have provided primary amino acid sequence and signal transduction data for a large collection of serotonin receptor subtypes. These include five cloned 5-HT$_1$-like receptors, three cloned 5-HT$_2$ receptors, and one 5-HT$_3$ receptor. The 5-HT$_1$ subfamily includes: 5-HT$_{1A}$ (Fargin, 1988; Kobilka, 1989), 5-HT$_{1B}$/5-HT$_{1D\beta}$ (Weinshank et al., 1991; Demchyshyn et al., 1992; Jin et al., 1992; Adham et al., 1992; Maroteaux et al., 1992; Voight et al., 1991), 5-HT$_{1D\alpha}$ (Branchek et al. 1991; Hamblin and Metcalf, 1991; Weinshank et al., 1992), 5-HT$_{1E}$ (Levy et al., 1992; McAllister et al., 1992; Zgombick et al., 1992) and 5-HT$_{1F}$ (Adham et al., 1993). All five have been shown to couple to the inhibition of adenylate cyclase activity. The 5-HT$_2$ family includes the 5-HT$_2$ receptor (Pritchett et al., 1988), 5-HT$_{1C}$ (Julius et al., 1989) and 5-HT$_{2F}$ (Rat Stomach Fundus; Foquet et al., 1992; Kursar et al., 1992). These receptors all couple to phosphoinositide hydrolysis. The 5-HT$_3$ receptor is a ligand-gated ion channel (Maricq et al., 1991).

Although this work represents enormous success, the absence of molecular biological information on the 5-HT$_4$ receptors, which have been shown in native tissues to couple to the activation of adenylate cyclase as a primary mode of signal transduction (Dumius et al., 1988; Bockaert et al., 1990), is apparent. In a previous copending application (U.S. Ser. No. 971,690, filed Nov. 3, 1992), we reported the cloning of the first mammalian 5-HT receptor that couples to the stimulation of adenylate cyclase activity which we named 5-HT$_{4B}$. The 5-HT$_{4B}$ receptor was subsequently renamed to the "5-HT$_7$ receptor" by the "Serotonin Receptor Nomenclature Committee" of the IUPHAR. The pharmacological properties of this receptor indicated that it was similar to a series of functionally defined 5-HT receptors described in the porcine vena cava (Trevethick et al., 1984), cat saphenous vein, coronary arteries (Cushing and Cohen, 1992), and several vascular dilatory effects (Mylecharane and Phillips, 1989). However, the classically defined 5-HT$_4$ receptor remained to be cloned. We now report the cloning of the pharmacologically-defined 5-HT$_4$ receptor which we have previously called 5-HT$_{4A}$ and now designate as the 5-HT$_4$ receptor. This receptor also stimulates adenylate cyclase activity but unlike 5-HT$_{4B}$, is sensitive to a series of benzamide derivatives which act as agonists or partial agonists at this subtype. The presence of this subtype in the brain, particularly in areas such as the hippocampus, indicates a potential role in cognitive enhancement. In addition, the 5-HT$_4$ receptor has been described functionally in the heart, adrenal, bladder, and alimentary canal indicating potential roles in achalasia, hiatal hernia, esophageal spasm, irritable bowel disease, postoperative ileus, diabetic gastroparesis, emesis and other diseases of the gastrointestinal tract, as well as in cardiac, urinary, and endocrine function.

SUMMARY OF THE INVENTION

This invention provides an isolated nucleic acid molecule encoding a mammalian 5-HT$_4$ receptor. In a preferred embodiment of this invention, the isolated nucleic acid encodes a human 5-HT$_4$ receptor. In another embodiment of this invention, the nucleic acid molecule encoding a human 5-HT$_4$ receptor comprises a plasmid designated pBluescript-hS10 (ATCC Accession No. 75392). In another embodiment of this invention a nucleic acid molecule encoding a mammalian 5-HT$_4$ receptor comprises a plasmid designated pcEXV-S10-87 (ATCC Accession No. 75390). In another embodiment of this invention a nucleic acid molecule encoding a mammalian 5-HT$_4$ receptor comprises a plasmid designated pcEXV-S10-95 (ATCC Accession No. 75391).

This invention provides a nucleic acid probe comprising a nucleic acid molecule of at least 15 nucleotides capable of specifically hybridizing with a unique sequence included within the sequence of a nucleic acid molecule encoding a mammalian 5-HT$_4$ receptor. This invention also provides a nucleic acid molecule of at least 15 nucleotides capable of specifically hybridizing with a sequence included within the sequence of a nucleic acid molecule encoding a human 5-HT$_4$ receptor.

This invention provides an antisense oligonucleotide having a sequence capable of binding specifically to an mRNA molecule encoding a mammalian 5-HT$_4$ receptor so as to prevent translation of the mRNA molecule. This invention also provides an antisense oligonucleotide having a sequence capable of binding specifically to an mRNA molecule encoding a human 5-HT$_4$ receptor so as to prevent translation of the mRNA molecule.

This invention provides a monoclonal antibody directed to a mammalian 5-HT$_4$ receptor. This invention also provides a monoclonal antibody directed to a human 5-HT$_4$ receptor.

This invention provides a pharmaceutical composition comprising an amount of a substance effective to alleviate the abnormalities resulting from overexpression of a mammalian 5-HT$_4$ receptor and a pharmaceutically acceptable carrier. This invention also provides a pharmaceutical composition comprising an amount of a substance effective to alleviate abnormalities resulting from underexpression of mammalian 5-HT$_4$ receptor and a pharmaceutically acceptable carrier.

This invention provides a pharmaceutical composition comprising an amount of a substance effective to alleviate the abnormalities resulting from overexpression of a human 5-HT$_4$ receptor and a pharmaceutically acceptable carrier. This invention also provides pharmaceutical composition comprising an amount of a substance effective to alleviate abnormalities resulting from underexpression of a human 5-HT$_4$ receptor and a pharmaceutically acceptable carrier.

This invention provides a transgenic, nonhuman mammal whose genome comprises DNA encoding a mammalian 5-HT$_4$ receptor so positioned within such genome as to be transcribed into antisense mRNA complementary to mRNA encoding the mammalian 5-HT$_4$ receptor and when hybridized to mRNA encoding the mammalian 5-HT$_4$ receptor, the complementary mRNA reduces the translation of the mRNA encoding the mammalian 5-HT$_4$ receptor.

This invention also provides a transgenic, nonhuman mammal whose genome comprises DNA encoding a human 5-HT₄ so positioned within such genome as to be transcribed into antisense mRNA complementary to mRNA encoding the human 5-HT₄ and when hybridized to mRNA encoding the human 5-HT₄, the complementary mRNA reduces the translation of the mRNA encoding the human 5-HT₄.

This invention provides a transgenic, nonhuman mammal whose genome comprises DNA encoding a mammalian 5-HT₄ receptor so positioned within such genome as to be transcribed into antisense mRNA which is complementary to mRNA encoding the mammalian 5-HT₄ receptor and when hybridized to mRNA encoding the 5-HT₄ receptor, the antisense mRNA thereby prevents the translation of mRNA encoding the 5-HT₄ receptor.

This invention also provides a transgenic, nonhuman mammal whose genome comprises DNA encoding a human 5-HT₄ receptor so positioned within such genome as to be transcribed into antisense mRNA which is complementary to mRNA encoding the human 5-HT₄ receptor and when hybridized to mRNA encoding the human 5-HT₄ receptor, the antisense mRNA thereby prevents the translation of mRNA encoding the human 5-HT₄ receptor.

This invention also provides a method of determining the physiological effects of expressing varying levels of a mammalian 5-HT₄ receptor which comprises producing a transgenic nonhuman animal whose levels of mammalian 5-H₄ receptor expression are varied by use of an inducible promoter which regulates mammalian 5-HT₄ receptor expression.

This invention also provides a method of determining the physiological effects of expressing varying levels of a human 5-HT₄ receptor which comprises producing a transgenic nonhuman animal whose levels of human 5-HT₄ receptor expression are varied by use of an inducible promoter which regulates human 5-HT₄ receptor expression.

This invention further provides a method of determining the physiological effects of expressing varying levels of mammalian 5-HT₄ receptor which comprises producing a panel of transgenic nonhuman animals each expressing a different amount of mammalian 5-HT₄ receptor.

This invention further provides a method of determining the physiological effects of expressing varying levels of human 5-HT₄ receptor which comprises producing a panel of transgenic nonhuman animals each expressing a different amount of human 5-HT₄ receptor.

This invention provides a method for determining whether a compound not known to be capable of specifically binding to a human 5-HT₄ receptor can specifically bind to the human 5-HT₄ receptor, which comprises contacting a mammalian cell comprising a plasmid adapted for expression in a mammalian cell which plasmid further comprises a DNA which expresses a human 5-HT₄ receptor on the cell's surface with the compound under conditions permitting binding of ligands known to bind to a human 5-HT₄ receptor, detecting the presence of any compound bound to the human 5-HT₄ receptor, the presence of bound compound indicating that the compound is capable of specifically binding to the human 5-HT₄ receptor.

This invention provides a method of screening drugs to identify drugs which interact with, and specifically bind to, a human 5-HT₄ receptor on the surface of a cell, which comprises contacting a mammalian cell which comprises a plasmid adapted for expression in a mammalian cell which plasmid further comprises DNA which expresses a human 5-HT₄ receptor on the cell's surface with a plurality of drugs, determining those drugs which bind to the human 5-HT₄ receptor expressed on the cell surface of the mammalian cell, and thereby identifying drugs which interact with, and specifically bind to, the human 5-HT₄ receptor.

This invention provides a method for identifying a compound which specifically binds to and activates or blocks the activation of a human 5-HT₄ receptor on the surface of a mammalian cell, which comprises contacting the mammalian cell which comprises a plasmid adapted for expression in the mammalian cell such plasmid further comprising DNA which expresses the human 5-HT₄ receptor on the cell surface of the mammalian cell with the compound, determining whether the compound activates or blocks the activation of the human 5-HT₄ receptor and thereby identifying the compound as a compound which binds to, and activates or blocks the activation of the human 5-HT₄ receptor.

This invention provides a method for diagnosing a predisposition to a disorder associated with the expression of a human 5-HT₄ receptor allele which comprises: a.) obtaining DNA of subjects suffering from the disorder; b.) performing a restriction digest of the DNA with a panel of restriction enzymes; c.) electrophoretically separating the resulting DNA fragments on a sizing gel; d.) contacting the resulting gel with a nucleic acid probe capable of specifically hybridizing to DNA encoding a 5-HT₄ receptor and labelled with a detectable marker; e.) detecting labelled bands which have hybridized to the DNA encoding a 5-HT₄ receptor labelled with a detectable marker to create a unique band pattern specific to the DNA of subjects suffering from the disorder; f.) preparing DNA obtained for diagnosis by steps a–e; and g.) comparing the unique band pattern specific to the DNA of subjects suffering from the disorder from step e and the DNA obtained for diagnosis from step f to determine whether the patterns are the same or different and to diagnose thereby predisposition to the disorder if the patterns are the same.

BRIEF DESCRIPTION OF FIGURES

FIGS. 1-1 to 1-2: Nucleotide and corresponding amino acid sequence of the S10-87 cDNA clone. Only partial 5' and 3' untranslated sequences are shown.

FIGS. 2-1 to 2-2: Nucleotide and corresponding amino acid sequence of the S10-95 cDNA clone. Only partial 5' and 3' untranslated sequences are shown.

FIG. 3: Comparison of amino acid sequences between clones S10-87 (top row) and S10-95 (bottom row). The overall homology is 96.7%.

FIGS. 4-1 to 4-3: Comparison of the rat S10 receptor deduced amino acid sequences with those of other serotonin receptors and with the canine histamine H2 receptor. Solid bars, the seven putative membrane-spanning domains (TM I–VII). Shading, homologies between the S10 receptors and other receptors. Hp78, 5-HT₄B or hp78a receptor (U.S. Ser. No. 971,960, filed, Nov. 3, 1992, copending).

FIG. 5: Nucleotide and amino acid sequences of the human S10 PCR clone. The numbering is given according to the rat S10-95 clone.

FIG. 6: Comparison of nucleotide sequences between the human PCR S10 clone and the rat S10 cDNA clone. Top row: human sequence, the numbering is given according to the rat S10 nucleotide sequence. The bottom row outlines differences in the rat sequence (overall homology: 90.7%).

FIG. 7: Comparison of deduced amino acid sequences between the Human S10 PCR clone and the rat S10 cDNA clone. Top row: human S10 sequence, the numbering is given according to the rat S10 amino acid sequence. The bottom row outlines differences in the rat sequence (overall homology: 92.3%).

Figures 11A, 11B:
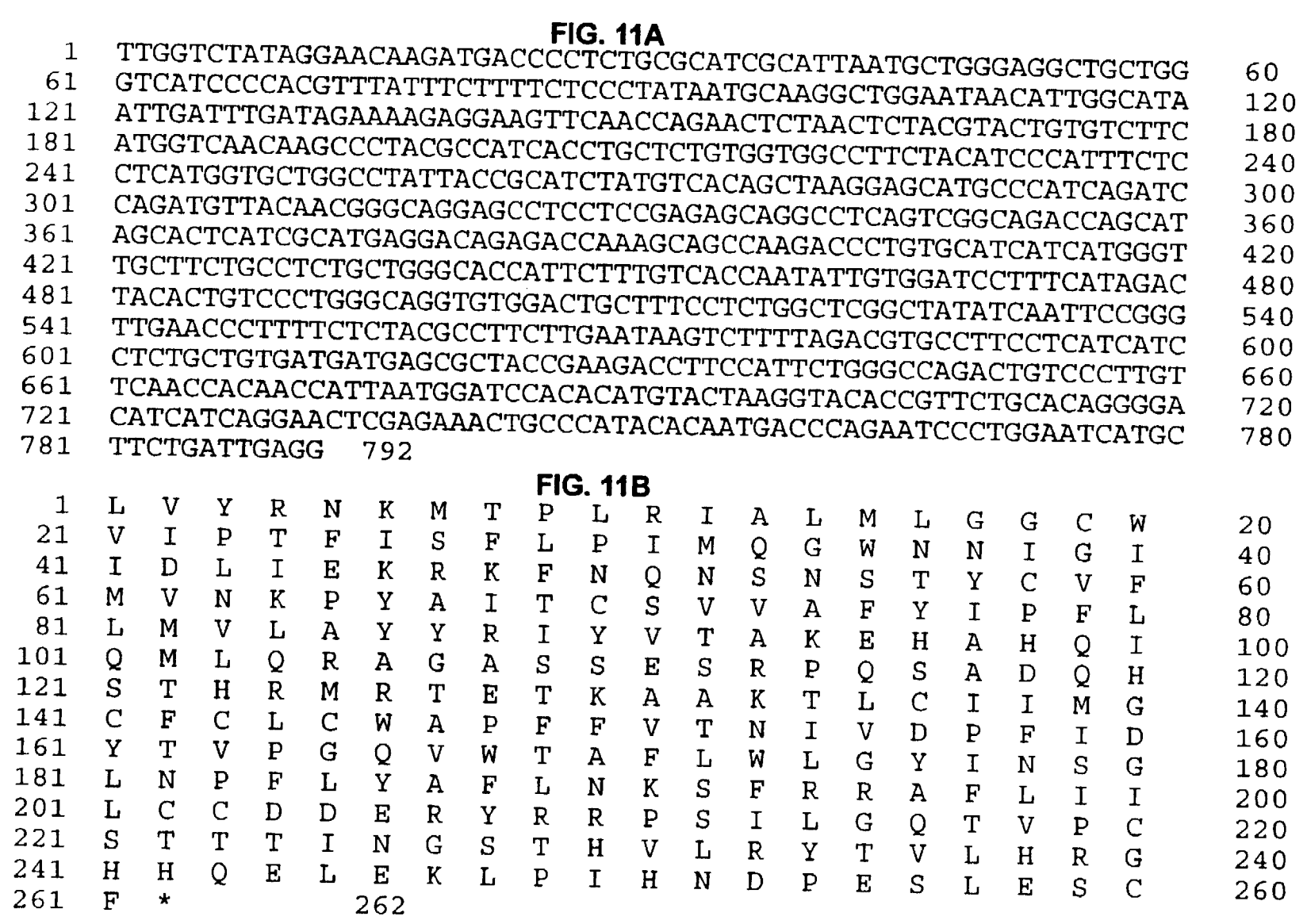

FIG. 11A: Nucleotide sequence of the partial human S10-87 clone. Only partial 3' untranslated sequences are shown (SEQ. ID NO. 14).

FIG. 11B: Deduced amino acid sequence encoded by the nucleotide sequence of FIG. 11A of the partial human S10-87 clone (SEQ. ID NO. 15).

FIGS. 12-1 to 12-3: Comparison of the nucleotide sequences between the human (top row) and the rat S10-87 (bottom row) cDNA clones. The overall identity is 90.8%.

FIG. 13: Comparison of the deduced amino acid sequences between the human (top row) and the rat (bottom row) S10-87 receptors. The overall identity is 93.9%.

FIG. 14A: Nucleotide sequence of the full length human S10-95 clone (SEQ. ID NO. 7).

FIG. 14B: Deduced amino acid sequence encoded by the nucleotide sequence of FIG. 14A (SEQ. ID NO. 8).

FIGS. 15-1 to 15-4: Comparison of the nucleotide sequences between the human (top row) and the rat (bottom row) S10-95 cDNA clones. The overall identity is 90.7%.

FIGS. 16-1 to 16-2: Comparison of the deduced amino acid sequences between the human (top row) and the rat (bottom row) S10-95 receptors. The overall identity is 93.8%.

FIGS. 17-1 to 17-3: Comparison of the nucleotide sequences corresponding to the available coding regions between the two human isoforms (top row S10-95; bottom row S10-87) of the 5-HT$_4$ receptor. The overall identity is 92%.

FIG. 18: Comparison of the deduced amino acid sequences between the two human isoforms (top row S10-95; bottom row S10-87) of the 5-HT$_4$ receptor. The overall identity is 90%.

DETAILED DESCRIPTION OF THE INVENTION

Figure 8:
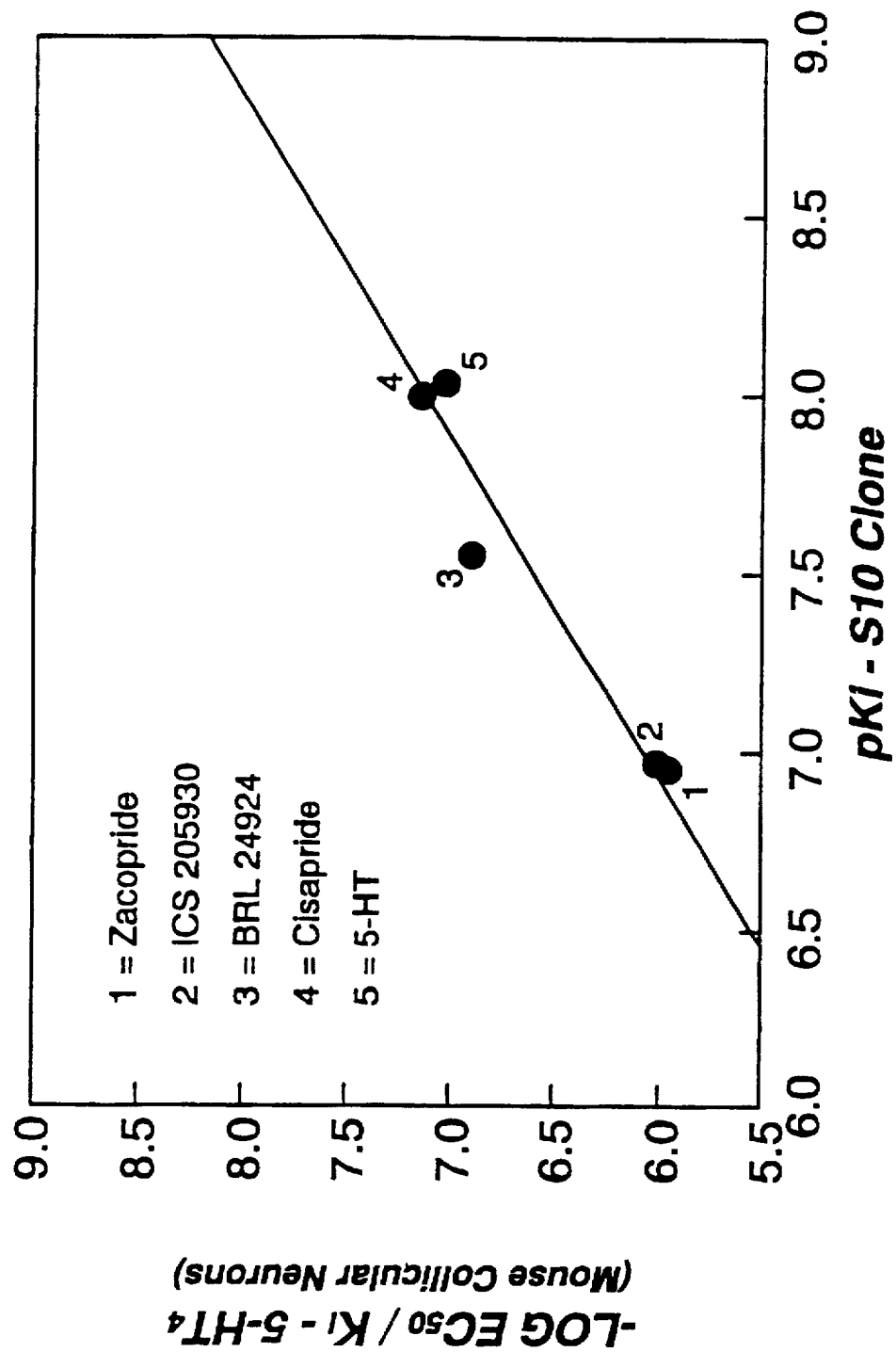
FIG. 8: comparison of binding affinities of key compounds at the S10 clone with adenylate cyclase functional responses obtained with mouse collicular neurons. A correlation plot was constructed between affinity constants of drugs for the S10 receptor with those obtained at a pharmacologically defined 5-HT$_4$ receptor. Binding values for the correlation were taken from table 1 and were expressed as the negative logarithm. Functional data were taken from Dumuis et al. (1988). The correlation coefficient calculated by linear regression was 0.96 indicating that the rank order of potency for the compounds was similar in both preparations.

This invention provides an isolated nucleic acid molecule encoding a mammalian 5-HT$_4$ receptor. This invention further provides an isolated nucleic acid molecule encoding a human 5-HT$_4$ receptor. As used herein, the term "isolated nucleic acid molecule" means a non-naturally occurring nucleic acid molecule that is, a molecule in a form which does not occur in nature. Examples of such an isolated nucleic acid molecule are an RNA, cDNA, or isolated genomic DNA molecule encoding a mammalian 5-HT$_4$ receptor or a human 5-HT$_4$ receptor. As used herein, "5-HT$_4$ receptor" means a molecule which, under physiologic conditions, is substantially specific for the neurotransmitter serotonin, is saturable, of high affinity for serotonin and the activation of which is coupled to the activation of adenylate cyclase and the "5-HT$_4$ receptor" is also sensitive to benzamide derivatives which act as agonists and partial agonists at this receptor subtype. One embodiment of this invention is an isolated nucleic acid molecule encoding a mammalian 5-HT$_4$ receptor. Such a molecule may have coding sequences substantially the same as the coding sequences shown in FIGS. 1 and 2 and 5 (SEQ ID NOs. 1, 3 and 5). A preferred embodiment is an isolated nucleic acid molecule encoding a human 5-HT$_4$ receptor. Such a molecule may have a coding sequence substantially the same as the coding sequence shown in FIG. 5 (SEQ ID NO. 5). The DNA molecules of FIGS. 1, 2 and 5 (Seq ID NOs. 1, 3 and 5) encode the sequence of mammalian 5-HT$_4$ receptors. The DNA molecule of FIG. 5 (Seq ID No. 5) encodes a human 5-HT$_4$ receptor. This invention further provides isolated DNA molecules encoding mammalian 5-HT$_4$ receptors having the sequence H$_2$N—Y—X—COOH wherein Y is the amino acid sequence beginning at amino acid 1 and ending at amino acid 359 of FIG. 1 (SEQ ID NOs. 1 and 2) and wherein X is an amino acid sequence encoding the carboxy terminal region of the receptor. The nucleic acid molecules of FIGS. 1 and 2 ( SEQ ID NOs 1–4) encode 5-HT$_4$ receptors having an identical sequence Y and differing only in their carboxy terminal region X beginning at amino acid 360. one means of isolating a nucleic acid molecule encoding a mammalian 5-HT$_4$ receptor is to probe a mammalian genomic library with a natural or artificially designed DNA probe, using methods well known in the art. In the preferred embodiment of this invention, the mammalian 5-HT$_4$ receptor is a human protein and the nucleic acid molecule encoding the human 5-HT$_4$ receptor is isolated from human cDNA. Degenerate oligonucleotide primers derived from transmembrane (TM) domains of 5-HT$_{1A}$, 5-HT$_{1C}$, 5-HT$_2$ and 5-HT$_{1D\alpha/\beta}$ receptors are useful for identifying cDNA containing a nucleic acid molecule encoding a 5-HT$_4$ receptor, obtaining a probe specific to a mammalian 5-HT$_4$ receptor and for isolating a nucleic acid molecule encoding a mammalian 5-HT$_4$ receptor.

DNA and cDNA molecules which encode a mammalian 5-HT$_4$ receptor are used to obtain complementary genomic DNA, cDNA or RNA from human, mammalian or other animal sources, or to isolate related cDNA or genomic clones by the screening of cDNA or genomic libraries, by methods described in more detail below. Transcriptional regulatory elements from the 5' untranslated region of the isolated clone, and other stability, processing, transcription, translation, and tissue specificity determining regions from the 3' and 5' untranslated regions of the isolated gene are thereby obtained.

This invention provides an isolated nucleic acid molecule which has a nucleic acid sequence which differs from the sequence of a nucleic acid molecule encoding a 5-$HT_4$ receptor at one or more nucleotides and which does not encode a protein having 5-$HT_4$ receptor activity. As used herein, "5-$HT_4$ receptor activity" means the capability of receptor to specifically bind the neurotransmitter, serotonin under physiological conditions and the capability of the receptor to activate adenylate cyclase when the receptor is coupled to adenylate cyclase. An example of a isolated nucleic acid molecule provided by this invention is a nucleic acid molecule which has an in-frame stop codon inserted into the coding sequence such that the transcribed RNA is not translated into protein.

This invention further provides a cDNA molecule encoding a mammalian 5-$HT_4$ receptor, wherein the cDNA molecule has a coding sequence substantially the same as the coding sequence shown in FIGS. 1, 2 and 5 (Seq ID NOs. 1, 3 and 5). This invention provides a cDNA molecule encoding a human 5-$HT_4$ receptor, wherein the cDNA molecule has a coding sequence substantially the same as the coding sequence shown in FIG. 5 (SEQ ID NO. 5). These molecules and their equivalents were obtained by the means described above.

This invention also provides an isolated protein which is a mammalian 5-$HT_4$ receptor. In a preferred embodiment of this invention, the protein is a human 5-$HT_4$ receptor protein having an amino acid sequence substantially similar to the amino acid sequence shown in FIGS. 1, 2 and 5 (SEQ ID Nos. 1–6). In another embodiment of this invention, the protein is a murine 5-$HT_4$ receptor protein having an amino acid sequence substantially similar to the amino acid sequence shown in FIGS. 1, 2 and 5 (SEQ ID NOs. 1–6). As used herein, the term "isolated protein" is intended to encompass a protein molecule free of other cellular components. One means for obtaining an isolated mammalian 5-$HT_4$ receptor protein is to express DNA encoding the 5-$HT_4$ receptor in a suitable host, such as a bacterial, yeast, insect, or mammalian cell, using methods well known to those skilled in the art, and recovering the receptor protein after it has been expressed in such a host, again using methods well known in the art. The receptor may also be isolated from cells which express it, in particular from cells which have been transfected with the expression vectors described below in more detail.

This invention provides a vector comprising DNA, RNA, or cDNA, encoding a mammalian 5-$HT_4$ receptor. This invention further provides a vector comprising DNA, RNA, or cDNA, encoding a human 5-$HT_4$ receptor. Examples of vectors are viruses such as bacteriophages (such as phage lambda), cosmids, plasmids (such as pUC18, available from Pharmacia, Piscataway, N.J.), and other recombination vectors. Nucleic acid molecules are inserted into vector genomes by methods well known to those skilled in the art. Examples of such plasmids are plasmids comprising DNA having a coding sequence substantially the same as the coding sequence shown in FIGS. 1, 2 and 5 (SEQ ID NOs. 1, 3 and 5) and designated pcEXV-S10-87 (ATCC Accession No. 75390), pcEXV-S10-95 (ATCC Accession No. 75391) and pBLuescript-hS10 (ATCC No. 75392).

Alternatively, to obtain these vectors, insert and vector DNA can both be exposed to a restriction enzyme to create complementary ends on both molecules which base pair with each other and are then ligated together with a ligase. Alternatively, linkers can be ligated to the insert DNA which correspond to a restriction site in the vector DNA, which is then digested with the restriction enzyme which cuts at that site. Other means are also available.

This invention also provides vectors comprising a DNA or cDNA encoding a mammalian 5-$HT_4$ receptor and vectors comprising a DNA or cDNA encoding a human 5-$HT_4$ receptor, adapted for expression in a bacterial cell, a yeast cell, insect cell or a mammalian cell which additionally comprise the regulatory elements necessary for expression of the DNA or cDNA encoding a mammalian 5-$HT_4$ receptor or the DNA or cDNA encoding a human 5-$HT_4$ receptor in the bacterial, yeast, insect or mammalian cells operatively linked to the DNA or cDNA encoding the 5-$HT_4$ receptor as to permit expression thereof. DNA or cDNA having coding sequence substantially the same as the coding sequence shown in FIGS. 1 and 2 (SEQ ID NOs. 1 and 3) may be usefully inserted into these vectors to express a mammalian 5-$HT_4$ receptor. DNA or cDNA having a coding sequence substantially the same as the coding sequence shown in FIG. 5 (SEQ ID NO. 5) may be usefully inserted into these vectors to express the human 5-$HT_4$ receptor. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Maniatis, et al., 1982). Similarly, a eukaryotic expression vector includes a heterologous or homologous promoter for RNA polymerase II, a downstream polyadenylation signal, the start codon AUG, and a termination codon for detachment of the ribosome. Furthermore, an insect expression vector, such as recombinant Baculovirus, uses the polyhedrin gene expression signals for expression of the inserted gene in insect cells. Such vectors may be obtained commercially or assembled from the sequences described by methods well known in the art, for example the methods described above for constructing vectors in general. Expression vectors are useful to produce cells that express receptors. Certain uses for such cells are described in more detail below.

In one embodiment of this invention a plasmid is adapted for expression in a bacterial, yeast, insect, or, in particular, a mammalian cell wherein the plasmid comprises DNA or cDNA encoding a mammalian 5-$HT_4$ receptor or DNA or cDNA encoding a human 5-$HT_4$ receptor and the regulatory elements necessary for expression of the DNA in the bacterial, yeast, insect, or mammalian cell operatively linked to the DNA or cDNA encoding a mammalian 5-$HT_4$ receptor or to the DNA or cDNA encoding a human 5-$HT_4$ receptor as to permit expression thereof. Suitable plasmids may include, but are not limited to plasmids adapted for expression in a mammalian cell, e.g., EVJB, EXV-3. An example of such a plasmid adapted for expression in a mammalian cell is a plasmid comprising cDNA having coding sequences substantially the same as the coding sequence shown in FIGS. 1, 2 and 5 (SEQ ID NOs. 1, 3 and 5) and the regulatory elements necessary for expression of the DNA in the mammalian cell. These plasmids have been designated pcEXV-S10-87 deposited under ATCC Accession No. 75390, pcEXV-S10-95 deposited under ATCC Accession No. 75391, and pBluescript-hS10, deposited under ATCC Accession No 75392. Those skilled in the art will readily appreciate that numerous plasmids adapted for expression in a mammalian cell which comprise DNA encoding a mammalian or human 5-HT$_4$ receptor and the regulatory elements necessary to express such DNA in the mammalian cell may be constructed utilizing existing plasmids and adapted as appropriate to contain the regulatory elements necessary to express the DNA in the mammalian cell. The plasmids may be constructed by the methods described above for expression vectors and vectors in general, and by other methods well known in the art.

Deposit discussed supra were made pursuant to, and in satisfaction of, the provisions of the Budapest Treaty on the International Recognition of the Deposit of Microorganisms for the Purpose of Patent Procedure with the American Type Culture Collection (ATCC), 12301 Parklawn Drive, Rockville, Md. 20852.

This invention provides a mammalian cell comprising a DNA or cDNA molecule encoding a mammalian 5-HT$_4$ receptor, such as a mammalian cell comprising a plasmid adapted for expression in a mammalian cell, said plasmid further comprises DNA or cDNA encoding a mammalian 5-HT$_4$ receptor and the regulatory elements necessary for expression of the DNA or cDNA in the mammalian cell operatively linked to the DNA or cDNA encoding a mammalian 5-HT$_4$ receptor as to permit expression thereof. This invention provides a mammalian cell comprising a DNA or cDNA molecule encoding a human 5-HT$_4$ receptor, such as a mammalian cell comprising a plasmid adapted for expression in a mammalian cell, said plasmid further comprises a DNA or cDNA molecule encoding a human 5-HT$_4$ receptor and the regulatory elements necessary for expression of the DNA or cDNA in the mammalian cell operatively linked to the DNA or cDNA encoding a human 5-HT$_4$ receptor as to permit expression thereof. Numerous mammalian cells may be used as hosts, including, but not limited to, the mouse fibroblast cell NIH3T3, CHO cells, HeLa cells, LM (tk–) cells, Cos-7 cells, etc. Expression plasmids such as that described supra may be used to transfect mammalian cells by methods well known in the art such as calcium phosphate precipitation, or DNA or cDNA encoding a human or mammalian 5-HT$_4$ receptor may be otherwise introduced into mammalian cells, e.g., by microinjection, to obtain mammalian cells which comprise DNA, e.g., cDNA or a plasmid, encoding a human or mammalian 5-HT$_4$ receptor.

This invention provides a nucleic acid probe comprising a nucleic acid molecule of at least 15 nucleotides capable of specifically hybridizing with an unique sequence included within the sequence of a nucleic acid molecule encoding a human 5-HT$_4$ receptor, for example with a coding sequence included within the sequences shown in FIG. 5 (SEQ ID NO. 5). This invention further provides a nucleic acid probe comprising a nucleic acid molecule of at least 15 nucleotides capable of specifically hybridizing with a sequence included within the sequence of a nucleic acid molecule encoding a mammalian 5-HT$_4$ receptor, for example with a coding sequence included within the sequences shown in FIG. 1 and FIG. 2 (SEQ ID NOs. 1 and 3) As used herein, the phrase "specifically hybridizing" means the ability of a nucleic acid molecule to recognize a nucleic acid sequence complementary to its own and to form double-helical segments through hydrogen bonding between complementary base pairs. As used herein, the phrase "unique sequence" means a nucleic acid molecule sequence specific to only the nucleic acid molecule encoding a mammalian 5-HT$_4$ receptor. Nucleic acid probe technology is well known to those skilled in the art who will readily appreciate that such probes may vary greatly in length and may be labeled with a detectable label, such as a radioisotope or fluorescent dye, to facilitate detection of the probe. Detection of nucleic acid encoding a human 5-HT$_4$ receptor is useful as a diagnostic test for any disease process in which levels of expression of the 5-HT$_4$ receptor are altered. DNA probe molecules are produced by insertion of a DNA molecule which encodes a 5-HT$_4$ receptor or fragments thereof into suitable vectors, such as plasmids or bacteriophages, followed by insertion into suitable bacterial host cells and replication and harvesting of the DNA probes, all using methods well known in the art. For example, the DNA may be extracted from a cell lysate using phenol and ethanol, digested with restriction enzymes corresponding to the insertion sites of the DNA into the vector (discussed above), electrophoresed, and cut out of the resulting gel. An example of such DNA molecules is shown in FIGS. 1, 2 and 5 (SEQ ID Nos. 1, 3, and 5)>The probes are useful for 'in situ' hybridization or in order to locate tissues which express this gene family, or for other hybridization assays for the presence of these genes or their mRNA in various biological tissues. In addition, synthesized oligonucleotides (produced by a DNA synthesizer) complementary to the sequence of a DNA molecule which encode a mammalian 5-HT$_4$ receptor or complementary to the sequence of a DNA molecule which encodes a human 5-HT$_4$ receptor are useful as probes for these genes, for their associated mRNA, or for the isolation of related genes by homology screening of genomic or cDNA libraries, or by the use of amplification techniques such as the polymerase chain reaction.

This invention also provides a method of detecting expression of a human 5-HT$_4$ receptor on the surface of a cell by detecting the presence of mRNA coding for a 5-HT$_4$ receptor. This invention further provides a method of detecting expression of a mammalian 5-HT$_4$ receptor on the surface of the cell by detecting the presence of mRNA coding for a mammalian 5-HT$_4$ receptor. These methods comprise obtaining total mRNA from the cell using methods well known in the art and contacting the mRNA so obtained with a nucleic acid probe as described hereinabove, under hybridizing conditions, detecting the presence of mRNA hybridized to the probe, and thereby detecting the expression of the receptor by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules (Maniatis et al., 1982). The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those skilled in the art, and the discussion above is merely an example.

This invention provides an antisense oligonucleotide having a sequence capable of binding specifically with any sequences of an mRNA molecule which encodes a human 5-HT$_4$ receptor so as to prevent translation of the human 5-HT$_4$ receptor. The antisense oligonucleotide may have a sequence capable of binding specifically with any sequences of the cDNA molecule whose sequence is shown in FIG. 5 (SEQ ID NO. 5). This invention also provides an antisense oligonucleotide having a sequence capable of binding specifically with any sequences of an mRNA molecule which encodes a mammalian 5-HT$_4$ receptor so as to prevent translation of the mammalian 5-HT$_4$ receptor. The antisense oligonucleotide may have a sequence capable of binding specifically with any sequences of the cDNA molecule whose sequence is shown in FIGS. 1 and 2 (SEQ ID NOs. 1 and 3). As used herein, the phrase "binding specifically" means the ability of an antisense oligonucleotide to recognize a nucleic acid sequence complementary to its own and to form double-helical segments through hydrogen bonding between complementary base pairs. A particular example of an antisense oligonucleotide is an antisense oligonucleotide comprising chemical analogues of nucleotides.

This invention also provides a pharmaceutical composition comprising an effective amount of the oligonucleotide described above effective to reduce expression of a human 5-$HT_4$ receptor by passing through a cell membrane and binding specifically with mRNA encoding the 5-$HT_4$ receptor in the cell so as to prevent its translation and a pharmaceutically acceptable hydrophobic carrier capable of passing through a cell membrane. This invention further provides a pharmaceutical composition comprising an effective amount of the oligonucleotide described above effective to reduce expression of a mammalian 5-$HT_4$ receptor by passing through a cell membrane and binding specifically with mRNA encoding a mammalian 5-$HT_4$ receptor in the cell so as to prevent its translation and a pharmaceutically acceptable hydrophobic carrier capable of passing through a cell membrane. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The oligonucleotide may be coupled to a substance which inactivates mRNA, such as a ribozyme. The pharmaceutically acceptable hydrophobic carrier capable of passing through cell membranes may also comprise a structure which binds to a transporter specific for a selected cell type and is thereby taken up by cells of the selected cell type. The structure may be part of a protein known to bind a cell-type specific transporter, for example an insulin molecule, which would target pancreatic cells. DNA molecules having a coding sequence substantially the same as the coding sequences shown in FIG. 5 (SEQ ID No. 5) may be used as the oligonucleotides of the pharmaceutical composition.

This invention also provides a pharmaceutical composition comprising an effective amount of the oligonucleotide described above effective to reduce expression of a mammalian 5-$HT_4$ receptor by passing through a cell membrane and binding specifically with mRNA encoding the 5-$HT_4$ receptor in the cell so as to prevent its translation and a pharmaceutically acceptable hydrophobic carrier capable of passing through a cell membrane. DNA molecules having a coding sequence substantially the same as the coding sequences shown in FIGS. 1 and 2 (SEQ ID NOs. 1 and 3) may be used as the oligonucleotides of the pharmaceutical composition.

This invention provides a method of treating abnormalities which are alleviated by reduction of expression of 5-$HT_4$ receptor. This method comprises administering to a subject an effective amount of the pharmaceutical composition described above effective to reduce expression of the 5-$HT_4$ receptor by the subject. This invention further provides a method of treating an abnormal condition related to 5-$HT_4$ receptor activity which comprises administering to a subject an amount of the pharmaceutical composition described above effective to reduce expression of the 5-$HT_4$ receptor by the subject. Examples of such abnormal conditions are irritable bowel disease, postoperative ileus, diabetic gastroparesis, emesis, achalasia, hiatal hernia, esophageal spasm and other diseases of the gastrointestinal tract, as well as in cardiac, urinary, and endocrine function.

Antisense oligonucleotide drugs inhibit translation of mRNA encoding 5-$HT_4$ receptor. Synthetic antisense oligonucleotides, or other antisense chemical structures are designed to bind to mRNA encoding the 5-$HT_4$ receptor and inhibit translation of mRNA and are useful as drugs to inhibit expression of 5-$HT_4$ receptor genes in patients. This invention provides a means to therapeutically alter levels of expression of a human or mammalian 5-$HT_4$ receptor by the use of a synthetic antisense oligonucleotide drug (SAOD) which inhibits translation of mRNA encoding the 5-$HT_4$ receptor. Synthetic antisense oligonucleotides, or other antisense chemical structures designed to recognize and selectively bind to mRNA, are constructed to be complementary to portions of the nucleotide sequence shown in FIGS. 1, 2 and 5 (SEQ ID NOs. 1, 3 and 5) of DNA, RNA or of chemically modified, artificial nucleic acids. The SAOD is designed to be stable in the blood stream for administration to patients by injection, or in laboratory cell culture conditions, for administration to cells removed from the patient. The SAOD is designed to be capable of passing through cell membranes in order to enter the cytoplasm of the cell by virtue of physical and chemical properties of the SAOD which render it capable of passing through cell membranes (e.g., by designing small, hydrophobic SAOD chemical structures) or by virtue of specific transport systems in the cell which recognize and transport the SAOD into the cell. In addition, the SAOD can be designed for administration only to certain selected cell populations by targeting the SAOD to be recognized by specific cellular uptake mechanisms which bind and take up the SAOD only within certain selected cell populations. For example, the SAOD may be designed to bind to transporter found only in a certain cell type, as discussed above. The SAOD is also designed to recognize and selectively bind to the target mRNA sequence, which may correspond to a sequence contained within the sequence shown in FIGS. 1, 2 and 5 (SEQ ID NOs. 1, 3, and 5) by virtue of complementary base pairing to the mRNA. Finally, the SAOD is designed to inactivate the target mRNA sequence by any of three mechanisms: 1) by binding to the target mRNA and thus inducing degradation of the mRNA by intrinsic cellular mechanisms such as RNAse I digestion, 2) by inhibiting translation of the mRNA target by interfering with the binding of translation-regulating factors or of ribosomes, or 3) by inclusion of other chemical structures, such as ribozyme sequences or reactive chemical groups, which either degrade or chemically modify the target mRNA. Synthetic antisense oligonucleotide drugs have been shown to be capable of the properties described above when directed against mRNA targets (Cohen, J. S., 1989; Weintraub, H. M., 1990). In addition, coupling of ribozymes to antisense oligonucleotides is a promising strategy for inactivating target mRNA (N. Sarver et al., 1990). An SAOD serves as an effective therapeutic agent if it is designed to be administered to a patient by injection, or if the patient's target cells are removed, treated with the SAOD in the laboratory, and replaced in the patient. In this manner, an SAOD serves as a therapy to reduce 5-$HT_4$ receptor expression in particular target cells of a patient, in any clinical condition which may benefit from reduced expression of 5-$HT_4$ receptor.

This invention provides an antibody directed to the human 5-$HT_4$ receptor. This invention also provides an antibody directed to the mammalian 5-$HT_4$ receptor. This antibody may comprise, for example, a monoclonal antibody directed to an epitope of a human 5-$HT_4$ receptor present on the surface of a cell, the epitope having an amino acid sequence substantially the same as an amino acid sequence for a cell surface epitope of the human 5-HT$_4$ receptor included in the amino acid sequence shown in FIG. 5. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer which forms the cell membrane, while hydrophilic regions are located on the cell surface, in an aqueous environment. Therefore antibodies to the hydrophilic amino acid sequences shown in FIG. 5 will bind to a surface epitope of a 5-HT$_4$ receptor as described. Antibodies directed to a human or mammalian 5-HT$_4$ receptor may be serum-derived or monoclonal and are prepared using methods well known in the art. For example, monoclonal antibodies are prepared using hybridoma technology by fusing antibody producing B cells from immunized animals with myeloma cells and selecting the resulting hybridoma cell line producing the desired antibody. Cells such as NIH3T3 cells or LM (tk$^-$) cells may be used as immunogens to raise such an antibody. Alternatively, synthetic peptides may be prepared using commercially available machines and the amino acid sequence shown in FIGS. 1, 2, and 5 (SEQ ID NOs. 1–6). As a still further alternative, DNA, such as a cDNA or a fragment thereof, may be cloned and expressed and the resulting polypeptide recovered and used as an immunogen. These antibodies are useful to detect the presence of 5-HT$_4$ receptor encoded by the isolated DNA, or to inhibit the function of the 5-HT$_4$ receptor in living animals, in humans, or in biological tissues or fluids isolated from animals or humans.

This invention also provides a pharmaceutical composition which comprises an effective amount of an antibody directed to an epitope of the human 5-HT$_4$ receptor, effective to block binding of naturally occurring substrates to the 5-HT$_4$ receptor, and a pharmaceutically acceptable carrier. A monoclonal antibody directed to an epitope of a human 5-HT$_4$ receptor present on the surface of a cell which has an amino acid sequence substantially the same as an amino acid sequence for a cell surface epitope of the human 5-HT$_4$ receptor included in the amino acid sequence shown in FIG. 5 (SEQ ID NOs. 5 and 6) is useful for this purpose.

This invention also provides a pharmaceutical composition which comprises an effective amount of an antibody directed to an epitope of a mammalian 5-HT$_4$ receptor, effective to block binding of naturally occurring substrates to the 5-HT$_4$ receptor, and a pharmaceutically acceptable carrier. A monoclonal antibody directed to an epitope of a mammalian 5-HT$_4$ receptor present on the surface of a cell which has an amino acid sequence substantially the same as an amino acid sequence for a cell surface epitope of a mammalian 5-HT$_4$ receptor included in the amino acid sequence shown in FIGS. 1 and 2 (SEQ ID NOs. 1–4) is useful for this purpose.

This invention also provides a method of treating abnormalities in a subject which are alleviated by reduction of expression of a human or mammalian 5-HT$_4$ receptor which comprises administering to the subject an effective amount of the pharmaceutical composition described above effective to block binding of naturally occurring substrates to the receptor and thereby alleviate abnormalities resulting from overexpression of a human or mammalian 5-HT$_4$ receptor. Binding of the antibody to the receptor prevents the receptor from functioning, thereby neutralizing the effects of overexpression. The monoclonal antibodies described above are useful for this purpose. This invention additionally provides a method of treating an abnormal condition related to an excess of 5-HT$_4$ receptor activity which comprises administering to a subject an amount of the pharmaceutical composition described above effective to block binding of naturally occurring substrates to the 5-HT$_4$ receptor and thereby alleviate the abnormal condition. Some examples of abnormal conditions associated with excess 5-HT$_4$ receptor activity are irritable bowel disease, postoperative ileus, diabetic gastroparesis, emesis, achalasia, hiatal hernia, esophageal spasm and other diseases of the gastrointestinal tract, as well as in cardiac, urinary, and endocrine function.

This invention provides methods of detecting the presence of a 5-HT$_4$ receptor on the surface of a cell which comprises contacting the cell with an antibody directed to the 5-HT$_4$ receptor, under conditions permitting binding of the antibody to the receptor, detecting the presence of the antibody bound to the cell, and thereby the presence of the 5-HT$_4$ receptor on the surface of the cell. Such methods are useful for determining whether a given cell is defective in expression of 5-HT$_4$ receptors. Bound antibodies are detected by methods well known in the art, for example by binding fluorescent markers to the antibodies and examining the cell sample under a fluorescence microscope to detect fluorescence on a cell indicative of antibody binding. The monoclonal antibodies described above are useful for this purpose.

This invention provides a transgenic nonhuman mammal expressing DNA encoding a human 5-HT$_4$ receptor and a transgenic nonhuman mammal expressing DNA encoding a mammalian 5-HT receptor. This invention also provides a transgenic nonhuman mammal expressing DNA encoding a human or mammalian 5-HT$_4$ receptor so mutated as to be incapable of normal receptor activity, and not expressing native 5-HT$_4$ receptor. This invention further provides a transgenic nonhuman mammal whose genome comprises DNA encoding a human 5-HT$_4$ receptor so placed as to be transcribed into antisense mRNA which is complementary to mRNA encoding a human 5-HT$_4$ receptor and which hybridizes to mRNA encoding a 5-HT$_4$ receptor thereby reducing its translation and a transgenic nonhuman mammal whose genome comprises DNA encoding a mammalian 5-HT$_4$ receptor so placed as to be transcribed into antisense mRNA which is complementary to mRNA encoding a mammalian 5-HT$_4$ receptor and which hybridizes to mRNA encoding a mammalian 5-HT$_4$ receptor thereby reducing its translation. The DNA may additionally comprise an inducible promoter or additionally comprise tissue specific regulatory elements, so that expression can be induced, or restricted to specific cell types. Examples of DNA are DNA or cDNA molecules having a coding sequence substantially the same as the coding sequences shown in FIGS. 1, 2 and 5 (SEQ ID NOs. 1, 3, and 5). An example of a transqenic animal is a transgenic mouse. Examples of tissue specificity-determining regions are the metallothionein promotor (Low et al., 1986) and the L7 promotor (Oberdick et al., 1990).

Animal model systems which elucidate the physiological and behavioral roles of mammalian receptors are produced by creating transgenic animals in which the expression of a receptor is either increased or decreased, or the amino acid sequence of the expressed receptor protein is altered, by a variety of techniques. Examples of these techniques include, but are not limited to: 1) Insertion of normal or mutant versions of DNA encoding a human 5-HT$_4$ receptor or homologous animal versions of this gene, by microinjection, retroviral infection or other means well known to those skilled in the art, into appropriate fertilized embryos in order to produce a transgenic animal (Hogan et al., 1986) or, 2) Homologous recombination (Capecchi M. R., 1989; Zimmer A. and Gruss, P., 1989) of mutant or normal, human or animal versions of these genes with the native gene locus in transgenic animals to alter the regulation of expression or the structure of the receptor. The technique of homologous recombination is well known in the art. It replaces the native gene with the inserted gene and so is useful for producing an animal that cannot express native receptor but does express, for example, an inserted mutant receptor, which has replaced the native receptor in the animal's genome by recombination, resulting in underexpression of the receptor. Microinjection adds genes to the genome, but does not remove them, and so is useful for producing an animal which expresses its own and added receptors, resulting in overexpression of the receptor.

One means available for producing a transgenic animal, with a mouse as an example, is as follows: Female mice are mated, and the resulting fertilized eggs are dissected out of their oviducts. The eggs are stored in an appropriate medium such as M2 medium (Hogan, B. et al. 1986). DNA or cDNA encoding a receptor is purified from a vector (such as plasmids pcEXV-S10-87, pcEXV-S10-95 and pBluescript-hS10 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of receptor-specific drugs is to activate or to inhibit the receptor, the transgenic animal model systems described above are useful for testing the biological activity of drugs directed against the receptors even before such drugs become available. These animal model systems are useful for predicting or evaluating possible therapeutic applications of drugs which activate or inhibit receptors by inducing or inhibiting expression of the native or trans-gene and thus increasing or decreasing expression of normal or mutant receptors in the living animal. Thus, a model system is produced in which the biological activity of drugs directed against the receptors are evaluated before such drugs become available. The transgenic animals which over or under produce the receptor indicate by their physiological state whether over or under production of the receptor is therapeutically useful.

It is therefore useful to evaluate drug action based on the transgenic model system. One use is based on the fact that it is well known in the art that a drug such as an antidepressant acts by blocking neurotransmitter uptake, and thereby increases the amount of neurotransmitter in the synaptic cleft. The physiological result of this action is to stimulate the production of less receptor by the affected cells, leading eventually to underexpression. Therefore, an animal which underexpresses receptor is useful as a test system to investigate whether the actions of such drugs which result in under expression are in fact therapeutic. Another use is that if overexpression is found to lead to abnormalities, then a drug which down-regulates or acts as an antagonist to the receptor is indicated as worth developing, and if a promising therapeutic application is uncovered by these animal model systems, activation or inhibition of the 5-HT$_4$ receptor is achieved therapeutically either by producing agonist or antagonist drugs directed against the 5-HT$_4$ receptor or by any method which increases or decreases the expression of this receptor in man.

Further provided by this invention is a method of determining the physiological effects of expressing varying levels of human or mammalian 5-HT$_4$ receptors which comprises producing a transgenic nonhuman animal whose levels of human or mammalian 5-HT$_4$ receptor expression are varied by use of an inducible promoter which regulates receptor expression. This invention also provides a method of determining the physiological effects of expressing varying levels of human or mammalian 5-HT$_4$ receptor which comprises producing a panel of transgenic nonhuman animals each expressing a different amount of human or mammalian 5-HT$_4$ receptor. Such animals may be produced by introducing different amounts of DNA encoding a human or mammalian 5-HT$_4$ receptor into the oocytes from which the transgenic animals are developed.

This invention also provides a method for identifying a substance capable of alleviating abnormalities resulting from overexpression of a human or mammalian 5-HT$_4$ receptor comprising administering the substance to a transgenic nonhuman mammal expressing at least one artificially introduced DNA molecule encoding a human or mammalian 5-HT$_4$ receptor and determining whether the substance alleviates the physical and behavioral abnormalities displayed by the transgenic nonhuman mammal as a result of overexpression of a human or mammalian 5-HT$_4$ receptor. As used herein, the term "substance" means a compound or composition which may be natural, synthetic, or a product derived from screening. Examples of DNA molecules are DNA or cDNA molecules having a coding sequence substantially the same as the coding sequences shown in FIGS. 1, 2, and 5 (SEQ ID NOs. 1, 3, and 5).

This invention provides a pharmaceutical composition comprising an amount of the substance described supra effective to alleviate the abnormalities resulting from overexpression of 5-HT$_4$ receptor and a pharmaceutically acceptable carrier.

This invention further provides a method for treating the abnormalities resulting from overexpression of a human or mammalian 5-HT$_4$ receptor which comprises administering to a subject an amount of the pharmaceutical composition described above effective to alleviate the abnormalities resulting from overexpression of a human or mammalian 5-HT$_4$ receptor.

This invention provides a method for identifying a substance capable of alleviating the abnormalities resulting from underexpression of a human or mammalian 5-HT$_4$ receptor comprising administering the substance to the transgenic nonhuman mammal described above which expresses only nonfunctional human or mammalian 5-HT$_4$ receptor and determining whether the substance alleviates the physical and behavioral abnormalities displayed by the transgenic nonhuman mammal as a result of underexpression of a human or mammalian 5-HT$_4$ receptor.

This invention also provides a pharmaceutical composition comprising an amount of a substance effective to alleviate abnormalities resulting from underexpression of a human or mammalian 5-HT$_4$ receptor and a pharmaceutically acceptable carrier.

This invention further provides a method for treating the abnormalities resulting from underexpression of a human or mammalian 5-HT$_4$ receptor which comprises administering to a subject an amount of the pharmaceutical composition described above effective to alleviate the abnormalities resulting from underexpression of a human or mammalian 5-HT$_4$ receptor.

This invention provides a method for diagnosing a predisposition to a disorder associated with the expression of a human or mammalian 5-HT$_4$ receptor allele which comprises: a) obtaining DNA of subjects suffering from the disorder; b) performing a restriction digest of the DNA with a panel of restriction enzymes; c) electrophoretically separating the resulting DNA fragments on a sizing gel; d) contacting the resulting gel with a nucleic acid probe capable of specifically hybridizing to DNA encoding a human or mammalian 5-$HT_4$ receptor and labelled with a detectable marker; e) detecting labelled bands which have hybridized to the DNA encoding a human or mammalian 5-$HT_4$ receptor labelled with a detectable marker to create a unique band pattern specific to the DNA of subjects suffering from the disorder; f) preparing DNA obtained for diagnosis by steps a–e; and g) comparing the unique band pattern specific to the DNA of subjects suffering from the disorder from step e and the DNA obtained for diagnosis from step f to determine whether the patterns are the same or different and thereby to diagnose predisposition to the disorder if the patterns are the same. This method may also be used to diagnose a disorder associated with the expression of a specific human 5-$HT_4$ receptor allele or mammalian 5-$HT_4$ receptor allele.

This invention provides a method of preparing the isolated 5-$HT_4$ receptor which comprises inducing cells to express receptor, recovering the receptor from the resulting cells, and purifying the receptor so recovered. An example of a 5-$HT_4$ receptor is an isolated protein having substantially the same amino acid sequence as the amino acid sequence shown in FIG. 5. For example, cells can be induced to express receptors by exposure to substances such as hormones. The cells can then be homogenized and the receptor isolated from the homogenate using an affinity column comprising, for example serotonin or another substance which is known to bind to the 5-$HT_4$ receptor. The resulting fractions can then be purified by contacting them with an ion exchange column, and determining which fraction contains 5-$HT_4$ receptor activity or binds anti-receptor antibodies.

This invention provides a method of preparing an isolated human 5-$HT_4$ receptor which comprises inserting nucleic acid encoding the human 5-$HT_4$ receptor in a suitable vector, inserting the resulting vector in a suitable host cell, recovering the receptor produced by the resulting cell, and purifying the receptor so recovered. An example of an isolated human 5-$HT_4$ receptor is an isolated protein having substantially the same amino acid sequence as the amino acid sequence shown in FIG. 5 (SEQ ID NOs. 5 and 6). This invention provides a method of preparing an isolated mammalian 5-$HT_4$ receptor which comprises inserting nucleic acid encoding the mammalian 5-$HT_4$ receptor in a suitable vector, inserting the resulting vector in a suitable host cell, recovering the receptor produced by the resulting cell, and purifying the receptor so recovered. An example of an isolated mammalian 5-$HT_4$ receptor is an isolated protein having substantially the same amino acid sequence as the amino acid sequence shown in FIGS. 1 and 2 (SEQ ID NOs. 1–2 and Seq I.D. Nos. 3–4, respectively). These methods for preparing 5-$HT_4$ receptor uses recombinant DNA technology methods well known in the art. For example, isolated nucleic acid encoding 5-$HT_4$ receptor is inserted in a suitable vector, such as an expression vector. A suitable host cell, such as a bacterial cell, insect cell, or a eukaryotic cell such as a yeast cell, is transfected with the vector. 5-$HT_4$ receptor is isolated from the culture medium by affinity purification or by chromatography or other methods well known in the art.

This invention provides a method for determining whether a compound not known to be capable of specifically binding to a human 5-$HT_4$ receptor can specifically bind to the human 5-$HT_4$ receptor, which comprises contacting a mammalian cell comprising a plasmid adapted for expression in a mammalian cell which plasmid further comprises a DNA which expresses a human 5-$HT_4$ receptor on the cell's surface with the compound under conditions permitting binding of ligands known to bind to a human 5-$HT_4$ receptor, detecting the presence of any compound bound to the human 5-$HT_4$ receptor, the presence of bound compound indicating that the compound is capable of specifically binding to the human 5-$HT_4$ receptor.

This invention provides a method for determining whether a compound not known to be capable of specifically binding to a mammalian 5-$HT_4$ receptor can specifically bind to the mammalian 5-$HT_4$ receptor, which comprises contacting a mammalian cell comprising a plasmid adapted for expression in a mammalian cell which plasmid further comprises a DNA which expresses a mammalian 5-$HT_4$ receptor on the cell's surface with the compound under conditions permitting binding of ligands known to bind to a mammalian 5-$HT_4$ receptor, detecting the presence of any compound bound to the human 5-$HT_4$ receptor, the presence of bound compound indicating that the compound is capable of specifically binding to the mammalian 5-$HT_4$ receptor.

This invention provides a method for identifying a compound which is not known to be capable of binding to a human 5-$HT_4$ receptor can functionally activate the human 5-$HT_4$ receptor on the surface of a mammalian cell or prevent a ligand which does so, which comprises contacting the mammalian cell which cell comprises a plasmid adapted for expression in the mammalian cell such plasmid further comprising DNA which expresses the human 5-$HT_4$ receptor on the surface of the mammalian cell with the compound, determining whether the compound activates the human 5-$HT_4$ receptor or prevents a ligand which does so, and thereby identifying the compound as a compound which is binds to and functionally activates the human 5-$HT_4$ receptor or prevents the functional activation of the human 5-$HT_4$ receptor by a ligand which does so.

The DNA in the cell may have a coding sequence substantially the same as the coding sequence shown in FIG. 5 ( SEQ ID No. 5).

This invention provides a method for identifying a compound which is not known to be capable of binding to a mammalian 5-$HT_4$ receptor can functionally activate the mammalian 5-$HT_4$ receptor on the surface of a mammalian cell or prevent a ligand which does so, which comprises contacting the mammalian cell which cell comprises a plasmid adapted for expression in the mammalian cell such plasmid further comprising DNA which expresses the mammalian 5-$HT_4$ receptor on the surface of the mammalian cell with the compound, determining whether the compound activates the mammalian 5-$HT_4$ receptor or prevents a ligand which does so, and thereby identifying the compound as a compound which is binds to and functionally activates the mammalian 5-$HT_4$ receptor or prevents the functional activation of the mammalian 5-$HT_4$ receptor by a ligand which does so. The DNA in the cell may have a coding sequence substantially the same as the coding sequence shown in FIGS. 1 and 2 (SEQ ID NOs. 1 and 3).

The activation or blockade of the functional response is detected by means of a bioassay from the mammalian cell such as a second messenger response, and thereby determining whether the compound activates or prevents the activation of the 5-$HT_4$ receptor functional output. Preferably, the mammalian cell is nonneuronal in origin. An example of a nonneuronal mammalian cell is an LM (tk–) cell. Another example of a non-neuronal mammalian cell to be used for functional assays is a murine fibroblast cell line, specifically the NIH3T3 cell. The preferred method for determining whether a compound is capable of binding to the 5-$HT_4$ receptor comprises contacting a transfected non-neuronal mammalian cell (i.e. a cell that does not naturally express any type of 5-HT or G-protein coupled receptor, thus will only express such a receptor if it is transfected into the cell) expressing a 5-HT$_4$ receptor on its surface, or contacting a membrane preparation derived from such a transfected cell, with the compound under conditions which are known to prevail, and thus to be associated with, in vivo binding of ligands to a 5-HT$_4$ receptor, detecting the presence of any of the compound being tested bound to the 5-HT$_4$ receptor on the surface of the cell, and thereby determining whether the compound binds to, and activates or prevents the activation of the 5-HT$_4$ receptor. This response system is obtained by transfection of isolated DNA into a suitable host cell containing the desired second messenger system such as phosphoinositide hydrolysis, adenylate cyclase, guanylate cyclase or ion channels. Such a host system is isolated from pre-existing cell lines, or can be generated by inserting appropriate components of second messenger systems into existing cell lines. Such a transfection system provides a complete response system for investigation or assay of the activity of human 5-HT$_4$ receptor with compounds as described above.

Transfection systems are useful as living cell cultures for competitive binding assays between known or candidate drugs and ligands which bind to the receptor and which are labeled by radioactive, spectroscopic or other reagents. Membrane preparations containing the receptor isolated from transfected cells are also useful for these competitive binding assays. Functional assays of second messenger systems or their sequelae in transfection systems act as assays for binding affinity and efficacy in the activation of receptor function. A transfection system constitutes a "drug discovery system" useful for the identification of natural or synthetic compounds with potential for drug development that can be further modified or used directly as therapeutic compounds to activate or inhibit the natural functions of the human 5-HT$_4$ receptor. The transfection system is also useful for determining the affinity and efficacy of known drugs at human 5-HT$_4$ receptor sites.

This invention also provides a method of screening compounds to identify drugs which interact with, and specifically bind to, a human 5-HT$_4$ receptor on the surface of a cell, which comprises contacting a mammalian cell which comprises a plasmid adapted for expression in a mammalian cell which plasmid further comprises DNA which expresses a human 5-HT$_4$ receptor on the cell's surface with a plurality of compounds, determining those compounds which bind to the human 5-HT$_4$ receptor expressed on the cell surface of the mammalian cell, and thereby identifying compounds which interact with, and specifically bind to, the human 5-HT$_4$ receptor. The DNA in the cell may have a coding sequence substantially the same as the coding sequence shown in FIG. 5 (SEQ ID NO. 5). This invention also provides a method of screening compounds to identify drugs which interact with, and specifically bind to, a mammalian 5-HT$_4$ receptor on the surface of a cell, which comprises contacting a mammalian cell which comprises a plasmid adapted for expression in a mammalian cell which plasmid further comprises DNA which expresses a mammalian 5-HT$_4$ receptor on the cell's surface with a plurality of compounds, determining those compounds which bind to the mammalian 5-HT$_4$ receptor expressed on the cell surface of the mammalian cell, and thereby identifying compounds which interact with, and specifically bind to, the mammalian 5-HT$_4$ receptor. The DNA in the cell may have a coding sequence substantially the same as the coding sequence shown in FIGS. 1 and 3 (SEQ ID NOs. 1 and 2). Various methods of detection may be employed. The compounds may be "labeled" by association with a detectable marker substance (e.g., radiolabel or a non-isotopic label such as biotin). Preferably, the mammalian cell is nonneuronal in origin. An example of a nonneuronal mammalian cell is a Cos-7 cell. Drug candidates are identified by choosing chemical compounds which bind with high affinity to the expressed 5-HT$_4$ receptor protein in transfected cells, using radioligand binding methods well known in the art, examples of which are shown in the binding assays described herein. Drug candidates are also screened for selectivity by identifying compounds which bind with high affinity to one particular receptor but do not bind with high affinity to any other receptor subtypes or to any other known receptor. Because selective, high affinity compounds interact primarily with the target 5-HT$_4$ receptor site after administration to the patient, the chances of producing a drug with unwanted side effects are minimized by this approach.

This invention provides a pharmaceutical composition comprising a drug identified by the method described above and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Once the candidate drug has been shown to be adequately bioavailable following a particular route of administration, for example orally or by injection (adequate therapeutic concentrations must be maintained at the site of action for an adequate period to gain the desired therapeutic benefit), and has been shown to be non-toxic and therapeutically effective in appropriate disease models, the drug may be administered to patients by that route of administration determined to make the drug bioavailable, in an appropriate solid or solution formulation, to gain the desired therapeutic benefit.

Applicants have identified a novel 5-HT receptor subtype protein, designated 5-HT$_4$ and have described methods for the identification of pharmacological compounds for therapeutic treatments. Pharmacological compounds which are directed against specific receptor subtypes provide effective new therapies with minimal side effects.

Elucidation of the molecular structures of the neuronal serotonin receptors is an important step in the understanding of serotonergic neurotransmission. This disclosure reports the isolation and amino acid sequence of a novel cDNA which encodes a human 5-HT$_4$ receptor. This disclosure reports the isolation, amino acid sequence, and functional expression of a two novel cDNAs which encode mammalian 5-HT$_4$ receptors. The identification of 5-HT receptor subtypes play a pivotal role in elucidating the molecular mechanisms underlying serotonergic transmission, and should also aid in the development of novel therapeutic agents.

A complementary DNA clone (designated pBluescript-hS10) encoding a serotonin receptor subtype, 5-HT$_4$, has been isolated from human brain, human heart and human retina. Additionally, two complementary DNA clones encoding the serotonin 5-HT$_4$ receptor subtype have been isolated from mammalian brain and their functional properties have been examined in mammalian cells. Analysis of 5-HT$_4$ structure and function provides a model for the development of drugs useful for the treatment of gastrointestinal conditions including irritable bowel disease, postoperative ileus, diabetic gastroparesis, emesis, achalasia, hiatal hernia, and esophageal spasm. In addition, 5-HT$_4$ receptors have been described functionally in the heart (Kaumann, 1992), adrenal (Lefebvre et al., 1992), and bladder (Corsi et al., 1991) indicating possible roles in cardiac rate and force of contraction, endocrine control of cortisol secretion, and urinary incontinence or spasticity. 5-HT$_4$ receptors have also been described in the brain, particularly in areas such as the hippocampus, in which we have localized the gene encoding 5-HT$_4$ receptors (S10-95), indicating a potential role in cognitive enhancement (Bockaert et al., 1992).

This invention identifies a mammalian serotonin receptor, its amino acid sequence, and its mammalian gene, the activation of which is coupled to activation of adenylate cyclase. The information and experimental tools provided by this discovery are useful to generate new therapeutic agents, and new therapeutic or diagnostic assays for this receptor protein, its associated mRNA molecule or its associated genomic DNA. The information and experimental tools provided by this discovery will be useful to generate new therapeutic agents, and new therapeutic or diagnostic assays for this new serotonin receptor subtype, its associated mRNA molecule, or its associated genomic DNA.

Specifically, this invention relates to the isolation of human cDNA clone and mammalian cDNA clones encoding a new serotonin receptor, designated 5-$HT_4$. In addition, the mammalian 5-$HT_4$ receptors have been expressed in COS-7 cells by transfecting the cells with the plasmids pcEXV-S10-87 and pcEXV-S10-95. The pharmacological binding properties of the encoded 5-$HT_4$ receptor have been determined, and the binding properties classify this receptor as a novel serotonin receptor. Mammalian cell lines expressing the mammalian 5-$HT_4$ receptor on the cell surface have been constructed, thus establishing the first well-defined, cultured cell lines with which to study the novel 5-$HT_4$ receptor.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

METHODS AND MATERIALS

PCR Amplification: The third (III) and fifth (V) transmembrane (TM) domains of the following receptors were aligned and used to synthesize a pair of degenerate primers: 5-$HT_{1A}$, 5-$HT_{1C}$, 5-$HT_2$ and the 5-$HT_{1D\alpha/\beta}$ receptors. Primers 3.17 and 5.5 ([5'-TGGAATTCTG(C/T)G(C/T)IAT(A/C/T)(G/T)CICTGGA(C/T)(A/C) G(C/G)TA-3'] (SEQ ID No. 9), [5'-CATIA(G/C/A)I(G/A)IIA(G/A)IGG(T/G/A/)AT(G/A)(T/A)A(G/A)AAIGC-3']) (SEQ ID No. 10) were used to amplify 5 µg of poly (A+) RNA from rat brain that was reverse transcribed by avian myeloblastosis virus reverse transcriptase (AHV). PCR was performed on single-stranded cDNA under the following conditions: 94° C. for 1 min, 50° C. for 2 min and 72° C. for 3 min for 40 cycles. Following PCR, 90 µl of the reaction was phenol:chloroform extracted and precipitated; 10 µl was visualized on a gel using ethidium bromide staining. After precipitation the sample was treated with T4 DNA polymerase and digested with EcoR1 prior to separation on a 1% agarose gel. The DNA fragments (200 to 400 base pairs) were isolated from the gel, kinased and cloned into pBluescript. Recombinant clones were analyzed by sequencing, one fragment 270 base pairs in length, named S10, was identified. This sequence contained a "TM IV" like domain and represented a potentially new serotonin receptor. The corresponding full length cDNA was isolated from a rat brain cDNA library.

Rat PCR primers (from TM3 to TM7) were used to amplify single-stranded cDNA prepared from human heart, brain and retina, as described above. Those human PCR DNA fragments were subcloned in pBluescript and sequenced.

cDNA Library Construction, Screening and Sequencing Rat brains were dissected from adult male CD rats (Charles River Laboratories) and total RNA was prepared by the guanidine thiocyanate method (Chirgwin, J. W. et al.; 1979). Poly $A^+$RNA was purified with a Fast track kit (Invitrogen Corp., San Diego, Calif.). Double stranded (DS) cDNA was synthesized from 5 µg of poly $A^+$RNA according to Gubler and Hoffman (Gubler, U. and B. J. Hoffman, 1983). The resulting DS cDNA was ligated to BstXI/EcoRI adaptors (Invitrogen Corp.), the excess of adaptors was removed by chromatography on Sepharose CL 4B (Pharmacia LKB) and the DNA was then size selected on a Gen-Pak Fax HPLC column (Zhao, D. et al., 1992) (Waters, Millipore Corp., Milford, Mass.). High molecular weight fractions were ligated in pCDM8 cut by BstxI (Invitrogen Corp.). The ligated DNA was electroporated in *E. Coli* MC 1061 (Gene Pulser, Biorad). A total of 20 ×$10^6$ independent clones with an insert mean size of 1.9 kb could be generated. Before amplification, the library was divided into pools of 2.5 to 5×$10^4$ independent clones. After 18 hours amplification, the pools were stored at −85° C. in 20% glycerol.

100 pools of the cDNA library, representing 3.2×$10^6$ primary clones, were screened using exact PCR primers derived from the S10 PCR clone sequence. 1 µl (4×$10^6$ bacteria) of each amplified pool was subjected directly to 40 cycles of PCR and the resulting products analyzed by agarose gel electrophoresis and Southern blotting. Two out of four positive pools were analyzed further and by sib selection and plating out, two individual full length cDNA clones, S10-87 and S10-95, were isolated. DS-DNA was sequenced with a sequanase kit (US Biochemical, Cleveland, Ohio) according to the manufacturer. Nucleotide and peptide sequences analysis were performed with GCG programs.

Genomic cloning and sequencing: A human fibroblast genomic library in λ dash II (≈1.5×$10^6$ total recombinants; Stratagene, LaJolla, Calif.) was screened using a 45 nt. oligonucleotide probe derived from the rat S10-87 receptor gene, designed in the 3' end of the carboxyl terminal tail (from the anti-sense strand [nucleotide 1220–1264), 5' T C A A A A G C A T G A T T C C A G G - GACTCTGGGTCATTGTGTATGGG CAA 3' (SEQ ID No. 11) (see FIG. 1). The oligomer was labeled with [$^{32}$P]γATP by using polynucleotide kinase. Hybridization was performed at medium stringency conditions: 45° C. in a solution containing 37.5% formamide, 5× SSC (1× SSC is 0.15M sodium chloride, 0.015M sodium citrate), 1× Denhardt's solution (0.02% polyvinylpyrrolindone, 0.02% Ficoll, 0.02% bovine serum albumin), and 200 µg/µl sonicated salmon sperm DNA. The filters were washed at 45° C. in 0.1× SSC containing 0.1% sodium dodecyl sulfate and exposed at −70° C. to Kodak XAR film in the presence of an intensifying screen. Lambda phage clones hybridizing with the probe were plaque purified and DNA was prepared for Southern blot analysis (Southern, 1975; Sambrook et al., 1989). A 900 bp Hind2/SstI hybridizing fragment was subcloned into pUC18 (Pharmacia, Piscataway, N.J.)). Nucleotide sequence analysis was accomplished by the Sanger dideoxy nucleotide chain termination method (Sanger et al., 1977) on denatured double-stranded plasmid templates, using Sequenase (US Biochemical Corp., Cleveland, Ohio).

PCR Amplification of a Partial Length Human S10-87 cDNA Clone: The 900 bp Hind2/SstI fragment contained sequence encoding the human S10–87 carboxy terminal tail, including the stop codon. This sequence was used to generate a 25 mer (reverse primer) containing the stop codon: 5' CCTCAATCAGAAGCATGATTCCAGG 3'(SEQ ID No. 12). As a forward primer we used the 5' end of the human PCR fragment previously identified (FIG. 6): 5'TTGGTC-TATAGGAACAAGATGACCC 3' (SEQ ID No. 13). These human PCR primers were used to amplify single stranded cDNA prepared from human brain as previously described. The amplified DNA was subcloned and sequenced as described above.

Isolation of the full length human S10-95 cDNA clone: 20 pools of a human hippocampal cDNA library (3 kb average size insert, in pcEXV-3) representing $10^6$ independent clones were screened by PCR with TM4-TM6 primers as previously described. Five positive pools were identified, one of those pools was analyzed further and by sib selection a 5 kb cDNA clone, CG-17, was isolated. Double Stranded-DNA was sequenced as described above. Nucleotide and peptide sequence analysis were performed with the Genetics Computer Group sequence analysis software package.

DNA transfection: The full coding region of S10-87 (clone CG-5) and S10-95 (clones CG-6 and CG-17) were subcloned in the correct orientation in the mammalian expression vectors pcDNAl-Amp (Invitrogen Corp.), and pcEXV-3 (Miller, J. and R. N. Germain, 1986) (CG-7 and CG-8 respectively). For transient expression, Cos-7 cells were transfected by the DEAE-Dextran method, using 1 µg of DNA /$10^6$ cells (Warden, D. and H. V. Thorne, 1968).

Membrane Preparation: Membranes were prepared from transiently transfected COS-7 cells which were grown to 100% confluence. The cells were washed twice with phosphate-buffered saline, scraped from the culture dishes into 5 ml of ice-cold phosphate-buffered saline, and centrifuged at 200×g for 5 min at 4°. The pellet was resuspended in 2.5 ml of ice-cold Tris buffer (20 mM Tris -HCl, pH 7.4 at 23°, 5 mM EDTA), and homogenized by a Wheaton tissue grinder. The lysate was subsequently centrifuged at 200×g for 5 min at 4° to pellet large fragments which were discarded. The supernatant was collected and centrifuged at 40,000×g for 20 min at 4°. The pellet resulting from this centrifugation was washed once in ice-cold Tris wash buffer and finally resuspended in a final buffer containing 50 mM Tris-HCl and 0.5 mM EDTA, pH 7.4 at 23°. Membrane preparations were kept on ice and utilized within two hr for the radioligand binding assays. Protein concentrations were determined by the method of Bradford (1976) using bovine serum albumin as the standard.

Radioligand Binding: [$^3$H]5-HT binding was performed using slight modifications of the 5-HT$_{1D}$ assay conditions reported by Herrick-Davis and Titeler (1989) with the omission of masking ligands. Radioligand binding studies were achieved at 37° C. in a total volume of 250 µl of buffer (50 mM Tris, 10 mM MgCl$_2$, 0.2 mM EDTA, 10 µM pargyline, 0.1% ascorbate, pH 7.4 at 37° C.) in 96 well microtiter plates. Saturation studies were conducted using [$^3$H]5-HT at 10 different concentrations ranging from 1.0 nM to 100 nM. Displacement studies were performed using 10 nM [$^3$H]5-HT. The binding profile of drugs in competition experiments was established using 7 concentrations of compound. Incubation times were 30 min for both saturation and displacement studies. Nonspecific binding was defined in the presence of 10 µM 5-HT. Binding was initiated by the addition of 50 µl membrane homogenates (10–20 µg). The reaction was terminated by rapid filtration through presoaked (0.5% polyethyleneimine) filters using 48R Cell Brandel Harvester (Gaithersburg, Md.). Subsequently, filters were washed for 5 sec with ice cold buffer (50 mM Tris HCL, pH 7.4 at 40° C.), dried and placed into vials containing 2.5 ml of Readi-Safe (Beckman, Fullerton, Calif.), and radioactivity was measured using a Beckman LS 6500C liquid scintillation counter. The efficiency of counting of [$^3$H]5-HT averaged between 45–50%. Binding data were analyzed by computer-assisted nonlinear regression analysis (Accufit and Accucomp, Lundon Software, chagrin Falls, Ohio). IC$_{50}$ values were converted to K$_i$ values using the Cheng-Prusoff equation (1973).

[$^3$H]GR113808 binding was performed using slight modifications of the method of Waeber et al., 1993. Radioligand binding studies were achieved at 37° C. in a total volume of 250 µl of buffer (50 mM Tris, 10 µM, 0.01% ascorbate, pH 7.4 at 37° C.) in 96 well microtiter plates. Saturation studies were conducted using [$^3$H]GR113808 at 10–12 different concentrations ranging from 0.005–2.5 nM. Displacement studies were performed using 0.2–0.4 nM [$^3$H]GR113808. The binding profile of drugs in competition experiments was established using 10–12 concentrations of compound. Incubation times were 30 min for both saturation and displacement studies. Nonspecific binding was defined in the presence of 50 µM 5-HT. Binding was initiated and terminated as described for [$^3$H]5-HT binding (see above). Radioactivity was measured and data were analyzed as described above for [3H]5-HT.

Measurement of cAMP Formation: The transiently transfected Cos-7 cells were incubated in Dulbecco's modified Eagle's medium, 5 mM theophylline, 10 mM Hepes (4-[2-Hydroxyethyl]-1-piperazineethanesulfonic acid), 10 µM pargyline, and/or appropriate concentrations of antagonists for 20 minutes at 37° C., 5% CO$_2$. Serotonin or other agonists in the presence or absence of forskolin (FSK) (10 µM) were then added at appropriate concentrations and incubated for an additional 10 minutes at 37° C., 5% CO$_2$. The media was aspirated and the reaction stopped by the addition of 100 mM HCl. The plates were stored at 4° C. for 15 minutes, centrifuged for 5 minutes, 500×g to pellet cellular debris, and the supernatant aliquotted and stored at -20° C. prior to assessment of cAMP formation by radioimmunoassay (cAMP Radioimmunoassay kit, Advanced Magnetics, Cambridge, Mass.). Radioactivity was quantitated using a Packard COBRA Auto Gamma Counter equipped with data reduction software. Functional data was fitted to a four parameter logistic equation to obtain response parameters (EC$_{50}$, E$_{max}$, nH; Inplot, GraphPad, San Diego, Calif.).

Drugs: [$^3$H]5-HT (specific activity=22.7 Ci/mmole) was obtained from New England Nuclear, Boston, Mass. [$^3$H]GR113808 (specific activity=82 Ci/mmol) was obtained from Amersham International (Arlington Hts., Ill.). All other chemicals were obtained from commercial sources and were of the highest grade purity available.

EXPERIMENTAL RESULTS

Figure 4A:
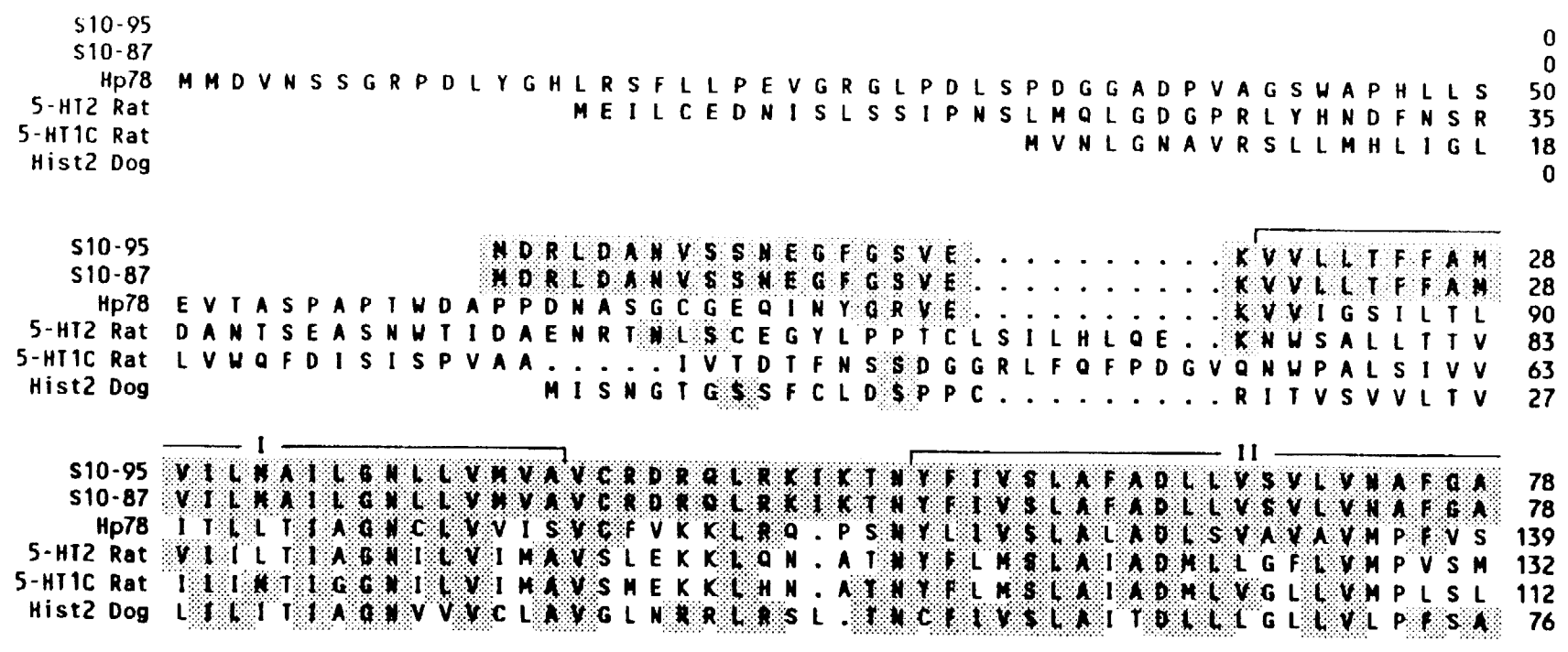
Figure 4B:
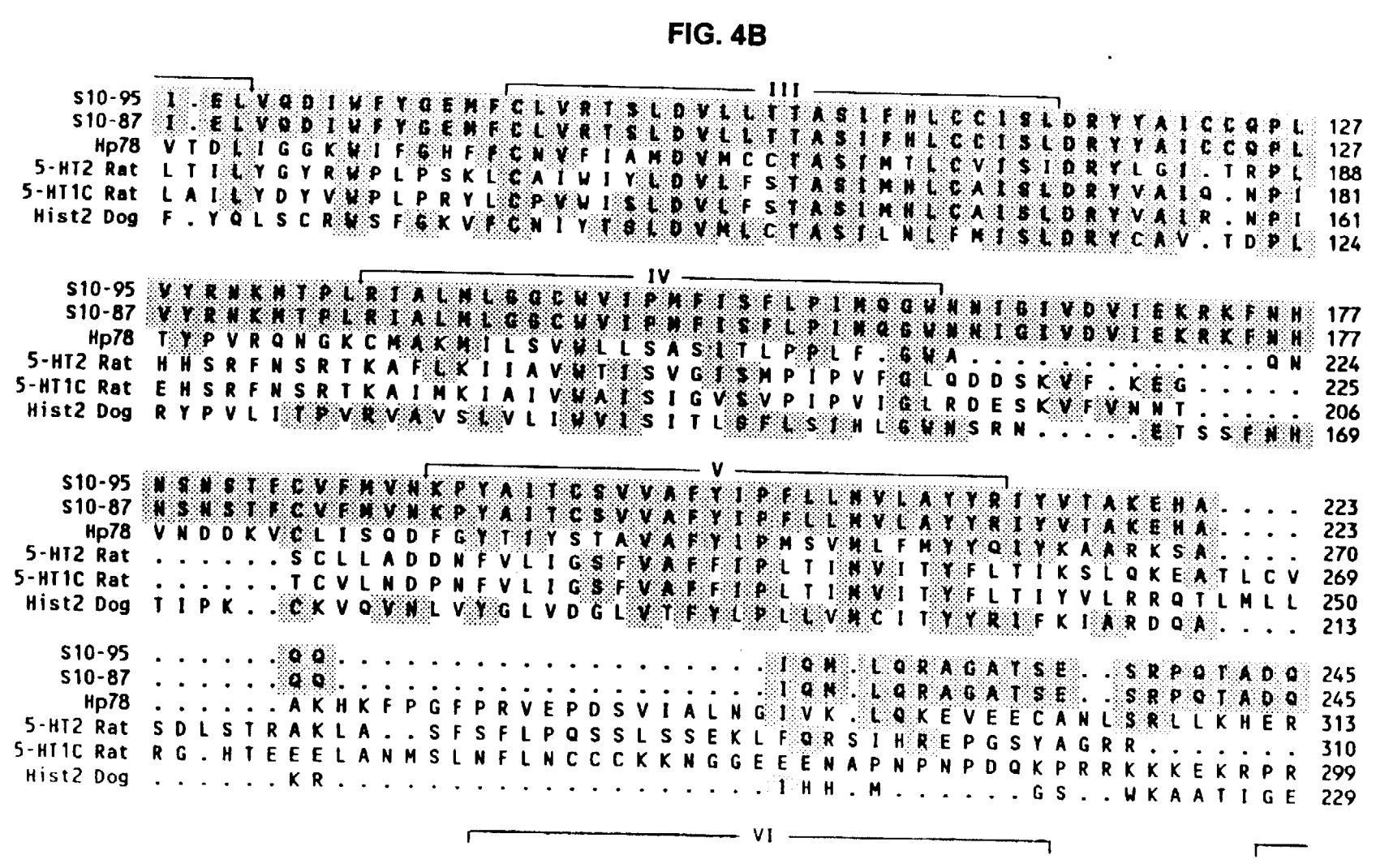

A 270 bp DNA fragment (S10) was identified when rat brain cDNA was used as template in a PCR amplification with two degenerate oligonucleotide primers derived from well conserved regions among several serotonin receptors, in the third and fifth putative transmembrane domains. The peptide sequence corresponding to this S10 PCR clone contained a "transmembrane IV like" domain. Since we used "serotonin receptor specific" PCR primers, this S10 clone represented a potentially new serotonin receptor. The corresponding full length cDNA was isolated from a rat brain cDNA library. Since five amplified commercial phage cDNA libraries turned out to be negative, we split the plasmid cDNA library into small pools of 2.5 to 5×$10^4$ independent clones before amplification to avoid a potential growth bias against the S10 cDNA clone. By direct PCR analysis of bacterial pools, subsequent sib selection and standard filter hybridization, two cDNA clones were identified, S10-87 (5.5 kb) and S10-95 (4.5 kb). The nucleotide and deduced amino acid sequences are shown in FIG. 1 (S10-87) and FIG. 2 (S10-95). Surprisingly the peptide sequences between those two clones are only 96.7% identical, diverging in the second half of the carboxy terminus tails, downstream of position 359 (FIG. 3). In addition, the entire 3' untranslated regions are totally divergent. The longest open reading frame for S10-87 encodes a protein of 387 amino acids and 406 amino acids for S10-95. The hydrophobicity plot displayed seven hydrophobic, putative membrane spanning regions which when compared to other G protein-coupled receptors did not show any significant high homologies, even to other serotonin receptors (Table 1 and FIG. 4). It is interesting to note that the highest homology, overall or restricted to the 7 TM region, is exhibited by the human histamine H$_2$ receptor, which like the 5-HT$_4$ receptor, is coupled to stimulation of cAMP.

Both S10-87 and S10-95 proteins carry 4 potential N-glycosylation sites in positions 7, 180, 316, and 352. They also possess 3 potential phosphorylation sites for protein kinase C in positions 218, 248, 318 and 4 potential phosphorylation sites for casein kinase II in positions 9, 97, 218 and 288. A potential palmitoylation site is present in both clones at the cysteine found in position 329. A large number of G protein-coupled receptors carry a cysteine in the same position and O'Dowd et al. have speculated that it plays an important role in the functional coupling of the human $\beta_2$-adrenergic receptor. In addition, clone S10-95 carries one more potential phosphorylation site for protein kinase C at position 400. This additional phosphorylation site could lead to differential functional coupling between the S10-87 and S10-95 receptors.

Since we isolated two different S10 cDNA clones by screening a library made from an entire brain, we checked for differential expression in seven different parts of the brain by PCR amplification using pairs of primers specific for each clone. The results are summarized in table 2. Clone S10-95 seems to be transcribed everywhere in the rat brain except in cerebellum. Clone S10-87 is only expressed in striatum. It remains to be determined if only one or both receptors are expressed in rat cortex.

The partial human S10-87 nucleotide (FIG. 11A) and deduced amino acid sequences (FIG. 11B) are shown. The sequences are highly similar to the rat S10-87 homolog, 90.8% at the nucleotide level and 93.8% at the amino acid level (FIGS. 12 and 13 respectively).

The full length human S10-95 nucleotide (FIG. 14A) and deduced amino acid sequences (FIG. 14B) are shown. Compared to the rat S10-95 sequence, it shows 90.7% identity at the nucleotide level and 91.8% identity at the amino acid level (FIGS. 15 and 16 respectively). The human S10-95 nucleotide sequence contains one nucleotide insertion in position 1159. This insertion creates a frame shift and introduces a stop codon in the reading frame 16 nucleotides downstream. The protein motifs are highly conserved between the rat and human homologs except for a casein kinase II potential phosphorylation site in position 288 which is lost in both human receptors. The human homologs both carry a potential cAMP/cGMP phosphorylation site in position 338 in their carboxy terminal tail which is absent in the rat homologs. A comparison of the amino acid sequence between the human and the rat S10-95 clones beginning from the initiating methionine and ending with the stop codon of the human S10-95 clone, reveals 31 amino acid changes of which 11 are non conservative, including 2 in TM1, 1 in TM2 and 1 in TM4. Due to the nucleotide insertion and the corresponding frame shift described above, the carboxy terminal tail of the human S10-95 receptor is 16 amino acid shorter than its rat homolog.

Identical to the rat homologs, both human clones are identical in the loops and transmembrane regions, differing only in the second half of their carboxy terminal tail (FIG. 17, nucleic acid sequence; FIG. 18, aa sequence).

The human PCR cDNA fragments (TM-3 to TM-7) are 100% identical between heart, brain and retina. The nucleotide and deduced amino acid sequences are shown in FIG. 5. The human sequence shows 90.7% homology with the rat nucleotide sequence (FIG. 6) and 92.3% homology (FIG. 7) with the rat amino acid sequence.

The genes encoding the rat S10-87 and S10-95 receptors were transiently expressed in Cos-7 cells for pharmacological evaluation. Initial experiments using 5 nM [$^3$H]5-HT indicated that both S10-87 and S10-95 were serotonergic sites as demonstrated by the degree of specific binding and density of sites expressed in the transfected cells when compared against the mock transfected controls. Saturation analysis of S10-87 (CG-7) was performed using 10 concentrations of [$^3$H]5-HT (1–100 nM) and yielded a Bmax of 1,938±399 fmol/mg of protein and a $K_d$ for [$^3$H]5-HT of 7.87±0.06 nM. The degree of specific binding at concentrations of [$^3$H]5-HT close to the $K_d$ ranged from 70–84% throughout the experimental series (including saturation and competition studies). Although the use of [$^3$H]5-HT as a radioligand to label 5-HT$_4$ receptors in brain tissue is not efficient due to the nonselectivity of the ligand, it became clear in the present studies using a homogeneous receptor population that [$^3$H]5-HT would label this particular receptor. In fact, [$^3$H]5-HT appears to be labelling the high affinity state of the 5-HT$_4$ receptor which is not unusual for the conditions upon which this receptor has been studied. Similar results using an agonist radioligand have been previously reported for the cloned 5-HT$_2$ receptor (Branchek et al., 1990).

A pharmacological binding profile of S10-87 and S10-95 (CG-7 and CG-8) was performed and demonstrated that this novel receptor was similar to the 5-HT$_4$ receptor as defined by functional assays in the literature (Bockaert et al., 1992). This is clearly shown in table 3 where the binding affinities of various serotonergic agents are displayed for S10. Notably, 5-HT and the tryptamine derivative 5-methoxytryptamine possessed high affinity. Furthermore, as previously reported for the 5-HT$_4$ receptor, benzamide derivatives including cisapride, BRL 24924 and zacopride bound with fairly high affinity to receptors expressed from the S10 gene. ICS 205930, a tropanyl-indole derivative, which has been reported to be an antagonist at both 5-HT$_3$ and 5-HT$_4$ receptors (Bockaert et al., 1992), also bound to these receptor sites. Compounds such as 8-hydroxy-2-(di-n-propylamino)tetralin, ketanserin, sumatriptan and 5-carboxyamidotryptamine were of low affinity having $K_i$ values estimated to be greater than 1 µM. This data would rule out S10 from belonging to other serotonergic receptor subfamilies such as 5-HT$_1$ and 5-HT$_2$. Taken together, the complete pharmacological profile also differentiates S10 from the related subtype 5-HT$_{4B}$ (U.S. Ser. No. 971,960, filed, Nov. 3, 1992, copending). Although some of the drugs tested also have good affinity for 5-HT$_3$ receptors, S10 is clearly a 5-HT$_4$ receptor based upon the binding data and the functional data demonstrating a positive-coupling to adenylate cyclase. Finally, a correlation plot for the binding affinities of 5-HT, cisapride, BRL 24924, zacopride, and ICS 205930 against their functional responses in adenylate cyclase assays from cultured mouse collicular neurons (Dumuis et al., 1989) yielded a correlation coefficient of 0.96 (FIG. 8). Thus, the rank order of potency for these key compounds also provides conclusive evidence that S10 encodes a 5-HT$_4$ receptor.

Figure 9:
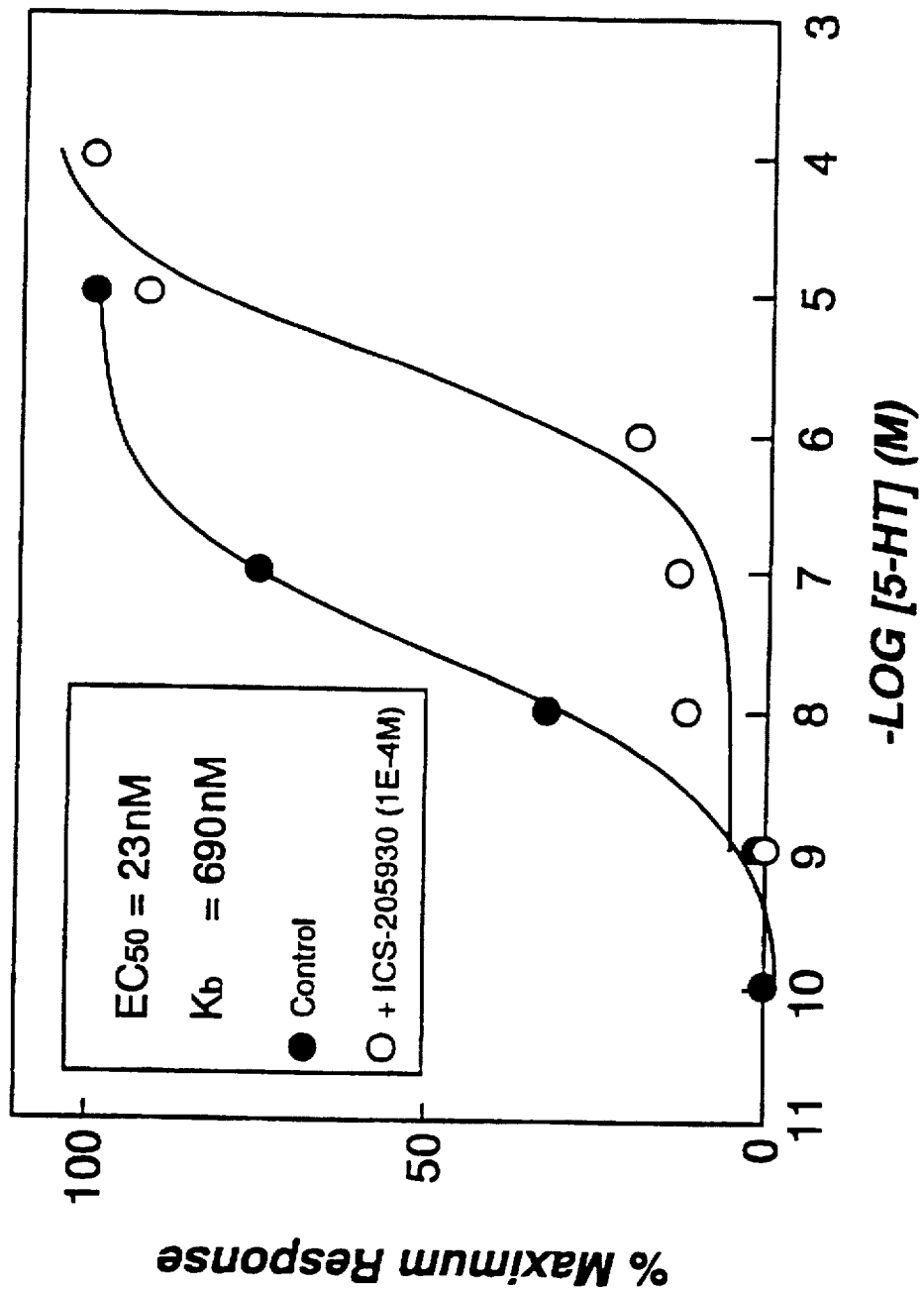
FIG. 9: Stimulation of cAMP production by 5-HT in transiently transfected Cos-7 cells expressing the cloned rat 5-HT$_4$ (CG-7) receptor and antagonism by ICS 205930. cAMP measurements on intact cells were as described under Methods and Materials. Each data point represents the mean of triplicates from a single experiment representative of at least 2 others. The vertical bars indicate S.E.M. Data are presented as percent maximum cAMP released by 5-HT (basal CAMP release: 0.020±0.002 pmol/ml/10 min; maximum cAMP release: 0.42±0.03 pmol/ml/10 min).
Figure 10:
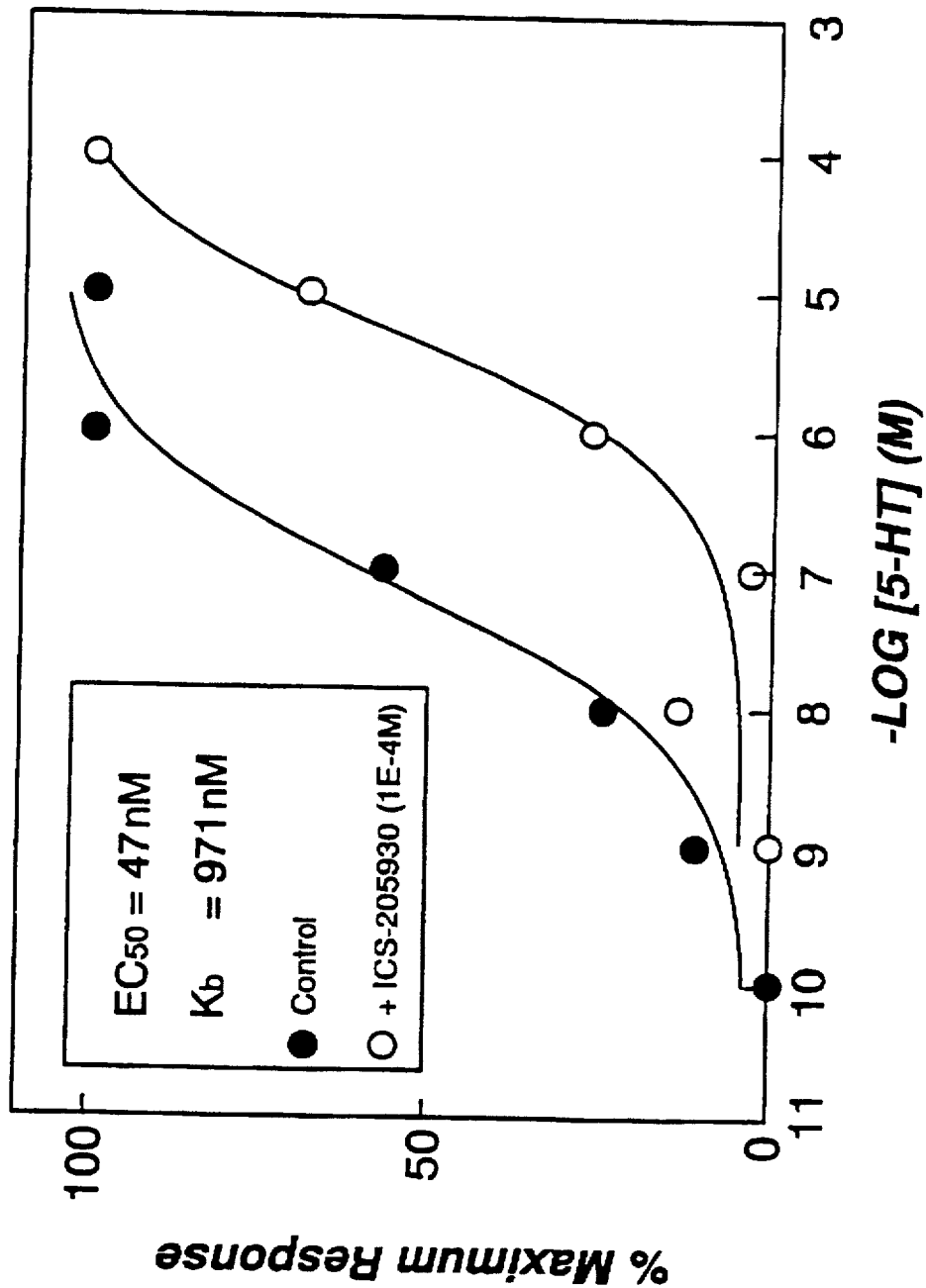
FIG. 10: Stimulation of cAMP production by 5-HT in transiently transfected Cos-7 cells expressing the cloned rat 5-HT$_4$ (CG-8) receptor and antagonism by ICS 205930. cAMP measurements on intact cells were as described under Methods and Materials. Each data point represents the mean of triplicates from a single experiment representative of at least two others. The vertical bars indicate S.E.M. Data are presented as percent maximum cAMP released by 5-HT (basal cAMP release: 0.023±0.004 pmol/ml10 min; maximum cAMP release: 0.57±0.04 pmol/ml10 min).
Figure 19:
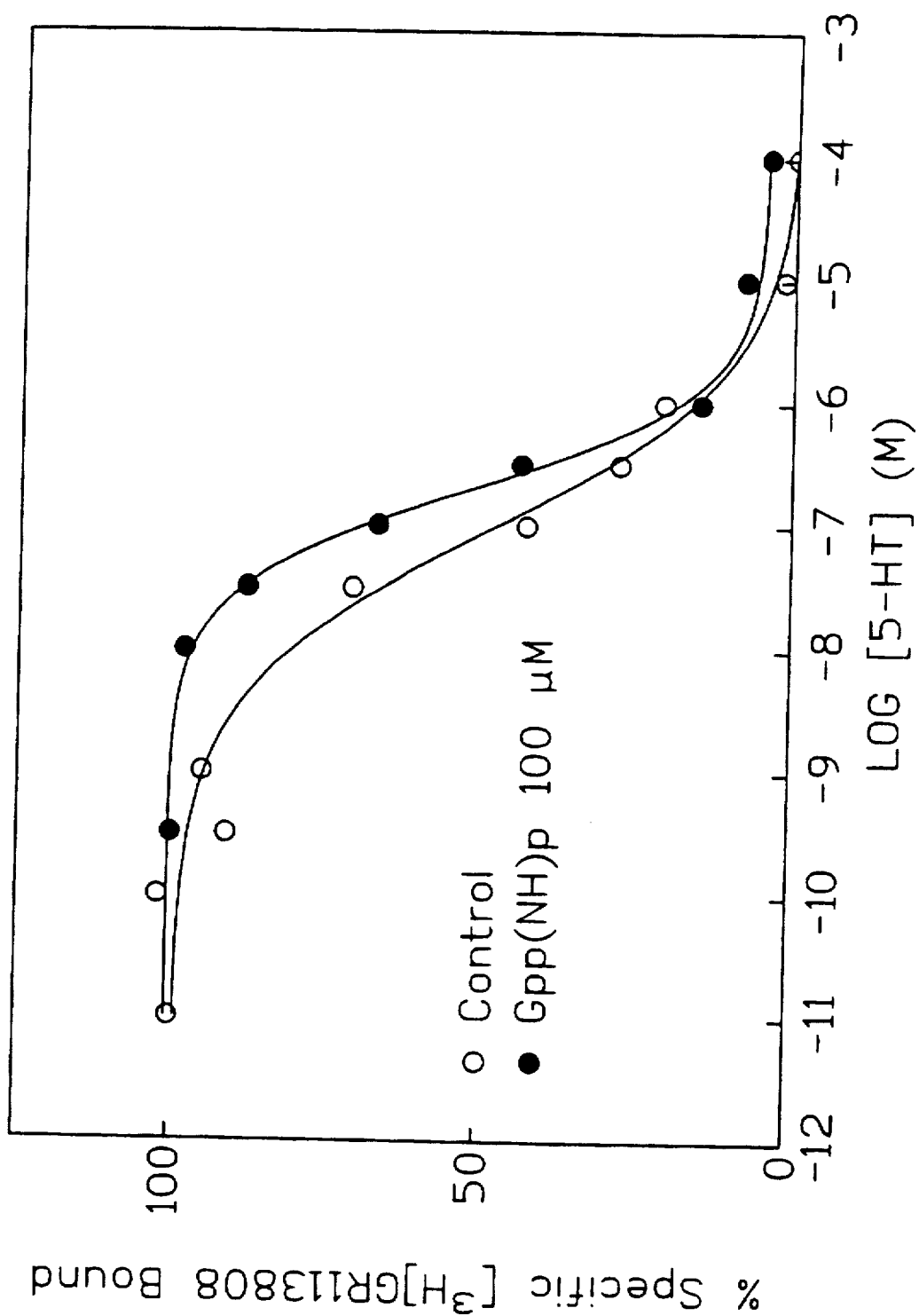
FIG. 19: Inhibition of [$^3$H]GR11380 binding on the cloned rat CG-8 receptor by 5-HT, in the absence and presence of Gpp(NH)p (100 µM). Membranes harvested from transient transfectants (COS-7 cells) were incubated with [$^3$H]IGR113808 (0.2–0.4 nM) for 30 min at 37° C. Nonspecific binding was defined by 50 µM unlabelled 5-HT. Data are from a single experiment. Data were analyzed by computer-assisted nonlinear regression analysis (Accufit; Lundon Software).

To examine the ability of S10 clone to couple to adenylate cyclase, Cos-7 cells transiently expressing S10 were tested for the ability to exhibit an increase in basal cAMP release or a decrease in FSK-stimulated cAMP response. 5-HT (1 µM) had no effect on either basal or FSK-stimulated adenylate cyclase activity in untransfected or mock-transfected Cos-7 cells (data not shown), indicating that endogenous cyclase-coupled serotonin receptors are not present in untransfected cells. Preliminary studies were carried out by adding only one dose of various drugs in triplicate. Addition of 5-HT (1 µM) to this system caused stimulation of basal cAMP release (CG-7=0.020±0.002; CG-8=0.023±0.004 pmol/ml/10 min) by about 30 fold for each clone; no inhibition of either the basal or FSK-stimulated cAMP release was observed. On the contrary, addition of 10 µM PSK together with 1 µM 5-HT stimulated cAMP accumulation about 10-fold more than either agent alone (data not shown). For various compounds, full dose-response curves were determined for both clones and the data are summarized in table 4. 5-HT caused a concentration-dependent stimulation of basal adenylate cyclase activity with mean EC$_{50}$s of 26±3 and 51±7 nM and E$_{max}$s of 2.107 and 2.598% basal cAMP release for CG-7 and CG-8 respectively (FIGS. 9 and 10). Among the tryptamine derivatives tested, 5-MeOT was approximately equipotent with 5-HT in both clones, whereas α-Me-5-HT and 5-CT were about 10 and 200 times respectively less potent than 5-HT at CG-7. On the other hand, the latter two compounds displayed approximately 20 and 30 fold lower affinity than 5-HT respectively for CG-8. The 2-methoxy-4-amino-5-chloro-substituted benzamides (cisapride, BRL-249245 and zacopride) were less potent agonists than 5-HT in stimulating basal cAMP release and displayed different rank order of potency for CG-7 and CG-8. As indicated in table 4 using CG-7, cisapride, BRL-24924 and zacopride exhibited approximately 10, 30 and 100 fold lower potency than 5-HT respectively, whereas at CG-8 these compounds had almost equal affinity. Thus, although not different in binding properties, these subtle differences in affinity in functional assays of the two "variants" (CG-7 and CG-8) indicate the potential to develop separate therapeutic entities for each separate target. All the agonists tested acted as full agonists with the exception of cisapride, BRL-24924 and zacopride, which also displayed antagonist activity and were therefore partial agonists at both clones, with intrinsic activities ranging between 0.85 and 1.4 (Table 4). ICS-205-930 (100 μM) had similar effect at the two clones and was found to be a silent antagonist causing parallel dextral shifts in the concentration effect curve of 5-HT without altering the maximum response significantly. The estimated K$_B$ value for ICS-205-930 was not significantly different between the two clones (CG-7=962±244 nM; CG-8=607±30 nM). Responses to 5-HT were not affected by spiperone or methiothepin (10 μM) in either clone.

Saturation analysis of rat 5-HT$_{4A}$ S10-87 (CG-7) and S10-95 (CG-8) clones and human 5-HT$_{4A}$ clone CG-17 were performed using 10–12 concentrations of [$^3$H]GR113808 (0.005–2.5 nM) and revieled a single saturable site of high affinity for both clones (CG-7: K$_d$=0.74 nM, B$_{max}$=5.7 pmol/mg membrane protein; CG-8: K$_d$=1.0 nM, B$_{max}$=3.7 pmol/mg membrane protein; CG-17: K$_d$=0.20 nM, B$_{max}$=1.8 pmol/mg membrane protein). These preliminary data indicate that although the rat clones (CG-7 and CG-8) have similar affinity for the antagonist [$^3$H]GR113808, the human clone (CG-17) displays approximately 5-fold higher affinity than the rat clones for this ligand. For all three clones nonspecific binding increased linearly with increasing ligand concentration. The degree of specific binding at concentrations of [$_3$H]GR113808 (0.4–0.5 nM) ranged from 80–90%).

The pharmacological binding profile of S10-87 and S10-95 (CG-7, CG-8, respectively) was investigated in displacement studies using [$^3$H]GR113808 and/or [$^3$H]5-HT. In order to compare CG-17 pharmacology with that previously obtained for the rat clones, CG-7 and CG-8, displacement studies on the human CG-17 clone were performed using [$^3$H]5-HT as the radioligand.

A range of 5-HT$_4$ receptor agonists and antagonists completely inhibited the specific binding of [$^3$H]GR113808 on both the rat CG-7 and CG-8 clones. Affinity values and Hill slopes derived from the curves using computer analysis are presented in Table 5. As previously observed using [$^3$H]5-HT as the radioligand, the rat CG-7 and CG-8 receptors had very similar pharmacology. Of the agonists tested, only those active in 5-HT$_4$ containing preparations (5-HT and 5-MeOT) potently inhibited [$^3$H]GR113808. By contrast, agonists for other 5-HT receptors, for example 5-HT$_{1A}$ receptor agonist, 8-OH-DPAT, the 5-HT$_{1D}$ receptor agonist, sumatriptan, the 5-HT$_2$ receptor antagonist, ketanserin, had no effect on [$^3$H]GR113808 binding at concentrations up to 1 μM. The substituted benzamides, cisapride, BRL-24924 and zacopride, partial agonists at 5-HT$_4$ receptor all potently inhibited [$^3$H]GR113808 binding. Specific [$^3$H]GR113808 binding was also inhibited by the 5-HT$_4$ receptor antagonist ICS-205930.

For both the rat CG-7 and CG-8 clones, Hill slopes for the inhibition of [$^3$H]GR113808 binding by 5-HT$_4$ receptor agonists but not the antagonist, ICS-205930, were shallow in the absence of Gpp(NH) with the exception of 5-CT, and α-Me-5-HT. For agonists that had shallow displacement curves, the binding was resolved into high and low affinity components and these are summarized in Table 5. The K$_i$ values obtained for the high affinity state of the receptor using [$^3$H]GR113808 as the radioligand were compatible with the K$_i$ values obtained previously using [$^3$H]5-HT as the radioligand which labels the high affinity state of the receptor (Table 5 and 6). Some differences were observed for the K$_i$ values of high affinity state of CG-7 compared to CG-8 (Table 3) and their nH values. For example, although there were no differences in the K$_i$ values of CG-7 and CG-8, the displacement curve obtained for 5-MeOT using CG-8 clone could not be resolved into two sites. Also the K$_i$ value obtained for the high affinity state of CG-8 using cisapride was approximately 3-fold lower than that obtained for CG-7 previously using [$^3$H]5-HT to directly label the high affinity state of the receptor. We are currently investigating these differences using [$^3$H]5-HT to directly label the high affinity state.

In the presence of 100 μM Gpp(NH)p, competition binding curves for the agonists displaying shallow curves in the absence of Gpp(NH)p were shifted to the right and this is exemplified for 5-HT in Fig. The Hill slopes were increased.

Preliminary results obtained with the human clone (CG-17) using [$^3$H]5-HT as the radioligand in displacement studies are summarized in Table 3. Similar to the rat CG-7 and CG-8 clones, 8-OH-DPAT, sumatriptan and ketanserin were inactive at the CG-17 clone for up to concentration of 1 μM. The differences observed between the human and the rat CG-8 clones were as follows. The biggest difference was observed with α-Me-5-HT which had approximately 100 fold higher affinity for the human CG-17 clone. Zacopride, 5-MeOT and cisapride had about 7-fold, 5-fold and 4-fold higher affinity, respectively for the human clone CG-17.

DISCUSSION

We have identified two cDNA clones encoding the pharmacologically-defined 5-HT$_4$ receptor. This receptor is expressed at low levels in rat brain if we consider its frequency in the cDNA library ($\leq 1:10^6$), surprisingly, two receptors dif f ering in their carboxy-terminus regions have been isolated. Since the 3' untranslated nucleotide sequences are also different, these two receptors could be encoded by two different genes or could arise by alternative splicing of pre-mRNA. These two receptors (S10-87 and S10-95) are differentially expressed in rat brain and the physiological relevance of the S10-87 receptor being expressed only in striatum remains to be determined.

The pharmacology binding profile and the functional coupling obtained from cells expressing S10 clones indicate that these genes both encode a pharmacologically-defined 5-HT$_4$ receptor. The cloned rat CG-7 and CG-8 genes transiently expressed in Cos-7 cells coupled to stimulation of adenylate cyclase. The magnitude of this response (~20–25 fold) was large. With the exception of 5-MeOT, agonist potencies determined from functional assays were less than expected from K$_i$ values obtained from binding assays using [$^3$H]5-HT. Could this result be due to the possibility that the dose of [$^3$H]5-HT used in binding assays measures only the high affinity site of agonists? This is not likely, as it would not account for the data obtained with ICS-205-930 which is a silent antagonist in the present system displaying approximately 6 (CG-8) and 10 (CG-7) fold lower affinity in the functional assay as compared to the binding experiments. It is more likely that differences in experimental conditions used in binding assays compared with those used in the functional assays (such as membrane vs. cells, buffers and extent of equilibrium achieved) accounts for these differences.

5-HT responses were resistant to blockade by methiothepin and spiperone (10 μM). As the concentration of these agents exceed their equilibrium dissociation constants for their respective receptor sites by 10–100 fold, it seems that 5-HT$_1$-like (5-HT$_{1A}$, 5-HT$_{1B}$, 5-HT$_{1C}$, 5-HT$_{1D}$, 5-HT$_E$, 5-HT$_{1F}$), 5-HT$_2$ and 5-HT$_{4B}$ receptors can be ruled out. In addition, the weak agonistic activity of 5-CT relative to 5-HT further supports the notion that 5-HT$_1$-like receptors are probably not involved (Bradley, 1986). The results obtained with the indole agonists reflect those reported at the 5-HT$_4$ receptor in both the CNS and the periphery (Dumuis et al., 1988; Craig and Clarke, 1990; Eglen et al., 1990; Baxter, Craig and Clarke, 1991). The substituted benzamides, cisapride, BRL-24924 and zacopride acted as partial agonists. Although the benzamides also possess affinity for 5-HT$_3$ receptors, they lack intrinsic efficacy (Schuurkes et al., 1985; Sanger and King, 1988). Furthermore, the affinity of ICS-205-930 for antagonism of 5-HT response at S10 is 1–3 orders of magnitude lower than that at 5-HT$_3$ receptors (Richardson et al., 1985) and therefore indicates a binding site different from 5-HT$_3$ receptor.

As was the case with the rat 5-HT$_4$ receptor, there are two forms of the human homolog, most likely splice variants differing in the carboxyterminal end of the receptor. Non conservative amino acid substitutions, especially in transmembrane domains 1, 2 and 4 could provide the basis for the pharmacological differences observed between the rat and the human 5-HT$_4$ receptors (see below). A difference in the functional response is observed between the two rat clones: although the CG-7 construct (S10-87) gives higher levels of receptor expression in COS-7 cells (Bmax of 5.7 pmol/mg of protein versus 3.7 pmol/mg for S10-95), in the functional assay, the CG-8 construct (S10-95) reproducibly shows a higher level of cAMP stimulation (2598±154% of basal cAMP release versus 2107±52% for CG-7). This finding could be attributed to the different amino acid sequence in the carboxy terminal tail of the rat receptors, specially since the rat S10-95 isoform carries an additional potential phosphorylation site at position 400, absent in S10-87 (CG-7).

Since the human S10-95 homolog lacks the last 16 carboxy terminal amino acids which carry the phosphorylation site mentioned above in the rat homolog, it will be interesting to check for differences in the level of cAMP stimulation upon activation of the rat and human S10-95 homologs. In the same way, after we get the full length human S10-87, both human isoforms will be compared in binding and functional assays.

All the unique pharmacological characteristics described above define the S10 genes as adenylate cyclase stimulatory "5-HT$_4$" receptors reported in the literature that are expressed in the ileum (Craig and Clarke, 1990), hippocampus (Shenker et al., 1987), esophagus (Baxter et al., 1991), embryo colliculi neurons (Dumius et al., 1988), atrium (Kaumann et al., 1990), adrenal (Lefebvre et al., 1992), and bladder (Corsi et al., 1991), and distinguish these clones from all other cloned subtypes of 5-HT receptor. Although the binding profile of CG-7 and CG-8 were identical (Table 3), some differences in agonist potency (benzamides in particular) were observed between them in the functional assays. This is not surprising since the amino acid sequences of these two clones are identical, apart from the cytoplasmic carboxy tail, a region that is important for G protein-coupling, where the CG-8 receptor carries an extra phosphorylation site. Cisapride, BRL-24924 and zacopride had similar affinities at CG-8 whereas BRL-24924 and zacopride displayed approximately 4 and 15 fold lower affinity than cisapride at CG-7 clone for stimulation of adenylate cyclase. It is noteworthy that tissue differences in the potency of benzamides have been reported (Baxter et al., 1991) and whether this reflects a heterogeneity of 5-HT$_4$ receptors remains to be investigated.

The data obtained with the rat CG-7 and CG-8 clones and the human CG-17 clone using [$^3$H]GR113808 are very similsr to those reported by Grossmann et al. (1993) and Waeber et al. (1993) with this ligand using guinea pig and human brain tissues. Specific [$^3$H]GR113808 binding readily saturated for all three clones (CG-7, CG-8 and CG-17). Scatchard analysis of specific binding in all three clones revealed the involvement of a single site. Curve fitting analysis showed an equilibrium dissociation of approximately 1 nM for both rat clones (CG-7 and CG-8) whereas this value was about 5-fold lower for the human CG-17 clone (K$_d$=0.2 nM). The K$_d$ value obtained for the human CG-17 clone is in excellent agreement with that reported by Waeber et al. (1993) using human brain (0.23–0.37 nM) and is very similar to that of the guinea pig brain tissue (0.13–0.2 nM; Waeber et al., 1993; Grossmann et al., 1993). The K$_d$ value of [$^3$H]GR113808 for rat brain tissue has not been reported, however, it is interesting that the affinity obtained for GR113808 from functional receptor assays in the rat oesophagus (Grossmann et al., 1993) is about 0.3 nM which indicates that this antagonist has similar affinities for the human and the rat tissue used. The discrepancies between our data and those reported may be due to methodology, or different subtype (brain vs. oesophagus), however, this remains to be investigated.

The rank order of potency of compounds competing for specific [$^3$H]GR113808 are very similar for both CG-7 and CG-8 and is cisapride> 5-HT> BRL-24924> 5-MeOT= ICS205930> zacopride> α-Me-5-HT> 5-CT. This order of potency is different from that observed with guinea pig caudate (Grossmann et al., 1993; cisapride> 5-HT> ICS205930> BRL-24924> zacopride> 5-MeOT> α-Me-5-HT> 5-CT) and human caudate (Waeber et al., 1993; cisapride> ICS205930> BRL-24924> 5-HT> 5-MeOT. Whether these differences are due to species or different population of high affinity state of the receptor in the various preparation, remains to be investigated. Interestingly, the displacement curves for most of the agonists competing for specific [$^3$H]GR113808 were shallow and could be resolved to high and low affinity states. Gpp(NH)p shifted these curves to the right and in the case of 5-HT the Hill coefficient was increased to unity; however for some agonists the shift was not complete. Grossmann et al. (1993) using guinea pig caudate also observed shallow competition curves for some agonist that could be partially shifted by the addition of GTP (Grossmann et al., 1993). However, Waeber did not observe shallow binding curves with the human caudate tissue. These observations indicate that the G protein content of these prepartations may be different which may reflect differences in the coupling of the receptor with a G protein.

Using [$^3$H]5-HT as the radioligand, the affinity values for the human CG-17 clone are in general comparable with that obtained by us previously tor the rat CG-7 and CG-8 clones with few exceptions. The most striking differences appears to be for α-Me-5-HT which displays approximately 100 fold higher affinity for the human CG-17. However, it has to pointed out that the data are compared with 2 different radioligands and this difference has to be further investigated using the same radioligand for all both the rat and human clones in parallel. 5-MeOT was approximately 3 fold less potent whereas zacopride was about 7 fold more potent at the human CG-17 as compared to the rat clones.

The cloning and expression of genes encoding 5-HT$_4$ receptors allows, for the first time, the ability to develop subtype selective drugs using radioligand binding assays. It will further provide definitive answers to whether there are significant species differences in the pharmacology of 5-HT$_4$ receptors. In addition, the intrinsic activity of drugs can be determined from measures of adenylate cyclase activation in these transfected cells. So far, native tissue preparations have shown great disparity in agonist activity. 5-HT$_4$ receptors have been implicated in a wide variety of functions. Existing drugs such as metaclopramide and cisapride appear to exert a large part of their action through 5-HT$_4$ receptors (Taniyama et al., 1991; Meulemans and Schurkes, 1992; Flynn et al., 1992). Experience with these agents indicates a clear therapeutic role for 5-HT$_4$ receptors in the gastrointestinal system for conditions including irritable bowel disease, postoperative ileus, diabetic gastroparesis, emesis, achalasia, hiatal hernia, and esophageal spasm. In addition, 5-HT$_4$ receptors have been described functionally in the heart (Kaumann, 1992), adrenal (Lefebvre et al., 1992), and bladder (Corsi et al., 1991) indicating possible roles in cardiac rate and force of contraction, endocrine control of cortisol secretion, and urinary incontinence or spasticity. 5-HT$_4$ receptors have also been described in the brain, particularly in areas such as the hippocampus, in which we have localized the gene encoding 5-HT$_4$ receptors (S10-87), indicating a potential role in cognitive enhancement (Bockaert et al., 1992). As more specific pharmacological tools are developed, additional therapeutic indications will certainly be uncovered.

TABLE I

TM homology of the S10 receptor with other 7 TM receptors

| SEROTONIN | ADRENERGIC | DOPAMINE | PEPTIDE |
|---|---|---|---|
| 5-HT$_{1A}$ Hu 44 | Alpha-1A Hu 45 | D$_1$ Hu 43 | Subst K Hu 25 |
| 5-HT$_{1D\alpha}$ Hu 40 | Alpha-1B Hu 43 | D$_2$ Hu 42 | TSH 27 |
| 5-HT$_{1D\beta}$ Hu 41 | Alpha-1C Hu 40 | D$_3$ Rt 46 | |
| 5-HT$_{1E}$ Hu 41 | Alpha-2A Hu 42 | D$_4$ Hu 45 | |
| 5-HT$_{1F}$ Hu 41 | Alpha-2B Hu 40 | D$_5$ Hu 45 | |
| 5-HT$_2$ Hu 42 | Alpha-2C Hu 40 | | |
| 5-HT$_{1C}$ Hu 44 | | | |
| | Beta-1 Hu 46 | HISTAMINE | MUSCARINIC |
| 5-HT Dro S 43 | Beta-2 Hu 44 | | |
| 5-HT Dro I$_A$ 40 | Beta-3 Hu 42 | H$_1$ Bov 36 | m1 35 |
| 5-HT Dro I$_B$ 41 | | H$_2$ Hu 46 | |
| 5-HT$_{4B}$ Hu 44 | | | |
| | | ADENOSINE | |
| | | A1 Rat 32 | |
| | | A2 Hu 31 | |

TABLE 3

Binding affinities of key ligands for the identification of S10 (CG-7 and CG-8) as a 5-HT$_4$ receptor. Affinity constants (Ki; nM) of drugs competing for S10 labeled with 10 nM [3H]5-HT were determined to pharmacologically define the encoded receptor as 5-HT$_4$. Ki (nM) values were calculated using the Cheng-Prusoff equation or estimated to be >1000 nM based upon one point displacements using a drug concentration of 1 uM. Affinity constants are expressed as the mean ± SEM (n ≥ 2). Ki values estimated to be >1000 were determined according to one point displacements studies at a concentration of 1 uM. (n = 2 except BRL 24924 tested at CG-8: n = 1)
CHARACTERIZATION OF CLONE S-10

Saturation Analysis: Kd = 7.87 ± 0.06 nM
Bmax = 1,938 fmol/mg prot
Pharmacological profile:

| DRUG | CG-7 | CG-8 |
|---|---|---|
| 5-HT | 8.6 ± 0.6 | 6.4 ± 0.5 |
| Cisapride | 10.9 ± 0.3 | ND |
| 5-MeOT | 27.5 ± 5 | ND |
| BRL 24924 | 27.7 ± 5 | 21.1* |
| ICS 205930 | 115 ± 12 | 138 ± 26 |
| Zacopride | 130 ± 10 | 136 ± 5 |
| 8OHDPAT | >1000 | ND |
| Ketanserin | >1000 | ND |
| Sumatriptan | >1000 | ND |
| 5-CT | >1000 | ND |

*n = 1
ND = not determined

TABLE 2

| Primers | Cortex | Cerebellum | Brain Stem | Hippocampus | Olfactory Bulb | Striatum | Thalamus |
|---|---|---|---|---|---|---|---|
| TM3-5 | + | − | + | + | + | + | + |
| S10-87 | ND | − | − | − | − | + | − |
| S10-95 | ND | − | + | + | + | + | + |

Table 2: PCR localization of the S10 mRNA in 7 different part of the rat brain. The TM3-5 primers do not differentiate between clones S10-87 and S10-95. The S10-87 primers were designed from the nucleotide sequences coding for the TM 6 domain common to both receptors and for the carboxy terminus end specific to S10-87. In the same way, the S10-95 primers are specific for S10-95.

TABLE 4

Pharmacological profile for the cAMP response using the human 5-HT$_{4A}$ (CG-7 and CG-8) receptor transiently expressed in Cos-7 cells, comparison with the binding data obtained with CG-7 clone using [$^3$H]5-HT. cAMP measurements on intact cells were as described under Methods and Materials. EC$_{50}$ values (concentration producing the half-maximal effect) were derived from the analysis of full dose-response curves. Maximum response produced by each drug was normalized to the 5-HT maximum response which is indicated as having an intrinsic activity of 1.0. Data are means ± S.E.M. of three separate experiments. The apparent dissociation constant of antagonist (K$_s$) (ICS 205930) was calculated according to the formula: K$_s$ = [B]/(A'/A) − 1], where [B] is the concentration of antagonist, A' and A the EC$_{50}$ values of agonist measured respectively in the presence and in the absence of antagonist (Furchgott, 1972).

| DRUG | EC$_{50}$ or K$_s$ (nM) CG-7 | EC$_{50}$ or K$_s$ (nM) CG-8 | I.A.* CG-7 | I.A.* CG-8 | K$_i$ (nM) CG-7 | K$_i$ (nM) CG-8 |
|---|---|---|---|---|---|---|
| 5-MeOT | 21 ± 6 | 31 ± 13 | 1.0 | 1.0 | 27 ± 5 | ND |
| 5-HT | 26 ± 3 | 51 ± 7 | 1.0 | 1.0 | 8.6 ± 0.6 | 6.4 ± 0.5 |
| Cisapride | 191 ± 26 | 413 ± 199 | 1.2 | 1.4 | 11 ± 0.3 | ND |
| α-Me-5-HT | 250 ± 91 | 1,038 ± 31 | 0.90 | 1.0 | ND | ND |
| BRL-24924 | 736 ± 129 | 250 ± 25 | 1.1 | 0.9 | 28 ± 5 | 21 |
| Zacopride | 2,740 ± 274 | 239 ± 33 | 1.1 | 1.0 | 130 ± 10 | 136 ± 5 |
| 5-CT | 5,570 ± 808 | 1,411 ± 211 | 0.85 | 1.2 | >1,000 | ND |
| ICS-205930 | 962 ± 244 | 607 ± 30 | 0 | 0 | 115 ± 12 | 138 ± 26 |

ND, not determined.
Maximum response to 5-HT in Cos-7 cells transiently transfected with CS-7 and CG-8 genes was:
CG-7 = 2,107 ± 52% of basal cAMP release
CG-8 = 2,598 ± 154% of basal cAMP release
Cisapride, BRL-24924 and zacopride had no antagonist activity and ICS-205930 had no intrinsic agonist acitivity.

TABLE 5

The affinities of various compounds that compete for 0.2–0.4 nM [$^3$H]GR113808 binding in membranes of COS-7 cells transiently transfected with rat clones CG-7 and CG-8.

| COMPOUNDS | CG-7 | CG-8 |
|---|---|---|
| 5-HT | 237 K$_H$ = 2.6, BH = 22%<br>K$_L$ = 357<br>nH = 0.62 | 116 KH = 2.5, BH = 24%<br>KL = 197<br>nH = 0.67 |
| 5-CT | >10,000 | >10,000 |
| 5-Me-OT | 438 KH = 14, BH = 17%<br>KL = 658<br>nH = 0.57 | 518 KH = , BH =<br>KL =<br>nH = 0.66 |
| BRL-24924 | 189 KH = 37, BH = 34%<br>KL = 371<br>nH = 0.85 | 188 KH = 23, BH = 32%<br>KL = 373<br>nH = 0.81 |
| ZACOPRIDE | 729 KH = 424, BH = 68%<br>KL = 2,757<br>nH = 0.80 | 820 KH = , BH =<br>KL =<br>nH = 0.85 |
| d-LSD | >10,000 | >10,000 |
| CISAPRIDE | ND | 84 KH = 2.7, BH = 11%<br>KL = 105<br>nH = 0.83 |
| ICS205930 | ND | 529 |
| α-Me-5-HT | 2,255 | 1,855 |

Affinity estimates are given as K$_i$ values (nM) using the computer program "Accucomp" (Lundon Software). Values are from a single experiment. K$_H$ and K$_L$ values indicated the affinity in nM for the high affinity and low affinity state of the receptor, B$_H$ is the percentage of high affinity sites and nH is the Hill coefficient.
ND, not determined.

TABLE 6

Binding affinities of key ligands for the identification of the human CG-17 clone as a 5-HT$_{4A}$ receptor.

| COMPOUND | K$_i$ (nM) |
|---|---|
| 5-HT | 4.2 |
| 5-MeOT | 71 |
| 5-CT | >10,000 |

TABLE 6-continued

Binding affinities of key ligands for the identification of the human CG-17 clone as a 5-HT$_{4A}$ receptor.

| COMPOUND | K$_i$ (nM) |
|---|---|
| Cisapride | 12 |
| α-Me-5-HT | 1.6 |
| BRL-24924 | 21 |
| Zacopride | 17 |
| Sumatriptan | >1,000 |
| 8-OH-DPAT | >1,000 |
| Ketanserin | >1,000 |

Affinity constants (Ki, nM) of drugs competing for CG-17 cloned labeled with 10 nM [$^3$H] 5-HT were calculated using the Cheng-Prusoff equation or estimated to be greater than 1,000 nM based upon one point displacement using a drug concentration of 1 μM. Values are from a single experiment.

REFERENCES

Adham, N., P. Romanienko, P. Hartig, R. L. Weinshank, and T. Branchek. The rat 5-hydroxytryptamine$_{1B}$ receptor is the species homologue of the human 5-hydroxytryptamine$_{1Dβ}$ receptor. Mol. Pharmacol. 41:1–7 (1992).

Adham, N., H.-T. Kao, L. E. Schechter, J. Bard, M. Olsen, D. Urquhart, M. Durkin, P. R. Hartig, R. L. Weinshank, and T. A. Branchek. Cloning of a novel human serotonin receptor (5-HT1F): A fifth 5-HT$_1$ receptor subtype coupled to the inhibition of adenylate cyclase. Proc. Natl. Acad. Sci. U.S.A., in press.

Bockaert, J., J. R. Fozard, A. Dumuis, and D. E. Clarke. The 5-HT$_4$ receptor: a place in the sun. Trends Pharmacol. Sci. 13:141–145 (1992).

Bockaert, J., M. Sebben, and A. Dumius. Pharmacological characterization of 5-hydroxytryptamine$_4$ (5-HT$_4$) receptors positivly coupled to adenylate cyclase in adult guinea-pig hippocampal membranes: effect of substituted benzamide derivatives. Mol. Pharmacol. 37:408–411 (1990).

Bradford, M. M. A rapid and sensitive method for the quantification of microgram quantities of protein utilizing the principle of protein-dye binding. Anal. Biochem. 72:248–254 (1976).

Bradley, P. B., G. Engel, W. Fenuik, J. R. Fozard, P. P. Humphrey et al. Proposals for the nomenclature of functional receptors for 5-hydroxytryptamine. Neuropharmacology 25:563–576 (1986).

Branchek, T., N. Adham, M. Macchi, H.-T. Kao, and P. R. Hartig. [$^3$]-DOB (4-bromo-2,5-dimethoxyphenylisopropylamine) and [$^3$H]ketanserin label two affinity states of the cloned human 5-hydroxytryptamine$_2$ receptor. Mol. Pharmacol. 38:604–609 (1990).

Capecchi, M. R., Science 244: 1288–1292 (1989).

Chirgwin, J. M., A. E. Przybyla, R. J. MacDonald, and W. J. Rutter. Isolation of biologically active ribonucleic acid from sources enriched in ribonuclease. Biochemistry 18:5294 (1979).

Cohen, J. S., Trends in Pharm. Sci. 10:435 (1989)

Cushing, D., and M. L. Cohen. Comparison of the serotonin receptors that mediate smooth muscle contraction in canine and porcine coronary artery. J. Pharmacol. Exp. Ther. 261:856–861 (1992).

Demchyshyn, L., R. K. Sunahara, K. Miller, M. Teitler, B. J. Hoffman, J. L. Kennedy, P. Seeman, H. H. M. Van Tol, and H. B. Niznik. A human serotonin 1D receptor variant (5-HT1Dβ) encoded by an intronless gene on chromosome 6. Proc. Natl. Acad. Sci. U.S.A. 89:5522–5526 (1992).

Dumuis, A., R. Bouhelal, M. Sebben, R. Cory, and J. Bockaert. A nonclassical 5-hydroxytryptamine receptor positively coupled with adenylate cyclase in the central nervous system. Mol. Pharmacol. 34:880–887 (1988).

Dumuis, A., M. Sebben, and J. Bockaert. (1989). The gastrointestinal prokinetic benzamide derivatives are agonists at the non-classical 5-HT receptor (5-HT$_4$) positively coupled to adenylate cyclase in neurons. Naunyn-Schmiedeberg's Arch. Pharmacol. 340:403–410 (1989).

Fargin, A., J. R. Raymond, M. J. Lohse, B. K. Kobilka, M. G. Caron, and R. J. Lefkowitz. The genomic clone G21, which resembles a β-adrenergic receptor sequence, encodes the human 5-HT$_{1A}$ receptor. Nature (Lond.) 335:358–360 (1988).

Foquet, M., D. Hoyer, L. A. Pardo, A. Parekh, F. W. Kluxen, H. O. Kalkman, W. Stuhmer, and H. L ubbert. Cloning and functional characterization of the rat stomach fundus serotonin receptor. EMBO J. 11(3):3481–3487 (1992).

Grossman, C. J., Kilpatrick, G. J. and Bunce, K. T. Development of a radioligand binding assay for 5HT4 receptors in guinea pig and rat brain. Br. J. Pharmacol. 109:618–624 (1993)

Gubler, U., and B. J. Hoffman. A simple and very efficient method for generating cDNA libraries. Gene 25:263 (1983).

Hamblin, M. W., and M. A. Metcalf. Primary structure and functional characterization of a human 5-HT$_{1D}$-type serotonin receptor. Mol. Pharmacol. 40:143–148 (1991).

Hartig, P. R., H.-T. Kao, M. Macchi, N. Adham, J. Zgombick, R. Weinshank, and T. Branchek. The molecular biology of serotonin receptors: an overview. Neuropsychopharmacol. 3:335–347 (1990).

Herrick-Davis, K. and M. Titeler. Detection and characterization of the serotonin 5-HT$_{1D}$ receptor in rat and human brain. J. Neurochem. 50:1624–1631 (1988).

Hogan, B., et al., Manipulating the Mouse Embryo, A Laboratory Manual, Cold Spring Laboratory (1986).

Jin, H., D. Oksenberg, A. Ashkenazi, S. J. Peroutka, A. M. V. Duncan, R. Rozmahel, Y. Yang, G. Mengod, J. M. Palacios, and B. F. O'Dowd. Characterization of the human 5-hydroxytryptamine$_{1B}$ receptor. J. Biol. Chem. 267:5735–5738 (1992).

Kobilka, B. K., T. Frielle, S. Collins, T. Yang-Feng, T. S. Kobilka, U. Francke, R. J. Lefkowitz, and C. G. Caron. An intronless gene encoding a potential member of the family of receptors coupled to guanine nucleotide regulatory proteins. Nature 329:75–77 (1988).

Levy, F. O., T. Gudermann, M. Birnbaumer, A. J. Kaumann, and L. Birnbaumer. Molecular cloning of a human gene (S31) encoding a novel serotonin receptor mediating inhibition of adenylyl cyclase. FEBS. Lett. 296:201–206 (1992).

Low, M. J., R. M. Lechan and R. E. Hammer, Science 231: 1002–1004 (1986).

Maniatis, T., E.F. Fritsch, and J. Sambrook, Molecular Cloning Manual, Cold Spring Harbor Laboratory, Cold Spring Harbor New York (1982).

Maricq, A. V., A. V. Peterson, A. J. Brake, R. M. Myers, and D. Julius. Primary structure and functional expression of the 5-HT3 receptor, a serotonin-gated ion channel. Science 254:432–436 (1991).

Maroteaux, L., F. Saudou, N. Amlaiky, U. Boschert, J. L. Plassat, R. Hen. Mouse 5-HT1B serotonin receptor: cloning, functional expression, and localization in motor control centers. Proc. Natl. Acad. Sci. U.S.A. 89:3020–3024 (1992).

McAllister, G., A. Charlesworth, C. Snodin, M. S. Beer, A. J. Noble, D. N. Middlemiss, L. L. Iverson, and P. Whiting. Molecular cloning of a serotonin receptor from human brain (5-HT1E): A fifth 5-HT1-like subtype. Proc. Natl. Acad. Sci. U.S.A. 89:5517–5521 (1992).

Miller, J., and R. N. Germain. Efficient cell surface expression of class II MHC molecules in the absence of associated invariant chain. J. Exp. Med. 164:1478–1489 (1986).

Mylecharane, E. and C. Phillips. Mechanisms of 5-hydroxytryptamine-induced vasodilation. In: The Peripheral Actions of 5-hydroxytryptamine, J. R. Fozard, ed. Oxford University Press, Oxford, pp. 147–181 (1989).

Oberdick, J., R. J. Smeyne, J. R. Mann, S. Jackson and J. I. Morgan, Science 248: 223–226 (1990).

O'Dowd, B. F., M. Hnatowich, M. G. Caron, R. J. Lefkowitz, and M. Bouvier. Palmitoylation of the Human β$_2$-Adrenergic Receptor. J. Biol. Chem. 264:7564–7569 (1989).

Pritchett, D. B., A. W. J. Bach, M. Wozny, O. Taleb, R. Dal Toso, J. C. Shih, and P. H. Seeburg. Structure and functional expression of a cloned rat serotonin 5-HT-2 receptor. EMBO J. 7:4135–4140 (1988).

Sambrook, J., E. F. Fritsch, and T. Maniatis. In: Molecular Cloning: A Laboratory Manual, 2nd Edition, Cold Spring Harbor Laboratory, Cold Spring Harbor, N.Y. (1989).

Sarver, N., et al., Science 247: 1222 (1990).

Shenker, A., S. Maayani, H. Weinstein, and J. P. Green. Pharmacological characterization of two 5-hydroxytryptamine receptors coupled to adenylate cyclase in guinea pig hippocampal membranes. Mol. Pharmacol. 31:357–367 (1987).

Southern, E. Detection of specific sequences among DNA fragments seperated by gel electrophoresis. J. Mol. Biol. 98:503–517 (1975).

Trevethick, M. A., W. Feniuk, and P. P. A. Humphrey. 5-hydroxytryptamine induced relaxation of neonatal porcine vena cava in vitro. Life Sci. 35:477–486 (1984).

Waeber, C., Sebben, M., Grossman, C, Javoy-Agid, F., Bockaert, J. and Dumuis, A. [3H]-GR113808 labels 5-HT4 receptors in the human and guinea-pig brain. Neuroreport 4:1239–1242 (1993)

Warden, D., and H. V. Thorne. Infectivity of polyoma virus DNA for mouse embryo cells in presence of diethylaminoethyl-dextran. J. Gen. Virol. 3:371 (1968).

Weinshank, R. L., J. M. Zgombick, M. Macchi, N. Adham, H. Lichtblau, T. A. Branchek, and P. R. Hartig. Cloning, expression, and pharmacological characterization of a human $\alpha_{2B}$-adrenergic receptor. Mol. Pharmacol. 38:681–688 (1990).

Weinshank, R. L., J. M. Zgombick, M. Macchi, T. A. Branchek, and P. R. Hartig. The human serotonin 1D receptor is encoded by a subfamily of two distinct genes: 5-$HT_{1D\alpha}$ and 5-$HT_{1D\beta}$. Proc. Natl. Acad. Sci. U.S.A. 89:3630–3634 (1992a).

Weintraub, H. M., Scientific American, January (1990) p.40.

Zhao D., J. Yang, K. E. Jones, C. Gerald, Y. Suzuki, P. G. Hogan, W. W. Chin, and A. H. Tashjian, Jr. Molecular cloning of a cDNA encoding the thyrotropin-releasing hormone receptor and regulation of its mRNA in rat GH cells. Endocrinology. 130:3529–3536 (1992).

Zemlan, F. P., and E. F. Schwab. Characterization of a novel serotonin receptor subtype (5-$HT_{1S}$) in rat CNS: interaction with a GTP binding protein. J. Neurochem. 57:2092–2099 (1991).

Zgombick, J. M., R. L. Weinshank, M. Macchi, L. E. Schechter, T. A. Branchek, and P. R Hartig. Expression and pharmacological characterization of a canine 5-hydroxytryptamine$_{1D}$ receptor subtype. Mol. Pharmacol. 40: 1036–1042 (1991).

Zgombick, J. M., L. E. Schechter, M. Macchi, P. R. Hartig, T. A. Branchek, and R. L. Weinshank. Human gene S31 encodes the pharmacologically defined serotonin 5-hydroytryptamine$_{1E}$ receptor. Mol. Pharmacol. 42: 180–185 (1992).

Zimmer, A., and P. Gruss, Nature 338: 150–153 (1989).

What is claimed is:

1. An isolated nucleic acid encoding a human 5-HT$_4$ receptor, wherein the 5-HT$_4$ receptor has an amino acid sequence as shown in FIG. 14B (Seq. ID No. 8).

2. An isolated nucleic acid molecule of claim 1, wherein the nucleic acid molecule is a DNA molecule.

3. An isolated nucleic acid molecule of claim 2, wherein the nucleic acid molecule is a cDNA molecule.

4. An isolated nucleic acid molecule of claim 2, wherein the nucleic acid molecule is genomic DNA.

5. A method of preparing a human 5-HT$_4$ receptor protein, which comprises inserting the nucleic acid molecule of claim 1 into a suitable vector; inserting the resulting vector into a suitable host cell; treating the cells so as to express the human 5-HT$_4$ receptor, and recovering the human 5-HT$_4$ receptor so expressed.

6. An isolated nucleic acid encoding a human 5-HT$_4$ receptor, wherein the 5-HT$_4$ receptor has an amino acid sequence which is the same as the amino acid sequence encoded by the human DNA inserted into plasmid pBluescript-hS10 (ATCC Accession No. 75392).

7. A vector comprising a nucleic acid molecule of claim 1.

8. A plasmid vector of claim 7.

9. A vector of claim 7 adapted for expression in a bacterial cell which comprises regulatory elements necessary for expression of the nucleic acid encoding a human 5-HT$_4$ receptor in the bacterial cell operatively linked to the nucleic acid encoding the human 5-HT$_4$ receptor so as to permit expression thereof.

10. A vector of claim 7 adapted for expression in a yeast cell which comprises regulatory elements necessary for expression of the nucleic acid encoding a human 5-HT$_4$ receptor in the yeast cell operatively linked to the nucleic acid encoding the human 5-HT$_4$ receptor so as to permit expression thereof.

11. A vector of claim 7 adapted for expression in an insect cell which comprises regulatory elements necessary for expression of the nucleic acid encoding a human 5-HT$_4$ receptor operatively linked to the nucleic acid encoding the human 5-HT$_4$ receptor so as to permit expression thereof.

12. A vector of claim 7 adapted for expression in a mammalian cell which comprises regulatory elements necessary for expression of the nucleic acid encoding a human 5-HT$_4$ receptor in the mammalian cell operatively linked to the nucleic acid encoding the human 5-HT$_4$ receptor so as to permit expression thereof.

13. A mammalian cell comprising the plasmid of claim 8.

14. A mammalian cell of claim 13, wherein the cell is an LM(tk−) cell.

15. An isolated nucleic acid encoding a human 5-HT$_4$ receptor, wherein the 5-HT$_4$ receptor has an amino acid sequence as shown in FIG. 11B (Seq. ID No. 15).

16. A plasmid designated pBluescript-hS10 (ATCC Accession No. 75392).

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1642 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: N ( i v ) ANTI-SENSE: N ( v i ) ORIGINAL SOURCE:
        ( F ) TISSUE TYPE: brain ( v i i ) IMMEDIATE SOURCE:
        ( A ) LIBRARY: rat brain
        ( B ) CLONE: S10-87

( i x ) FEATURE:
        ( A ) NAME/KEY: CDS
        ( B ) LOCATION: 101..1261
        ( D ) OTHER INFORMATION:

( x i ) SEQUENCE DESCRIPTION: SEQ ID NO:1:

```
AGCCTTGCCG AGCCTGGCTT GGTTGGAAGG AGGAGGATGC TCTGCGTGCC CAGGGTCCTG          60

TGGGCACTGA CATCCAACGT ACTCATGCCC ATTTCCTGTA ATG GAC AGA CTT GAT         115
                                              Met Asp Arg Leu Asp
                                               1               5

GCT AAT GTG AGT TCC AAC GAG GGT TTC GGG TCT GTG GAG AAG GTC GTA         163
Ala Asn Val Ser Ser Asn Glu Gly Phe Gly Ser Val Glu Lys Val Val
         10              15              20
```

| | | | | | | | | | | | | | | | | |
|---|---|---|---|---|---|---|---|---|---|---|---|---|---|---|---|---|
| CTG | CTC | ACG | TTC | TTC | GCA | ATG | GTT | ATC | CTG | ATG | GCC | ATC | CTG | GGC | AAC | 211 |
| Leu | Leu | Thr | Phe | Phe | Ala | Met | Val | Ile | Leu | Met | Ala | Ile | Leu | Gly | Asn | |
| | | | 25 | | | | | 30 | | | | | 35 | | | |
| CTG | CTG | GTG | ATG | GTT | GCT | GTG | TGC | AGG | GAC | AGG | CAG | CTC | AGG | AAA | ATA | 259 |
| Leu | Leu | Val | Met | Val | Ala | Val | Cys | Arg | Asp | Arg | Gln | Leu | Arg | Lys | Ile | |
| | | 40 | | | | | 45 | | | | | 50 | | | | |
| AAA | ACC | AAT | TAT | TTC | ATT | GTG | TCT | CTT | GCC | TTT | GCT | GAT | CTG | CTG | GTT | 307 |
| Lys | Thr | Asn | Tyr | Phe | Ile | Val | Ser | Leu | Ala | Phe | Ala | Asp | Leu | Leu | Val | |
| | 55 | | | | | 60 | | | | | 65 | | | | | |
| TCG | GTG | CTG | GTG | AAT | GCC | TTC | GGT | GCC | ATT | GAG | TTG | GTC | CAA | GAC | ATC | 355 |
| Ser | Val | Leu | Val | Asn | Ala | Phe | Gly | Ala | Ile | Glu | Leu | Val | Gln | Asp | Ile | |
| 70 | | | | | 75 | | | | | 80 | | | | | 85 | |
| TGG | TTT | TAT | GGG | GAG | ATG | TTT | TGC | CTG | GTC | CGG | ACC | TCT | CTG | GAT | GTC | 403 |
| Trp | Phe | Tyr | Gly | Glu | Met | Phe | Cys | Leu | Val | Arg | Thr | Ser | Leu | Asp | Val | |
| | | | | 90 | | | | | 95 | | | | | 100 | | |
| CTA | CTC | ACC | ACA | GCA | TCA | ATT | TTT | CAC | CTC | TGC | TGC | ATT | TCC | CTG | GAT | 451 |
| Leu | Leu | Thr | Thr | Ala | Ser | Ile | Phe | His | Leu | Cys | Cys | Ile | Ser | Leu | Asp | |
| | | | 105 | | | | | 110 | | | | | 115 | | | |
| AGG | TAT | TAT | GCC | ATC | TGC | TGT | CAA | CCT | TTG | GTT | TAT | AGA | AAC | AAG | ATG | 499 |
| Arg | Tyr | Tyr | Ala | Ile | Cys | Cys | Gln | Pro | Leu | Val | Tyr | Arg | Asn | Lys | Met | |
| | | 120 | | | | | 125 | | | | | 130 | | | | |
| ACC | CCT | CTA | CGC | ATC | GCA | TTA | ATG | CTG | GGA | GGC | TGC | TGG | GTC | ATT | CCC | 547 |
| Thr | Pro | Leu | Arg | Ile | Ala | Leu | Met | Leu | Gly | Gly | Cys | Trp | Val | Ile | Pro | |
| | 135 | | | | | 140 | | | | | 145 | | | | | |
| ATG | TTT | ATA | TCT | TTT | CTC | CCC | ATA | ATG | CAA | GGC | TGG | AAC | AAC | ATC | GGC | 595 |
| Met | Phe | Ile | Ser | Phe | Leu | Pro | Ile | Met | Gln | Gly | Trp | Asn | Asn | Ile | Gly | |
| 150 | | | | | 155 | | | | | 160 | | | | | 165 | |
| ATA | GTT | GAT | GTG | ATA | GAG | AAA | AGG | AAA | TTC | AAC | CAC | AAC | TCT | AAC | TCT | 643 |
| Ile | Val | Asp | Val | Ile | Glu | Lys | Arg | Lys | Phe | Asn | His | Asn | Ser | Asn | Ser | |
| | | | | 170 | | | | | 175 | | | | | 180 | | |
| ACA | TTC | TGT | GTC | TTC | ATG | GTC | AAC | AAG | CCC | TAT | GCC | ATC | ACC | TGC | TCT | 691 |
| Thr | Phe | Cys | Val | Phe | Met | Val | Asn | Lys | Pro | Tyr | Ala | Ile | Thr | Cys | Ser | |
| | | | 185 | | | | | 190 | | | | | 195 | | | |
| GTG | GTG | GCC | TTC | TAC | ATC | CCG | TTT | CTC | CTC | ATG | GTG | CTG | GCC | TAT | TAC | 739 |
| Val | Val | Ala | Phe | Tyr | Ile | Pro | Phe | Leu | Leu | Met | Val | Leu | Ala | Tyr | Tyr | |
| | | 200 | | | | | 205 | | | | | 210 | | | | |
| CGT | ATC | TAT | GTC | ACT | GCT | AAG | GAG | CAT | GCC | CAG | CAG | ATC | CAG | ATG | TTA | 787 |
| Arg | Ile | Tyr | Val | Thr | Ala | Lys | Glu | His | Ala | Gln | Gln | Ile | Gln | Met | Leu | |
| | 215 | | | | | 220 | | | | | 225 | | | | | |
| CAA | CGG | GCA | GGA | GCC | ACC | TCT | GAA | AGC | AGG | CCC | CAG | ACA | GCT | GAC | CAG | 835 |
| Gln | Arg | Ala | Gly | Ala | Thr | Ser | Glu | Ser | Arg | Pro | Gln | Thr | Ala | Asp | Gln | |
| 230 | | | | | 235 | | | | | 240 | | | | | 245 | |
| CAC | AGC | ACA | CAT | CGC | ATG | CGG | ACA | GAG | ACC | AAA | GCA | GCC | AAG | ACT | TTA | 883 |
| His | Ser | Thr | His | Arg | Met | Arg | Thr | Glu | Thr | Lys | Ala | Ala | Lys | Thr | Leu | |
| | | | | 250 | | | | | 255 | | | | | 260 | | |
| TGT | GTC | ATC | ATG | GGC | TGC | TTC | TGT | TTC | TGC | TGG | GCC | CCC | TTC | TTT | GTC | 931 |
| Cys | Val | Ile | Met | Gly | Cys | Phe | Cys | Phe | Cys | Trp | Ala | Pro | Phe | Phe | Val | |
| | | | 265 | | | | | 270 | | | | | 275 | | | |
| ACC | AAT | ATT | GTG | GAC | CCT | TTC | ATA | GAC | TAC | ACT | GTG | CCC | GAG | AAG | GTG | 979 |
| Thr | Asn | Ile | Val | Asp | Pro | Phe | Ile | Asp | Tyr | Thr | Val | Pro | Glu | Lys | Val | |
| | | 280 | | | | | 285 | | | | | 290 | | | | |
| TGG | ACT | GCT | TTC | CTC | TGG | CTT | GGC | TAT | ATC | AAT | TCA | GGG | TTG | AAC | CCT | 1027 |
| Trp | Thr | Ala | Phe | Leu | Trp | Leu | Gly | Tyr | Ile | Asn | Ser | Gly | Leu | Asn | Pro | |
| | 295 | | | | | 300 | | | | | 305 | | | | | |
| TTT | CTC | TAT | GCC | TTC | TTG | AAT | AAG | TCT | TTC | AGA | CGT | GCC | TTC | CTT | ATC | 1075 |
| Phe | Leu | Tyr | Ala | Phe | Leu | Asn | Lys | Ser | Phe | Arg | Arg | Ala | Phe | Leu | Ile | |
| 310 | | | | | 315 | | | | | 320 | | | | | 325 | |
| ATC | CTC | TGC | TGT | GAT | GAT | GAG | CGC | TAC | AAA | AGA | CCC | CCC | ATT | CTG | GGC | 1123 |
| Ile | Leu | Cys | Cys | Asp | Asp | Glu | Arg | Tyr | Lys | Arg | Pro | Pro | Ile | Leu | Gly | |
| | | | | 330 | | | | | 335 | | | | | 340 | | |

```
CAG ACT GTC CCC TGT TCA ACC ACA ACC ATT AAT GGA TCC ACT CAT GTG     1171
Gln Thr Val Pro Cys Ser Thr Thr Thr Ile Asn Gly Ser Thr His Val
            345             350                 355

CTA AGG TAT ACA GTT TTG CAT AGT GGT CAA CAC CAG GAA CTG GAG AAG     1219
Leu Arg Tyr Thr Val Leu His Ser Gly Gln His Gln Glu Leu Glu Lys
            360             365                 370

TTG CCC ATA CAC AAT GAC CCA GAG TCC CTG GAA TCA TGC TTT             1261
Leu Pro Ile His Asn Asp Pro Glu Ser Leu Glu Ser Cys Phe
            375             380             385

TGATTGAAGA CGTGGCTTGC CTTTAGCGGT TCATCCCATC TGTGTCTGCA TGAACAGGTT   1321
ACTATGGAAT CACTCCTGAC TCTGGGCATC ACCAGTGAAG CATGAGCATG GTGAGGCAGG   1381
GTCCGGTGAA GGTGCACAGA GGACAGCATT GAGTGGGACC TGAACCCAGC ACATTAAGGA   1441
TTTCAGAACC GTGTGGGGAT TTGAGATGTC ATCAGACCCA GTGTCTTACC CAGAGCCCAA   1501
CTGGCACCTC CCATTCCACG CTGACATGTG GTCAGTCTTT GCTCACACCT CTCCAGGGGC   1561
AGGAGCTGAC TACCTCCTAA TGTGGTGGGG AGCTCTTAAT TGTGTGGAAG TTCAGTCATT   1621
CATTGGTGGA CAGTCTCGCT G                                             1642
```

( 2 ) INFORMATION FOR SEQ ID NO:2:

( i ) SEQUENCE CHARACTERISTICS:
        ( A ) LENGTH: 387 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Arg Leu Asp Ala Asn Val Ser Ser Asn Glu Gly Phe Gly Ser
 1               5                  10                  15

Val Glu Lys Val Val Leu Leu Thr Phe Phe Ala Met Val Ile Leu Met
                20                  25                  30

Ala Ile Leu Gly Asn Leu Leu Val Met Val Ala Val Cys Arg Asp Arg
            35                  40                  45

Gln Leu Arg Lys Ile Lys Thr Asn Tyr Phe Ile Val Ser Leu Ala Phe
        50                  55                  60

Ala Asp Leu Leu Val Ser Val Leu Val Asn Ala Phe Gly Ala Ile Glu
65                  70                  75                  80

Leu Val Gln Asp Ile Trp Phe Tyr Gly Glu Met Phe Cys Leu Val Arg
                85                  90                  95

Thr Ser Leu Asp Val Leu Leu Thr Thr Ala Ser Ile Phe His Leu Cys
                100                 105                 110

Cys Ile Ser Leu Asp Arg Tyr Tyr Ala Ile Cys Cys Gln Pro Leu Val
            115                 120                 125

Tyr Arg Asn Lys Met Thr Pro Leu Arg Ile Ala Leu Met Leu Gly Gly
        130                 135                 140

Cys Trp Val Ile Pro Met Phe Ile Ser Phe Leu Pro Ile Met Gln Gly
145                 150                 155                 160

Trp Asn Asn Ile Gly Ile Val Asp Val Ile Glu Lys Arg Lys Phe Asn
                165                 170                 175

His Asn Ser Asn Ser Thr Phe Cys Val Phe Met Val Asn Lys Pro Tyr
            180                 185                 190

Ala Ile Thr Cys Ser Val Val Ala Phe Tyr Ile Pro Phe Leu Leu Met
        195                 200                 205

Val Leu Ala Tyr Tyr Arg Ile Tyr Val Thr Ala Lys Glu His Ala Gln
    210                 215                 220
```

| | | | | | | | | | | | | | | |
|---|---|---|---|---|---|---|---|---|---|---|---|---|---|---|
| Gln | Ile | Gln | Met | Leu | Gln | Arg | Ala | Gly | Ala | Thr | Ser | Glu | Ser | Arg | Pro |
| 225 | | | | | 230 | | | | | 235 | | | | | 240 |

Gln Thr Ala Asp Gln His Ser Thr His Arg Met Arg Thr Glu Thr Lys
                        245                     250                     255

Ala Ala Lys Thr Leu Cys Val Ile Met Gly Cys Phe Cys Phe Cys Trp
                 260                     265                     270

Ala Pro Phe Phe Val Thr Asn Ile Val Asp Pro Phe Ile Asp Tyr Thr
             275                     280                     285

Val Pro Glu Lys Val Trp Thr Ala Phe Leu Trp Leu Gly Tyr Ile Asn
         290                     295                     300

Ser Gly Leu Asn Pro Phe Leu Tyr Ala Phe Leu Asn Lys Ser Phe Arg
305                     310                     315                     320

Arg Ala Phe Leu Ile Ile Leu Cys Cys Asp Asp Glu Arg Tyr Lys Arg
                     325                     330                     335

Pro Pro Ile Leu Gly Gln Thr Val Pro Cys Ser Thr Thr Thr Ile Asn
             340                     345                     350

Gly Ser Thr His Val Leu Arg Tyr Thr Val Leu His Ser Gly Gln His
         355                     360                     365

Gln Glu Leu Glu Lys Leu Pro Ile His Asn Asp Pro Glu Ser Leu Glu
370                     375                     380

Ser Cys Phe
385

(2) INFORMATION FOR SEQ ID NO:3:

(i) SEQUENCE CHARACTERISTICS:
        (A) LENGTH: 1622 base pairs
        (B) TYPE: nucleic acid
        (C) STRANDEDNESS: double
        (D) TOPOLOGY: unknown (ii) MOLECULE TYPE: cDNA (iii) HYPOTHETICAL: N (iv) ANTI-SENSE: N (vi) ORIGINAL SOURCE:
        (F) TISSUE TYPE: brain (vii) IMMEDIATE SOURCE:
        (A) LIBRARY: rat brain
        (B) CLONE: S10-95

(ix) FEATURE:
        (A) NAME/KEY: CDS
        (B) LOCATION: 50..1267
        (D) OTHER INFORMATION:

(xi) SEQUENCE DESCRIPTION: SEQ ID NO:3:

AGGGTCCTGT GGGCACTGAC ATCCAACGTA CTCATGCCCA TTTCCTGTA ATG GAC     55
                                                                                  Met Asp
                                                                                  1

AGA CTT GAT GCT AAT GTG AGT TCC AAC GAG GGT TTC GGG TCT GTG GAG    103
Arg Leu Asp Ala Asn Val Ser Ser Asn Glu Gly Phe Gly Ser Val Glu
                5                               10                         15

AAG GTC GTA CTG CTC ACG TTC TTC GCA ATG GTT ATC CTG ATG GCC ATC    151
Lys Val Val Leu Leu Thr Phe Phe Ala Met Val Ile Leu Met Ala Ile
     20                            25                           30

CTG GGC AAC CTG CTG GTG ATG GTT GCT GTG TGC AGG GAC AGG CAG CTC    199
Leu Gly Asn Leu Leu Val Met Val Ala Val Cys Arg Asp Arg Gln Leu
35                               40                         45                   50

AGG AAA ATA AAA ACC AAT TAT TTC ATT GTG TCT CTT GCC TTT GCT GAT    247

```
Arg Lys Ile Lys Thr Asn Tyr Phe Ile Val Ser Leu Ala Phe Ala Asp
              55                  60                  65

CTG CTG GTT TCG GTG CTG GTG AAT GCC TTC GGT GCC ATT GAG TTG GTC         295
Leu Leu Val Ser Val Leu Val Asn Ala Phe Gly Ala Ile Glu Leu Val
            70                  75                  80

CAA GAC ATC TGG TTT TAT GGG GAG ATG TTT TGC CTG GTC CGG ACC TCT         343
Gln Asp Ile Trp Phe Tyr Gly Glu Met Phe Cys Leu Val Arg Thr Ser
            85                  90                  95

CTG GAT GTC CTA CTC ACC ACA GCA TCA ATT TTT CAC CTC TGC TGC CTT         391
Leu Asp Val Leu Leu Thr Thr Ala Ser Ile Phe His Leu Cys Cys Leu
        100                 105                 110

TCC CTG GAT AGG TAT TAT GCC ATC TGC TGT CAA CCT TTG GTT TAT AGA         439
Ser Leu Asp Arg Tyr Tyr Ala Ile Cys Cys Gln Pro Leu Val Tyr Arg
115                 120                 125                 130

AAC AAG ATG ACC CCT CTA CGC ATC GCA TTA ATG CTG GGA GGC TGC TGG         487
Asn Lys Met Thr Pro Leu Arg Ile Ala Leu Met Leu Gly Gly Cys Trp
                135                 140                 145

GTC ATT CCC ATG TTT ATA TCT TTT CTC CCC ATA ATG CAA GGC TGG AAC         535
Val Ile Pro Met Phe Ile Ser Phe Leu Pro Ile Met Gln Gly Trp Asn
            150                 155                 160

AAC ATC GGC ATA GTT GAT GTG ATA GAG AAA AGG AAA TTC AAC CAC AAC         583
Asn Ile Gly Ile Val Asp Val Ile Glu Lys Arg Lys Phe Asn His Asn
            165                 170                 175

TCT AAC TCT ACA TTC TGT GTC TTC ATG GTC AAC AAG CCC TAT GCC ATC         631
Ser Asn Ser Thr Phe Cys Val Phe Met Val Asn Lys Pro Tyr Ala Ile
        180                 185                 190

ACC TGC TCT GTG GTG GCC TTC TAC ATC CCG TTT CTC CTC ATG GTG CTG         679
Thr Cys Ser Val Val Ala Phe Tyr Ile Pro Phe Leu Leu Met Val Leu
195                 200                 205                 210

GCC TAT TAC CGT ATC TAT GTC ACT GCT AAG GAG CAT GCC CAG CAG ATC         727
Ala Tyr Tyr Arg Ile Tyr Val Thr Ala Lys Glu His Ala Gln Gln Ile
                215                 220                 225

CAG ATG TTA CAA CGG GCA GGA GCC ACC TCT GAA AGC AGG CCC CAG ACA         775
Gln Met Leu Gln Arg Ala Gly Ala Thr Ser Glu Ser Arg Pro Gln Thr
            230                 235                 240

GCT GAC CAG CAC AGC ACA CAT CGC ATG CGG ACA GAG ACC AAA GCA GCC         823
Ala Asp Gln His Ser Thr His Arg Met Arg Thr Glu Thr Lys Ala Ala
            245                 250                 255

AAG ACT TTA TGT GTC ATC ATG GGC TGC TTC TGT TTC TGC TGG GCC CCC         871
Lys Thr Leu Cys Val Ile Met Gly Cys Phe Cys Phe Cys Trp Ala Pro
        260                 265                 270

TTC TTT GTC ACC AAT ATT GTG GAC CCT TTC ATA GAC TAC ACT GTG CCC         919
Phe Phe Val Thr Asn Ile Val Asp Pro Phe Ile Asp Tyr Thr Val Pro
275                 280                 285                 290

GAG AAG GTG TGG ACT GCT TTC CTC TGG CTT GGC TAT ATC AAT TCA GGG         967
Glu Lys Val Trp Thr Ala Phe Leu Trp Leu Gly Tyr Ile Asn Ser Gly
                295                 300                 305

TTG AAC CCT TTT CTC TAT GCC TTC TTG AAT AAG TCT TTC AGA CGT GCC         1015
Leu Asn Pro Phe Leu Tyr Ala Phe Leu Asn Lys Ser Phe Arg Arg Ala
            310                 315                 320

TTC CTT ATC ATC CTC TGC TGT GAT GAT GAG CGC TAC AAA AGA CCC CCC         1063
Phe Leu Ile Ile Leu Cys Cys Asp Asp Glu Arg Tyr Lys Arg Pro Pro
            325                 330                 335

ATT CTG GGC CAG ACT GTC CCC TGT TCA ACC ACA ACC ATT AAT GGA TCC         1111
Ile Leu Gly Gln Thr Val Pro Cys Ser Thr Thr Thr Ile Asn Gly Ser
        340                 345                 350

ACT CAT GTG CTA AGG GAT ACA GTG GAA TGT GGT GGC CAA TGG GAG AGT         1159
Thr His Val Leu Arg Asp Thr Val Glu Cys Gly Gly Gln Trp Glu Ser
355                 360                 365                 370

CGG TGT CAC CTC ACA GCA ACT TCT CCT TTG GTG GCT GCT CAG CCA GTG         1207
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Arg | Cys | His | Leu | Thr | Ala | Thr | Ser | Pro | Leu | Val | Ala | Ala | Gln | Pro | Val  |
|     |     |     |     | 375 |     |     |     | 380 |     |     |     |     | 385 |     |      |
| ATA | CGT | AGG | CCC | CAG | GAC | AAT | GAC | CTA | GAA | GAC | AGC | TGT | AGC | TTG | AAA  | 1255 |
| Ile | Arg | Arg | Pro | Gln | Asp | Asn | Asp | Leu | Glu | Asp | Ser | Cys | Ser | Leu | Lys  |
|     |     |     | 390 |     |     |     |     | 395 |     |     |     |     | 400 |     |      |
| AGA | AGC | CAG | TCC | TAAGCTGCTA | CTTCGGTGTA | TGTGGCTGCC | CCTGGCACTT |   |   |   |   |   |   |   |   | 1307 |
| Arg | Ser | Gln | Ser |   |   |   |   |   |   |   |   |   |   |   |   |
|     |     |     | 405 |   |   |   |   |   |   |   |   |   |   |   |   |

```
TGTTCTCCAA GGCTTTCCAA GAGCATGAGG CAATCCACCC TGGACTTCCC GCCACGATTC      1367
TAGCAGGCGG TATTAGAGGA AGTCAGGGGA GAGAAGGGCT TCCTCCTTAG CTTTCTGTTT      1427
CTCAACATTT TCTCTTCCTG GAGTCTCCAC TCTTGCTTGG TGGTCTCTGA AGTCCACGAC      1487
CCAGTCCCCT TTTGCTGTCT CCAGTCTGTC TTGTAAATGT TTACCGTGTT CGATTTTCAG      1547
TTTCCAAACA TGCCTTCTTT GAAGTGTCAT CTTACGATAC TGTCAAAACA TGTGCCTGTC      1607
TTGATCACAC TTCTT                                                        1622
```

( 2 ) INFORMATION FOR SEQ ID NO:4:

( i ) SEQUENCE CHARACTERISTICS:
        ( A ) LENGTH: 406 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Asp Arg Leu Asp Ala Asn Val Ser Ser Asn Glu Gly Phe Gly Ser
  1               5                  10                  15

Val Glu Lys Val Val Leu Leu Thr Phe Phe Ala Met Val Ile Leu Met
                 20                  25                  30

Ala Ile Leu Gly Asn Leu Leu Val Met Val Ala Val Cys Arg Asp Arg
             35                  40                  45

Gln Leu Arg Lys Ile Lys Thr Asn Tyr Phe Ile Val Ser Leu Ala Phe
         50                  55                  60

Ala Asp Leu Leu Val Ser Val Leu Val Asn Ala Phe Gly Ala Ile Glu
 65                  70                  75                  80

Leu Val Gln Asp Ile Trp Phe Tyr Gly Glu Met Phe Cys Leu Val Arg
                 85                  90                  95

Thr Ser Leu Asp Val Leu Leu Thr Thr Ala Ser Ile Phe His Leu Cys
                100                 105                 110

Cys Leu Ser Leu Asp Arg Tyr Tyr Ala Ile Cys Cys Gln Pro Leu Val
            115                 120                 125

Tyr Arg Asn Lys Met Thr Pro Leu Arg Ile Ala Leu Met Leu Gly Gly
    130                 135                 140

Cys Trp Val Ile Pro Met Phe Ile Ser Phe Leu Pro Ile Met Gln Gly
145                 150                 155                 160

Trp Asn Asn Ile Gly Ile Val Asp Val Ile Glu Lys Arg Lys Phe Asn
                165                 170                 175

His Asn Ser Asn Ser Thr Phe Cys Val Phe Met Val Asn Lys Pro Tyr
            180                 185                 190

Ala Ile Thr Cys Ser Val Val Ala Phe Tyr Ile Pro Phe Leu Leu Met
        195                 200                 205

Val Leu Ala Tyr Tyr Arg Ile Tyr Val Thr Ala Lys Glu His Ala Gln
    210                 215                 220

Gln Ile Gln Met Leu Gln Arg Ala Gly Ala Thr Ser Glu Ser Arg Pro
225                 230                 235                 240
```

| | | | | | | | | | | | | | | | |
|---|---|---|---|---|---|---|---|---|---|---|---|---|---|---|---|
| Gln | Thr | Ala | Asp | Gln<br>245 | His | Ser | Thr | His | Arg<br>250 | Met | Arg | Thr | Glu | Thr<br>255 | Lys |
| Ala | Ala | Lys | Thr<br>260 | Leu | Cys | Val | Ile | Met<br>265 | Gly | Cys | Phe | Cys<br>270 | Phe | Cys | Trp |
| Ala | Pro | Phe<br>275 | Phe | Val | Thr | Asn | Ile<br>280 | Val | Asp | Pro | Phe | Ile<br>285 | Asp | Tyr | Thr |
| Val | Pro<br>290 | Glu | Lys | Val | Trp | Thr<br>295 | Ala | Phe | Leu | Trp | Leu<br>300 | Gly | Tyr | Ile | Asn |
| Ser<br>305 | Gly | Leu | Asn | Pro | Phe<br>310 | Leu | Tyr | Ala | Phe | Leu<br>315 | Asn | Lys | Ser | Phe | Arg<br>320 |
| Arg | Ala | Phe | Leu | Ile<br>325 | Ile | Leu | Cys | Cys | Asp<br>330 | Asp | Glu | Arg | Tyr | Lys<br>335 | Arg |
| Pro | Pro | Ile | Leu<br>340 | Gly | Gln | Thr | Val | Pro<br>345 | Cys | Ser | Thr | Thr | Thr<br>350 | Ile | Asn |
| Gly | Ser | Thr<br>355 | His | Val | Leu | Arg | Asp<br>360 | Thr | Val | Glu | Cys | Gly<br>365 | Gly | Gln | Trp |
| Glu | Ser<br>370 | Arg | Cys | His | Leu | Thr<br>375 | Ala | Thr | Ser | Pro | Leu<br>380 | Val | Ala | Ala | Gln |
| Pro<br>385 | Val | Ile | Arg | Arg | Pro<br>390 | Gln | Asp | Asn | Asp | Leu<br>395 | Glu | Asp | Ser | Cys | Ser<br>400 |
| Leu | Lys | Arg | Ser | Gln<br>405 | Ser | | | | | | | | | | |

( 2 ) INFORMATION FOR SEQ ID NO:5:

( i ) SEQUENCE CHARACTERISTICS:
        ( A ) LENGTH: 536 base pairs
        ( B ) TYPE: nucleic acid
        ( C ) STRANDEDNESS: double
        ( D ) TOPOLOGY: unknown ( i i ) MOLECULE TYPE: cDNA ( i i i ) HYPOTHETICAL: N ( i v ) ANTI-SENSE: N ( v i ) ORIGINAL SOURCE:
        ( F ) TISSUE TYPE: brain ( v i i ) IMMEDIATE SOURCE:
        ( A ) LIBRARY: human brain
        ( B ) CLONE: S10 PCR ( i x ) FEATURE:
        ( A ) NAME/KEY: CDS
        ( B ) LOCATION: 1..534
        ( D ) OTHER INFORMATION:

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| TTG | GTC | TAT | AGG | AAC | AAG | ATG | ACC | CCT | CTG | CGC | ATC | GCA | TTA | ATG | CTG | 48 |
| Leu<br>1 | Val | Tyr | Arg | Asn<br>5 | Lys | Met | Thr | Pro | Leu<br>10 | Arg | Ile | Ala | Leu | Met<br>15 | Leu | |
| GGA | GGC | TGC | TGG | GTC | ATC | CCC | ACG | TTT | ATT | TCT | TTT | CTC | CCT | ATA | ATG | 96 |
| Gly | Gly | Cys | Trp<br>20 | Val | Ile | Pro | Thr | Phe<br>25 | Ile | Ser | Phe | Leu | Pro<br>30 | Ile | Met | |
| CAA | GGC | TGG | AAT | AAC | ATT | GGC | ATA | ATT | GAT | TTG | ATA | GAA | AAG | AGG | AAG | 144 |
| Gln | Gly | Trp<br>35 | Asn | Asn | Ile | Gly | Ile<br>40 | Ile | Asp | Leu | Ile | Glu<br>45 | Lys | Arg | Lys | |
| TTC | AAC | CAG | AAC | TCT | AAC | TCT | ACG | TAC | TGT | GTC | TTC | ATG | GTC | AAC | AAG | 192 |
| Phe | Asn<br>50 | Gln | Asn | Ser | Asn | Ser<br>55 | Thr | Tyr | Cys | Val | Phe<br>60 | Met | Val | Asn | Lys | |
| CCC | TAC | GCC | ATC | ACC | TGC | TCT | GTG | GTG | GCC | TTC | TAC | ATC | CCA | TTT | CTC | 240 |
| Pro | Tyr | Ala | Ile | Thr | Cys | Ser | Val | Val | Ala | Phe | Tyr | Ile | Pro | Phe | Leu | |

|  |  |  |  |  |  |  |  |  |  |  |  |  |  |  |  |
|---|---|---|---|---|---|---|---|---|---|---|---|---|---|---|---|
| CTC | ATG | GTG | CTG | GCC | TAT | TAC | CGC | ATC | TAT | GTC | ACA | GCT | AAG | GAG | CAT | 288
| Leu | Met | Val | Leu | Ala | Tyr | Tyr | Arg | Ile | Tyr | Val | Thr | Ala | Lys | Glu | His |
|     |     |     |     | 85  |     |     |     |     | 90  |     |     |     |     | 95  |     |
| GCC | CAT | CAG | ATC | CAG | ATG | TTA | CAA | CGG | GCA | GGA | GCC | TCC | TCC | GAG | AGC | 336
| Ala | His | Gln | Ile | Gln | Met | Leu | Gln | Arg | Ala | Gly | Ala | Ser | Ser | Glu | Ser |
|     |     |     | 100 |     |     |     |     | 105 |     |     |     |     | 110 |     |     |
| AGG | CCT | CAG | TCG | GCA | GAC | CAG | CAT | AGC | ACT | CAT | CCG | ATG | AGG | ACA | GAG | 384
| Arg | Pro | Gln | Ser | Ala | Asp | Gln | His | Ser | Thr | His | Pro | Met | Arg | Thr | Glu |
|     |     | 115 |     |     |     |     | 120 |     |     |     |     | 125 |     |     |     |
| ACC | AAA | GCA | GCC | AAG | ACC | CTG | TGC | ATC | ATC | ATG | GGT | TGC | TTC | TGC | CTC | 432
| Thr | Lys | Ala | Ala | Lys | Thr | Leu | Cys | Ile | Ile | Met | Gly | Cys | Phe | Cys | Leu |
|     | 130 |     |     |     |     | 135 |     |     |     |     | 140 |     |     |     |     |
| TGC | TGG | GCA | CCA | TTC | TTT | GTC | ACC | AAT | ATT | GTG | GAT | CCT | TTC | ATA | GAC | 480
| Cys | Trp | Ala | Pro | Phe | Phe | Val | Thr | Asn | Ile | Val | Asp | Pro | Phe | Ile | Asp |
| 145 |     |     |     |     | 150 |     |     |     |     | 155 |     |     |     |     | 160 |
| TAC | ACT | GTC | CCT | GGG | CAG | GTG | TGG | ACT | GCT | TTC | CTC | TGG | CTC | GGC | TAT | 528
| Tyr | Thr | Val | Pro | Gly | Gln | Val | Trp | Thr | Ala | Phe | Leu | Trp | Leu | Gly | Tyr |
|     |     |     |     | 165 |     |     |     |     | 170 |     |     |     |     | 175 |     |
| ATC | AAT | TC  |     |     |     |     |     |     |     |     |     |     |     |     |     | 536
| Ile | Asn |     |     |     |     |     |     |     |     |     |     |     |     |     |     |

( 2 ) INFORMATION FOR SEQ ID NO:6:

( i ) SEQUENCE CHARACTERISTICS:
( A ) LENGTH: 178 amino acids
( B ) TYPE: amino acid
( D ) TOPOLOGY: linear ( i i ) MOLECULE TYPE: protein ( x i ) SEQUENCE DESCRIPTION: SEQ ID NO:6:

| Leu | Val | Tyr | Arg | Asn | Lys | Met | Thr | Pro | Leu | Arg | Ile | Ala | Leu | Met | Leu |
|---|---|---|---|---|---|---|---|---|---|---|---|---|---|---|---|
| 1 |  |  |  | 5 |  |  |  |  | 10 |  |  |  |  | 15 |  |
| Gly | Gly | Cys | Trp | Val | Ile | Pro | Thr | Phe | Ile | Ser | Phe | Leu | Pro | Ile | Met |
|  |  |  | 20 |  |  |  |  | 25 |  |  |  |  | 30 |  |  |
| Gln | Gly | Trp | Asn | Asn | Ile | Gly | Ile | Ile | Asp | Leu | Ile | Glu | Lys | Arg | Lys |
|  |  |  | 35 |  |  |  |  | 40 |  |  |  |  | 45 |  |  |
| Phe | Asn | Gln | Asn | Ser | Asn | Ser | Thr | Tyr | Cys | Val | Phe | Met | Val | Asn | Lys |
|  | 50 |  |  |  |  | 55 |  |  |  |  | 60 |  |  |  |  |
| Pro | Tyr | Ala | Ile | Thr | Cys | Ser | Val | Val | Ala | Phe | Tyr | Ile | Pro | Phe | Leu |
| 65 |  |  |  |  | 70 |  |  |  |  | 75 |  |  |  |  | 80 |
| Leu | Met | Val | Leu | Ala | Tyr | Tyr | Arg | Ile | Tyr | Val | Thr | Ala | Lys | Glu | His |
|  |  |  |  | 85 |  |  |  |  | 90 |  |  |  |  | 95 |  |
| Ala | His | Gln | Ile | Gln | Met | Leu | Gln | Arg | Ala | Gly | Ala | Ser | Ser | Glu | Ser |
|  |  |  | 100 |  |  |  |  | 105 |  |  |  |  | 110 |  |  |
| Arg | Pro | Gln | Ser | Ala | Asp | Gln | His | Ser | Thr | His | Pro | Met | Arg | Thr | Glu |
|  |  | 115 |  |  |  |  | 120 |  |  |  |  | 125 |  |  |  |
| Thr | Lys | Ala | Ala | Lys | Thr | Leu | Cys | Ile | Ile | Met | Gly | Cys | Phe | Cys | Leu |
|  | 130 |  |  |  |  | 135 |  |  |  |  | 140 |  |  |  |  |
| Cys | Trp | Ala | Pro | Phe | Phe | Val | Thr | Asn | Ile | Val | Asp | Pro | Phe | Ile | Asp |
| 145 |  |  |  |  | 150 |  |  |  |  | 155 |  |  |  |  | 160 |
| Tyr | Thr | Val | Pro | Gly | Gln | Val | Trp | Thr | Ala | Phe | Leu | Trp | Leu | Gly | Tyr |
|  |  |  |  | 165 |  |  |  |  | 170 |  |  |  |  | 175 |  |
| Ile | Asn |  |  |  |  |  |  |  |  |  |  |  |  |  |  |

( 2 ) INFORMATION FOR SEQ ID NO:7:

( i ) SEQUENCE CHARACTERISTICS:

(A) LENGTH: 1316 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(F) TISSUE TYPE: Brain (vii) IMMEDIATE SOURCE:
(A) LIBRARY: Human Brain
(B) CLONE: S10-87

(ix) FEATURE:
(A) NAME/KEY: CDS
(B) LOCATION: 7..1170

(xi) SEQUENCE DESCRIPTION: SEQ ID NO:7:

```
CCTGTA ATG GAC AAA CTT GAT GCT AAT GTG AGT TCT GAG GAG GGT TTC         48
       Met Asp Lys Leu Asp Ala Asn Val Ser Ser Glu Glu Gly Phe
        1           5                  10

GGG TCA GTG GAG AAG GTG GTG CTG CTC ACG TTT CTC TCG ACG GTT ATC         96
Gly Ser Val Glu Lys Val Val Leu Leu Thr Phe Leu Ser Thr Val Ile
 15              20                  25                  30

CTG ATG GCC ATC TTG GGG AAC CTG CTG GTG ATG GTG GCT GTG TGC TGG        144
Leu Met Ala Ile Leu Gly Asn Leu Leu Val Met Val Ala Val Cys Trp
                 35                  40                  45

GAC AGG CAG CTC AGG AAA ATA AAA ACA AAT TAT TTC ATT GTA TCT CTT        192
Asp Arg Gln Leu Arg Lys Ile Lys Thr Asn Tyr Phe Ile Val Ser Leu
             50                  55                  60

GCT TTT GCG GAT CTG CTG GTT TCG GTG CTG GTG ATG CCC TTT GGT GCC        240
Ala Phe Ala Asp Leu Leu Val Ser Val Leu Val Met Pro Phe Gly Ala
         65                  70                  75

ATT GAG CTG GTT CAA GAC ATC TGG ATT TAT GGG GAG GTG TTT TGT CTT        288
Ile Glu Leu Val Gln Asp Ile Trp Ile Tyr Gly Glu Val Phe Cys Leu
     80                  85                  90

GTT CGG ACA TCT CTG GAC GTC CTG CTC ACA ACG GCA TCG ATT TTT CAC        336
Val Arg Thr Ser Leu Asp Val Leu Leu Thr Thr Ala Ser Ile Phe His
 95                 100                 105                 110

CTG TGC TGC ATT TCT CTG GAT AGG TAT TAC GCC ATC TGC TGC CAG CCT        384
Leu Cys Cys Ile Ser Leu Asp Arg Tyr Tyr Ala Ile Cys Cys Gln Pro
                115                 120                 125

TTG GTC TAT AGG AAC AAG ATG ACC CCT CTG CGC ATC GCA TTA ATG CTG        432
Leu Val Tyr Arg Asn Lys Met Thr Pro Leu Arg Ile Ala Leu Met Leu
            130                 135                 140

GGA GGC TGC TGG GTC ATC CCC ACG TTT ATT TCT TTC CTC CCT ATA ATG        480
Gly Gly Cys Trp Val Ile Pro Thr Phe Ile Ser Phe Leu Pro Ile Met
        145                 150                 155

CAA GGC TGG AAT AAC ATT GGC ATA ATT GAT TTG ATA GAA AAG AGG AAG        528
Gln Gly Trp Asn Asn Ile Gly Ile Ile Asp Leu Ile Glu Lys Arg Lys
    160                 165                 170

TTC AAC CAG AAC TCT AAC TCT ACG TAC TGT GTC TTC ATG GTC AAC AAG        576
Phe Asn Gln Asn Ser Asn Ser Thr Tyr Cys Val Phe Met Val Asn Lys
175                 180                 185                 190

CCC TAC GCC ATC ACC TGC TCT GTG GTG GCC TTC TAC ATC CCA TTT CTC        624
Pro Tyr Ala Ile Thr Cys Ser Val Val Ala Phe Tyr Ile Pro Phe Leu
                195                 200                 205

CTC ATG GTG CTG GCC TAT TAC CGC ATC TAT GTC ACA GCT AAG GAG CAT        672
Leu Met Val Leu Ala Tyr Tyr Arg Ile Tyr Val Thr Ala Lys Glu His
            210                 215                 220
```

| | | | | | | | | | | | | | | | | |
|---|---|---|---|---|---|---|---|---|---|---|---|---|---|---|---|---|
|GCC|CAT|CAG|ATC|CAG|ATG|TTA|CAA|CGG|GCA|GGA|GCC|TCC|TCC|GAG|AGC|720|
|Ala|His|Gln|Ile|Gln|Met|Leu|Gln|Arg|Ala|Gly|Ala|Ser|Ser|Glu|Ser| |
| |225| | | |230| | | | | |235| | | | | |

| | | | | | | | | | | | | | | | | |
|---|---|---|---|---|---|---|---|---|---|---|---|---|---|---|---|---|
|AGG|CCT|CAG|TCG|GCA|GAC|CAG|CAT|AGC|ACT|CAT|CGC|ATG|AGG|ACA|GAG|768|
|Arg|Pro|Gln|Ser|Ala|Asp|Gln|His|Ser|Thr|His|Arg|Met|Arg|Thr|Glu| |
| |240| | | |245| | | | |250| | | | | | |

| | | | | | | | | | | | | | | | | |
|---|---|---|---|---|---|---|---|---|---|---|---|---|---|---|---|---|
|ACC|AAA|GCA|GCC|AAG|ACC|CTG|TGC|ATC|ATC|ATG|GGT|TGC|TTC|TGC|CTC|816|
|Thr|Lys|Ala|Ala|Lys|Thr|Leu|Cys|Ile|Ile|Met|Gly|Cys|Phe|Cys|Leu| |
|255| | | | |260| | | | |265| | | | |270| |

| | | | | | | | | | | | | | | | | |
|---|---|---|---|---|---|---|---|---|---|---|---|---|---|---|---|---|
|TGC|TGG|GCA|CCA|TTC|TTT|GTC|ACC|AAT|ATT|GTG|GAT|CCT|TTC|ATA|GAC|864|
|Cys|Trp|Ala|Pro|Phe|Phe|Val|Thr|Asn|Ile|Val|Asp|Pro|Phe|Ile|Asp| |
| | | | |275| | | | |280| | | | |285| | |

| | | | | | | | | | | | | | | | | |
|---|---|---|---|---|---|---|---|---|---|---|---|---|---|---|---|---|
|TAC|ACT|GTC|CCT|GGG|CAG|GTG|TGG|ACT|GCT|TTC|CTC|TGG|CTC|GGC|TAT|912|
|Tyr|Thr|Val|Pro|Gly|Gln|Val|Trp|Thr|Ala|Phe|Leu|Trp|Leu|Gly|Tyr| |
| | | |290| | | | |295| | | | |300| | | |

| | | | | | | | | | | | | | | | | |
|---|---|---|---|---|---|---|---|---|---|---|---|---|---|---|---|---|
|ATC|AAT|TCC|GGG|TTG|AAC|CCT|TTT|CTC|TAC|GCC|TTC|TTG|AAT|AAG|TCT|960|
|Ile|Asn|Ser|Gly|Leu|Asn|Pro|Phe|Leu|Tyr|Ala|Phe|Leu|Asn|Lys|Ser| |
| | |305| | | | |310| | | | |315| | | | |

| | | | | | | | | | | | | | | | | |
|---|---|---|---|---|---|---|---|---|---|---|---|---|---|---|---|---|
|TTT|AGA|CGT|GCC|TTC|CTC|ATC|ATC|CTC|TGC|TGT|GAT|GAT|GAG|CGC|TAC|1008|
|Phe|Arg|Arg|Ala|Phe|Leu|Ile|Ile|Leu|Cys|Cys|Asp|Asp|Glu|Arg|Tyr| |
| |320| | | |325| | | | |330| | | | | | |

| | | | | | | | | | | | | | | | | |
|---|---|---|---|---|---|---|---|---|---|---|---|---|---|---|---|---|
|CGA|AGA|CCT|TCC|ATT|CTG|GGC|CAG|ACT|GTC|CCT|TGT|TCA|ACC|ACA|ACC|1056|
|Arg|Arg|Pro|Ser|Ile|Leu|Gly|Gln|Thr|Val|Pro|Cys|Ser|Thr|Thr|Thr| |
|335| | | | |340| | | | |345| | | | |350| |

| | | | | | | | | | | | | | | | | |
|---|---|---|---|---|---|---|---|---|---|---|---|---|---|---|---|---|
|ATT|AAT|GGA|TCC|ACA|CAT|GTA|CTA|AGG|GAT|GCA|GTG|GAG|TGT|GGT|GGC|1104|
|Ile|Asn|Gly|Ser|Thr|His|Val|Leu|Arg|Asp|Ala|Val|Glu|Cys|Gly|Gly| |
| | | | |355| | | | |360| | | | |365| | |

| | | | | | | | | | | | | | | | | |
|---|---|---|---|---|---|---|---|---|---|---|---|---|---|---|---|---|
|CAG|TGG|GAG|AGT|CAG|TGT|CAC|CCG|CCA|GCA|ACT|TCT|CCT|TTG|GTG|GCT|1152|
|Gln|Trp|Glu|Ser|Gln|Cys|His|Pro|Pro|Ala|Thr|Ser|Pro|Leu|Val|Ala| |
| | | |370| | | | |375| | | | |380| | | |

| | | | | | | |
|---|---|---|---|---|---|---|
|GCT|CAG|CCC|AGT|GAC|ACT|TAGGCCCCTG GGACAATGAC CCAGAAGACA|1200|
|Ala|Gln|Pro|Ser|Asp|Thr| | |
| | | |385| | | | |

GCCATGCCTC CGAAAGAGGG CCAGGTCCTA AGCTGCTGCT TGTGCGCGAC TGCACCCGGC 1260

ATTCTCTTCA CCTGAGGCTT TCCGTCCGCC AGTGCAGGAA CCCGGTGCTC GCTGGG 1316

( 2 ) INFORMATION FOR SEQ ID NO:8:

( i ) SEQUENCE CHARACTERISTICS:
        ( A ) LENGTH: 388 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | | |
|---|---|---|---|---|---|---|---|---|---|---|---|---|---|---|---|
|Met|Asp|Lys|Leu|Asp|Ala|Asn|Val|Ser|Ser|Glu|Glu|Gly|Phe|Gly|Ser|
|1| | | |5| | | | |10| | | | |15| |

| | | | | | | | | | | | | | | | |
|---|---|---|---|---|---|---|---|---|---|---|---|---|---|---|---|
|Val|Glu|Lys|Val|Val|Leu|Leu|Thr|Phe|Leu|Ser|Thr|Val|Ile|Leu|Met|
| | | |20| | | | |25| | | | |30| | |

| | | | | | | | | | | | | | | | |
|---|---|---|---|---|---|---|---|---|---|---|---|---|---|---|---|
|Ala|Ile|Leu|Gly|Asn|Leu|Leu|Val|Met|Val|Ala|Val|Cys|Trp|Asp|Arg|
| | |35| | | | |40| | | | |45| | | |

| | | | | | | | | | | | | | | | |
|---|---|---|---|---|---|---|---|---|---|---|---|---|---|---|---|
|Gln|Leu|Arg|Lys|Ile|Lys|Thr|Asn|Tyr|Phe|Ile|Val|Ser|Leu|Ala|Phe|
| |50| | | | |55| | | | |60| | | | |

| | | | | | | | | | | | | | | | |
|---|---|---|---|---|---|---|---|---|---|---|---|---|---|---|---|
|Ala|Asp|Leu|Leu|Val|Ser|Val|Leu|Val|Met|Pro|Phe|Gly|Ala|Ile|Glu|
|65| | | | |70| | | | |75| | | | |80|

| | | | | | | | | | | | | | | | |
|---|---|---|---|---|---|---|---|---|---|---|---|---|---|---|---|
|Leu|Val|Gln|Asp|Ile|Trp|Ile|Tyr|Gly|Glu|Val|Phe|Cys|Leu|Val|Arg|
| | | |85| | | | |90| | | | |95| | |

| | | | | | | | | | | | | | | | |
|---|---|---|---|---|---|---|---|---|---|---|---|---|---|---|---|
|Thr|Ser|Leu|Asp|Val|Leu|Leu|Thr|Thr|Ala|Ser|Ile|Phe|His|Leu|Cys|
| | |100| | | | |105| | | | |110| | | |

-continued

| | | | | | | | | | | | | | |
|---|---|---|---|---|---|---|---|---|---|---|---|---|---|
|Cys|Ile|Ser|Leu|Asp|Arg|Tyr|Tyr|Ala|Ile|Cys|Cys|Gln|Pro|Leu|Val|
| | |115| | | | |120| | | | |125| | | |
|Tyr|Arg|Asn|Lys|Met|Thr|Pro|Leu|Arg|Ile|Ala|Leu|Met|Leu|Gly|Gly|
| |130| | | | |135| | | | |140| | | | |
|Cys|Trp|Val|Ile|Pro|Thr|Phe|Ile|Ser|Phe|Leu|Pro|Ile|Met|Gln|Gly|
|145| | | | |150| | | | |155| | | | |160|
|Trp|Asn|Asn|Ile|Gly|Ile|Ile|Asp|Leu|Ile|Glu|Lys|Arg|Lys|Phe|Asn|
| | | | |165| | | | |170| | | | |175| |
|Gln|Asn|Ser|Asn|Ser|Thr|Tyr|Cys|Val|Phe|Met|Val|Asn|Lys|Pro|Tyr|
| | | |180| | | | |185| | | | |190| | |
|Ala|Ile|Thr|Cys|Ser|Val|Val|Ala|Phe|Tyr|Ile|Pro|Phe|Leu|Leu|Met|
| | |195| | | | |200| | | | |205| | | |
|Val|Leu|Ala|Tyr|Tyr|Arg|Ile|Tyr|Val|Thr|Ala|Lys|Glu|His|Ala|His|
| |210| | | | |215| | | | |220| | | | |
|Gln|Ile|Gln|Met|Leu|Gln|Arg|Ala|Gly|Ala|Ser|Ser|Glu|Ser|Arg|Pro|
|225| | | | |230| | | | |235| | | | |240|
|Gln|Ser|Ala|Asp|Gln|His|Ser|Thr|His|Arg|Met|Arg|Thr|Glu|Thr|Lys|
| | | | |245| | | | |250| | | | |255| |
|Ala|Ala|Lys|Thr|Leu|Cys|Ile|Ile|Met|Gly|Cys|Phe|Cys|Leu|Cys|Trp|
| | | |260| | | | |265| | | | |270| | |
|Ala|Pro|Phe|Phe|Val|Thr|Asn|Ile|Val|Asp|Pro|Phe|Ile|Asp|Tyr|Thr|
| | |275| | | | |280| | | | |285| | | |
|Val|Pro|Gly|Gln|Val|Trp|Thr|Ala|Phe|Leu|Trp|Leu|Gly|Tyr|Ile|Asn|
| |290| | | | |295| | | | |300| | | | |
|Ser|Gly|Leu|Asn|Pro|Phe|Leu|Tyr|Ala|Phe|Leu|Asn|Lys|Ser|Phe|Arg|
|305| | | | |310| | | | |315| | | | |320|
|Arg|Ala|Phe|Leu|Ile|Ile|Leu|Cys|Cys|Asp|Asp|Glu|Arg|Tyr|Arg|Arg|
| | | | |325| | | | |330| | | | |335| |
|Pro|Ser|Ile|Leu|Gly|Gln|Thr|Val|Pro|Cys|Ser|Thr|Thr|Thr|Ile|Asn|
| | | |340| | | | |345| | | | |350| | |
|Gly|Ser|Thr|His|Val|Leu|Arg|Asp|Ala|Val|Glu|Cys|Gly|Gly|Gln|Trp|
| | |355| | | | |360| | | | |365| | | |
|Glu|Ser|Gln|Cys|His|Pro|Pro|Ala|Thr|Ser|Pro|Leu|Val|Ala|Ala|Gln|
| |370| | | | |375| | | | |380| | | | |
|Pro|Ser|Asp|Thr|
|385| | | |

( 2 ) INFORMATION FOR SEQ ID NO:9:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: modified_base
    ( B ) LOCATION: 14

( i x ) FEATURE:
    ( A ) NAME/KEY: modified_base
    ( B ) LOCATION: 20

( x i ) SEQUENCE DESCRIPTION: SEQ ID NO:9:

TGGAATTCTG YGYAATHKCA CTGGAYMGST A                                                                                       31

( 2 ) INFORMATION FOR SEQ ID NO:10:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: modified_base
        ( B ) LOCATION: 4

( i x ) FEATURE:
        ( A ) NAME/KEY: modified_base
        ( B ) LOCATION: 7

( i x ) FEATURE:
        ( A ) NAME/KEY: modified_base
        ( B ) LOCATION: 9..10

( i x ) FEATURE:
        ( A ) NAME/KEY: modified_base
        ( B ) LOCATION: 13

( i x ) FEATURE:
        ( A ) NAME/KEY: modified_base
        ( B ) LOCATION: 25

( x i ) SEQUENCE DESCRIPTION: SEQ ID NO:10:

CATAAVARAA ARAGGDATRW ARAAAGC                                                                                            27

( 2 ) INFORMATION FOR SEQ ID NO:11:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

TCAAAAGCAT GATTCCAGGG ACTCTGGGTC ATTGTGTATG GGCAA                                                                        45

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

CCTCAATCAG AAGCATGATT CCAGG                                                                                              25

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

```
TTGGTCTATA GGAACAAGAT GACCC                                           25
```

( 2 ) INFORMATION FOR SEQ ID NO:14:

( i ) SEQUENCE CHARACTERISTICS:
        ( A ) LENGTH: 792 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( F ) TISSUE TYPE: Brain ( v i i ) IMMEDIATE SOURCE:
        ( A ) LIBRARY: HUMAN BRAIN
        ( B ) CLONE: S10-87

( i x ) FEATURE:
        ( A ) NAME/KEY: CDS
        ( B ) LOCATION: 1..783

( x i ) SEQUENCE DESCRIPTION: SEQ ID NO:14:

```
TTG  GTC  TAT  AGG  AAC  AAG  ATG  ACC  CCT  CTG  CGC  ATC  GCA  TTA  ATG  CTG    48
Leu  Val  Tyr  Arg  Asn  Lys  Met  Thr  Pro  Leu  Arg  Ile  Ala  Leu  Met  Leu
 1              5                        10                       15

GGA  GGC  TGC  TGG  GTC  ATC  CCC  ACG  TTT  ATT  TCT  TTT  CTC  CCT  ATA  ATG    96
Gly  Gly  Cys  Trp  Val  Ile  Pro  Thr  Phe  Ile  Ser  Phe  Leu  Pro  Ile  Met
              20                       25                       30

CAA  GGC  TGG  AAT  AAC  ATT  GGC  ATA  ATT  GAT  TTG  ATA  GAA  AAG  AGG  AAG   144
Gln  Gly  Trp  Asn  Asn  Ile  Gly  Ile  Ile  Asp  Leu  Ile  Glu  Lys  Arg  Lys
         35                       40                       45

TTC  AAC  CAG  AAC  TCT  AAC  TCT  ACG  TAC  TGT  GTC  TTC  ATG  GTC  AAC  AAG   192
Phe  Asn  Gln  Asn  Ser  Asn  Ser  Thr  Tyr  Cys  Val  Phe  Met  Val  Asn  Lys
     50                       55                       60

CCC  TAC  GCC  ATC  ACC  TGC  TCT  GTG  GTG  GCC  TTC  TAC  ATC  CCA  TTT  CTC   240
Pro  Tyr  Ala  Ile  Thr  Cys  Ser  Val  Val  Ala  Phe  Tyr  Ile  Pro  Phe  Leu
 65                       70                       75                       80

CTC  ATG  GTG  CTG  GCC  TAT  TAC  CGC  ATC  TAT  GTC  ACA  GCT  AAG  GAG  CAT   288
Leu  Met  Val  Leu  Ala  Tyr  Tyr  Arg  Ile  Tyr  Val  Thr  Ala  Lys  Glu  His
                       85                       90                       95

GCC  CAT  CAG  ATC  CAG  ATG  TTA  CAA  CGG  GCA  GGA  GCC  TCC  TCC  GAG  AGC   336
Ala  His  Gln  Ile  Gln  Met  Leu  Gln  Arg  Ala  Gly  Ala  Ser  Ser  Glu  Ser
              100                      105                      110

AGG  CCT  CAG  TCG  GCA  GAC  CAG  CAT  AGC  ACT  CAT  CGC  ATG  AGG  ACA  GAG   384
Arg  Pro  Gln  Ser  Ala  Asp  Gln  His  Ser  Thr  His  Arg  Met  Arg  Thr  Glu
         115                      120                      125

ACC  AAA  GCA  GCC  AAG  ACC  CTG  TGC  ATC  ATC  ATG  GGT  TGC  TTC  TGC  CTC   432
Thr  Lys  Ala  Ala  Lys  Thr  Leu  Cys  Ile  Ile  Met  Gly  Cys  Phe  Cys  Leu
```

```
                   130                       135                          140
      TGC TGG GCA CCA TTC TTT GTC ACC AAT ATT GTG GAT CCT TTC ATA GAC         480
      Cys Trp Ala Pro Phe Phe Val Thr Asn Ile Val Asp Pro Phe Ile Asp
      145             150                     155                     160

TAC ACT GTC CCT GGG CAG GTG TGG ACT GCT TTC CTC TGG CTC GGC TAT         528
      Tyr Thr Val Pro Gly Gln Val Trp Thr Ala Phe Leu Trp Leu Gly Tyr
                          165                     170                 175

ATC AAT TCC GGG TTG AAC CCT TTT CTC TAC GCC TTC TTG AAT AAG TCT         576
      Ile Asn Ser Gly Leu Asn Pro Phe Leu Tyr Ala Phe Leu Asn Lys Ser
                      180                     185                 190

TTT AGA CGT GCC TTC CTC ATC ATC CTC TGC TGT GAT GAT GAG CGC TAC         624
      Phe Arg Arg Ala Phe Leu Ile Ile Leu Cys Cys Asp Asp Glu Arg Tyr
                  195                     200                 205

CGA AGA CCT TCC ATT CTG GGC CAG ACT GTC CCT TGT TCA ACC ACA ACC         672
      Arg Arg Pro Ser Ile Leu Gly Gln Thr Val Pro Cys Ser Thr Thr Thr
              210                     215                 220

ATT AAT GGA TCC ACA CAT GTA CTA AGG TAC ACC GTT CTG CAC AGG GGA         720
      Ile Asn Gly Ser Thr His Val Leu Arg Tyr Thr Val Leu His Arg Gly
      225                     230                 235                 240

CAT CAT CAG GAA CTC GAG AAA CTG CCC ATA CAC AAT GAC CCA GAA TCC         768
      His His Gln Glu Leu Glu Lys Leu Pro Ile His Asn Asp Pro Glu Ser
                              245                 250                 255

CTG GAA TCA TGC TTC TGATTGAGG                                           792
      Leu Glu Ser Cys Phe
                      260
```

( 2 ) INFORMATION FOR SEQ ID NO:15:

( i ) SEQUENCE CHARACTERISTICS:
        ( A ) LENGTH: 261 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Leu Val Tyr Arg Asn Lys Met Thr Pro Leu Arg Ile Ala Leu Met Leu
1               5                   10                  15

Gly Gly Cys Trp Val Ile Pro Thr Phe Ile Ser Phe Leu Pro Ile Met
                20                  25                  30

Gln Gly Trp Asn Asn Ile Gly Ile Ile Asp Leu Ile Glu Lys Arg Lys
                35                  40                  45

Phe Asn Gln Asn Ser Asn Ser Thr Tyr Cys Val Phe Met Val Asn Lys
        50                  55                  60

Pro Tyr Ala Ile Thr Cys Ser Val Val Ala Phe Tyr Ile Pro Phe Leu
65                  70                  75                  80

Leu Met Val Leu Ala Tyr Tyr Arg Ile Tyr Val Thr Ala Lys Glu His
                85                  90                  95

Ala His Gln Ile Gln Met Leu Gln Arg Ala Gly Ala Ser Ser Glu Ser
                100                 105                 110

Arg Pro Gln Ser Ala Asp Gln His Ser Thr His Arg Met Arg Thr Glu
                115                 120                 125

Thr Lys Ala Ala Lys Thr Leu Cys Ile Ile Met Gly Cys Phe Cys Leu
                130                 135                 140

Cys Trp Ala Pro Phe Phe Val Thr Asn Ile Val Asp Pro Phe Ile Asp
145                 150                 155                 160

Tyr Thr Val Pro Gly Gln Val Trp Thr Ala Phe Leu Trp Leu Gly Tyr
                165                 170                 175

Ile Asn Ser Gly Leu Asn Pro Phe Leu Tyr Ala Phe Leu Asn Lys Ser
```

-continued

|   |   |   | | | | 180 | | | | | | 185 | | | | | 190 | | |
|---|---|---|---|---|---|---|---|---|---|---|---|---|---|---|---|---|---|---|---|
| Phe | Arg | Arg 195 | Ala | Phe | Leu | Ile | Ile 200 | Leu | Cys | Cys | Asp | Asp 205 | Glu | Arg | Tyr | | | | |
| Arg | Arg 210 | Pro | Ser | Ile | Leu | Gly | Gln 215 | Thr | Val | Pro | Cys 220 | Ser | Thr | Thr | Thr | | | | |
| Ile 225 | Asn | Gly | Ser | Thr | His 230 | Val | Leu | Arg | Tyr | Thr 235 | Val | Leu | His | Arg | Gly 240 | | | | |
| His | His | Gln | Glu | Leu 245 | Glu | Lys | Leu | Pro | Ile 250 | His | Asn | Asp | Pro | Glu 255 | Ser | | | | |
| Leu | Glu | Ser | Cys 260 | Phe | | | | | | | | | | | | | | | |